(12) United States Patent
Boileau et al.

(10) Patent No.: US 9,402,650 B2
(45) Date of Patent: Aug. 2, 2016

(54) SURGICAL FASTENING

(71) Applicant: Smith & Nephew, Inc., Andover, MA (US)

(72) Inventors: Pascal Boileau, Nice (FR); Mason James Bettenga, Memphis, TN (US); Christoph Haessig, Kuttigen (CH); Dirk Wunderle, Zurich (CH); Alexander Iwan Seidl, Zurich (CH); Oliver Streit, Tuttlingen (DE); Stephen Anthony Santangelo, Sturbridge, MA (US)

(73) Assignee: Smith & Nephew, Inc., Memphis, TN (US)

( * ) Notice: Subject to any disclaimer, the term of this patent is extended or adjusted under 35 U.S.C. 154(b) by 192 days.

(21) Appl. No.: 14/214,251

(22) Filed: Mar. 14, 2014

(65) Prior Publication Data

US 2014/0277185 A1    Sep. 18, 2014

Related U.S. Application Data

(60) Provisional application No. 61/794,212, filed on Mar. 15, 2013.

(51) Int. Cl.
*A61B 17/56*    (2006.01)
*A61B 17/17*    (2006.01)
(Continued)

(52) U.S. Cl.
CPC .................. *A61B 17/56* (2013.01); *A61B 17/02* (2013.01); *A61B 17/025* (2013.01);
(Continued)

(58) Field of Classification Search
CPC .. A61B 17/02; A61B 17/0206; A61B 17/025; A61B 17/0401; A61B 2017/0404; A61B 2017/0496; A61B 17/1739; A61B 2017/1778; A61B 17/56; A61B 2017/564; A61B 17/683; A61B 17/88; A61B 17/8869

See application file for complete search history.

(56) References Cited

U.S. PATENT DOCUMENTS 1,798,124 A    3/1931    Hunn
5,626,607 A    5/1997    Malecki et al.
(Continued)

FOREIGN PATENT DOCUMENTS

CN    101573078 A    11/2009
EP    1588669 A1    10/2005
(Continued)

OTHER PUBLICATIONS

Patent Examination Report No. 1 from related Australian Patent Application No. 2012261928 issued Dec. 17, 2015.
(Continued)

*Primary Examiner* — Larry E Waggle, Jr.
(74) *Attorney, Agent, or Firm* — Burns & Levinson LLP; Joseph M. Maraia

(57) ABSTRACT

Methods of joint repair employing sutures and attached fixation devices are discussed. For example, a bone block graft procedure (e.g., Latarjet) is discussed which employs fixation devices to secure contact between graft surfaces of two bones. A suture construct, including a continuous suture loop routed through a first fastener, is secured to a first bone. Looped ends of the suture loop are passed through passageways formed in the two bones. The looped suture ends are further routed through a second fastener. The second fastener is mounted to the second bone and a sliding knot, formed in the looped suture ends, is advanced into contact with the second fastener. The suture is further tensioned using a tensioner device to secure the two bones together.

27 Claims, 45 Drawing Sheets

(51) Int. Cl.
*A61B 17/02* (2006.01)
*A61B 17/88* (2006.01)
*A61B 17/04* (2006.01)
*A61B 17/16* (2006.01)
*A61B 17/68* (2006.01)
*A61B 17/14* (2006.01)

(52) U.S. Cl.
CPC ........ *A61B 17/0206* (2013.01); *A61B 17/0401* (2013.01); *A61B 17/148* (2013.01); *A61B 17/1659* (2013.01); *A61B 17/1739* (2013.01); *A61B 17/683* (2013.01); *A61B 17/88* (2013.01); *A61B 17/8888* (2013.01); *A61B 17/141* (2013.01); *A61B 17/8869* (2013.01); *A61B 17/8877* (2013.01); *A61B 2017/0404* (2013.01); *A61B 2017/0496* (2013.01); *A61B 2017/1778* (2013.01); *A61B 2017/564* (2013.01)

(56) References Cited

U.S. PATENT DOCUMENTS

| | | | |
|---|---|---|---|
| 6,149,669 | A | 11/2000 | Li |
| 6,514,274 | B1 | 2/2003 | Boucher et al. |
| 8,728,131 | B2 * | 5/2014 | Di Giacomo ........ A61B 17/809 606/297 |
| 8,926,661 | B2 * | 1/2015 | Sikora ................ A61B 17/0401 606/232 |
| 2005/0043717 | A1 | 2/2005 | Snow |
| 2005/0283192 | A1 | 12/2005 | Torrie et al. |
| 2006/0190041 | A1 | 8/2006 | Fallin et al. |
| 2007/0150002 | A1 | 6/2007 | Szabo et al. |
| 2007/0276370 | A1 | 11/2007 | Altarac et al. |
| 2007/0288023 | A1 | 12/2007 | Pellegrino et al. |
| 2008/0027435 | A1 | 1/2008 | Zucherman et al. |
| 2009/0093684 | A1 | 4/2009 | Schorer |
| 2010/0125297 | A1 | 5/2010 | Guederain et al. |
| 2011/0087280 | A1 | 4/2011 | Albertorio |
| 2012/0010471 | A1 | 1/2012 | Mire et al. |
| 2013/0085494 | A1 | 4/2013 | Weisenburgh, II et al. |
| 2013/0138108 | A1 | 5/2013 | Dreyfuss et al. |

FOREIGN PATENT DOCUMENTS

| | | |
|---|---|---|
| FR | 903 E | 4/1903 |
| JP | 2002-58676 | 2/2002 |
| JP | 2008-543509 A | 12/2008 |
| JP | 2009-521266 A | 6/2009 |
| JP | 2011-25036 A | 2/2011 |
| WO | 9848702 | 11/1998 |
| WO | 2008139260 A2 | 11/2008 |
| WO | 2009098086 A1 | 8/2009 |

OTHER PUBLICATIONS

First Office Action from related Chinese Patent Application No. 201280038096.X issued Oct. 12, 2015.

International Search Report and Written Opinion for PCT/US2014/029497 mailed Oct. 29, 2014.

Invitation to Pay Additional Fees and, Where Applicable, Protest Fee for PCT/US2014/029497 mailed Aug. 7, 2014.

International Preliminary Report for PCT/US2014/029497 mailed Sep. 24, 2015.

Substantive Examination of related Mexican Application No. MX/a/2013/014164 mailed Feb. 12, 2016.

Communication pursuant to Article 94(3) EPC for related European Application No. 12727024.7 mailed Nov. 24, 2015.

Notice of Reasons for Rejection from related Japanese Patent Application No. 2014-513759 mailed Feb. 2, 2016.

* cited by examiner

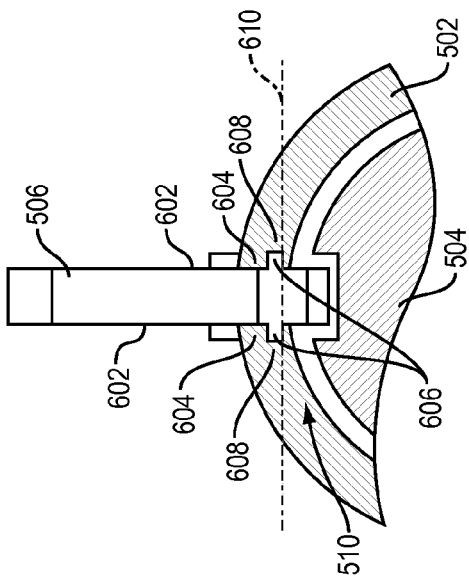
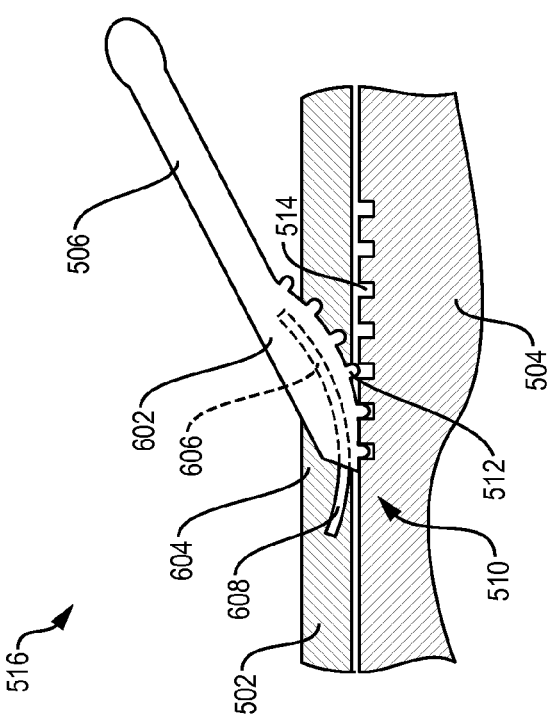

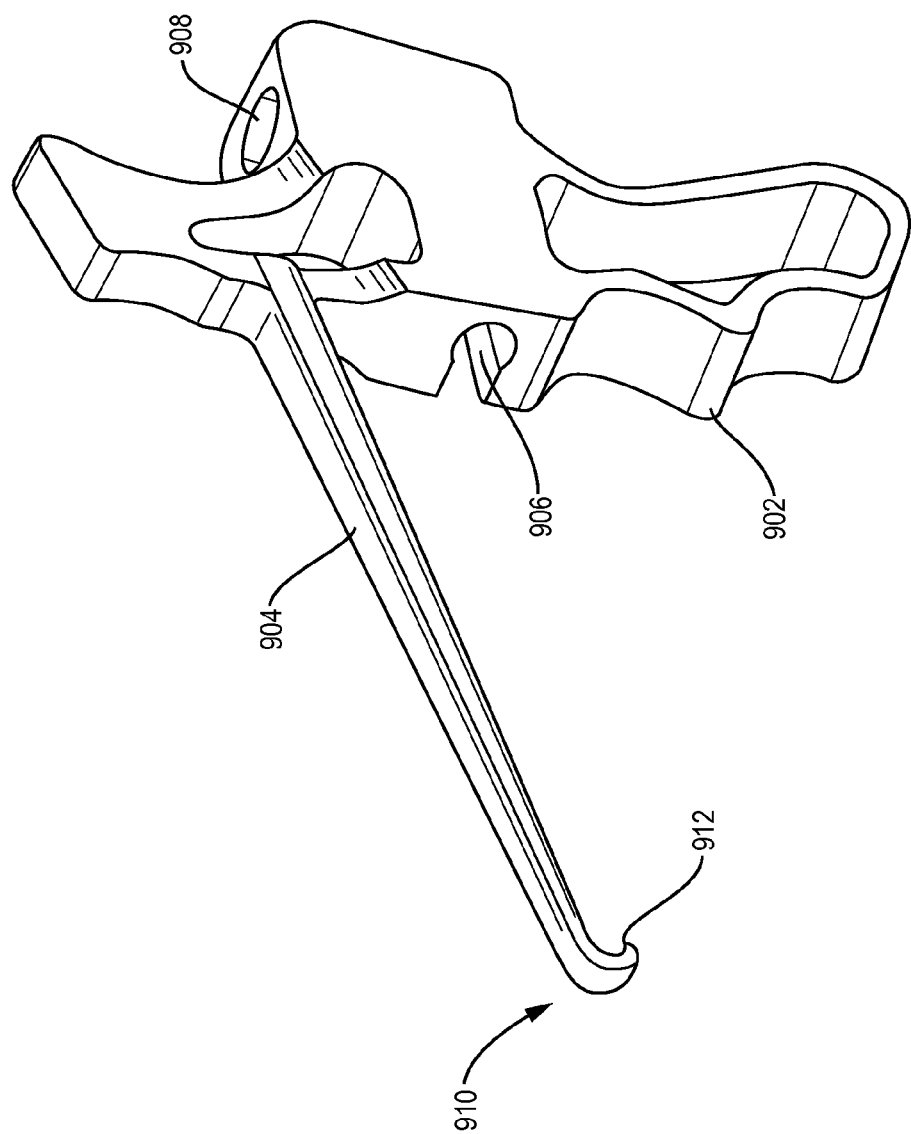

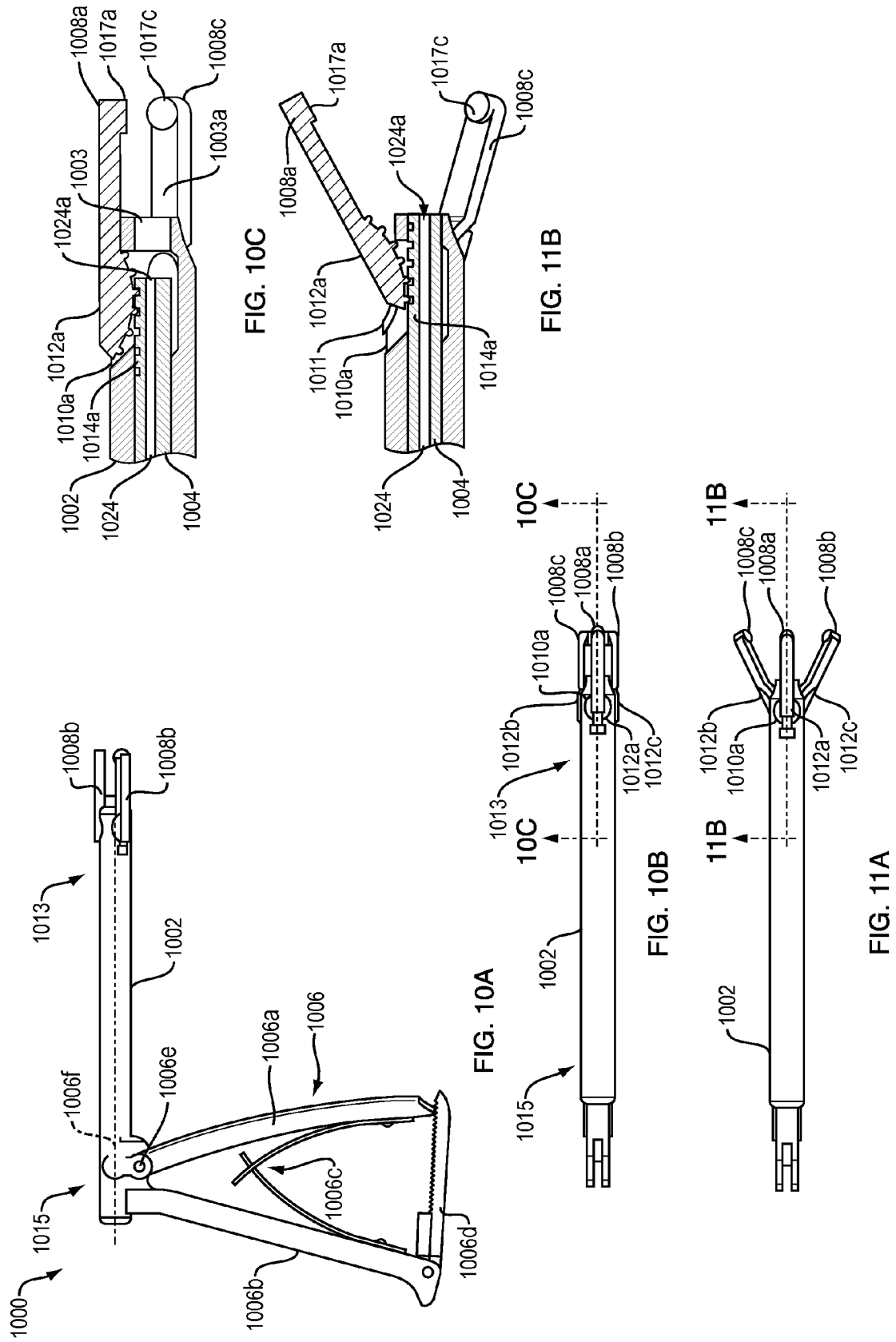

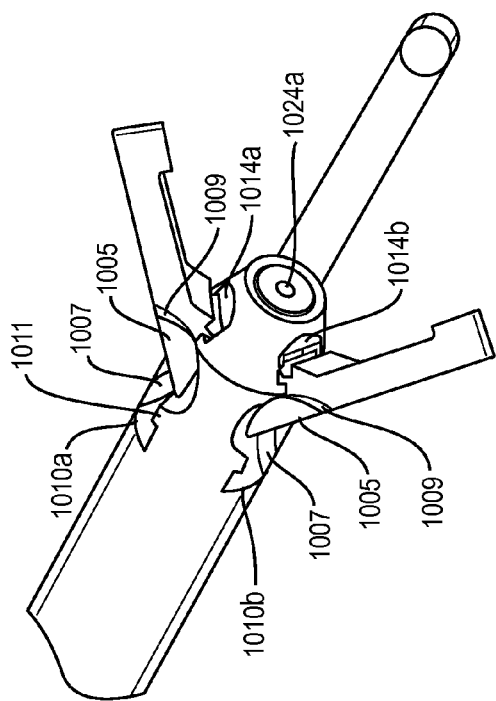
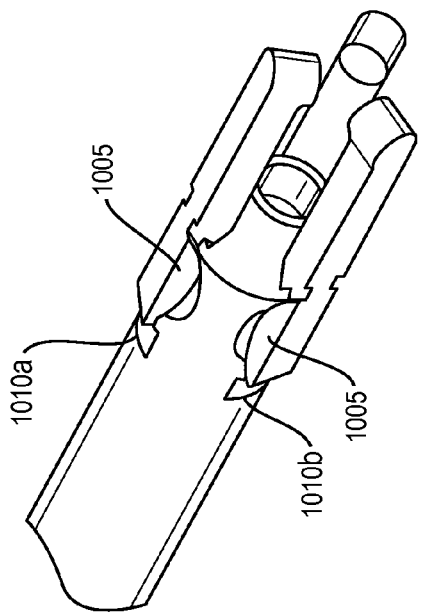
FIG11D
FIG10D

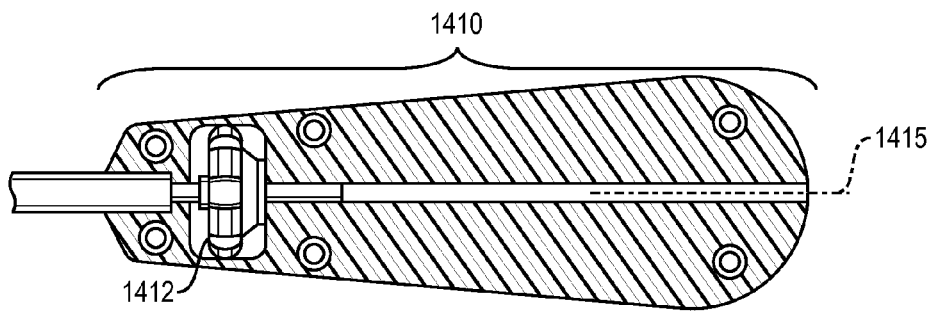
FIG. 14A
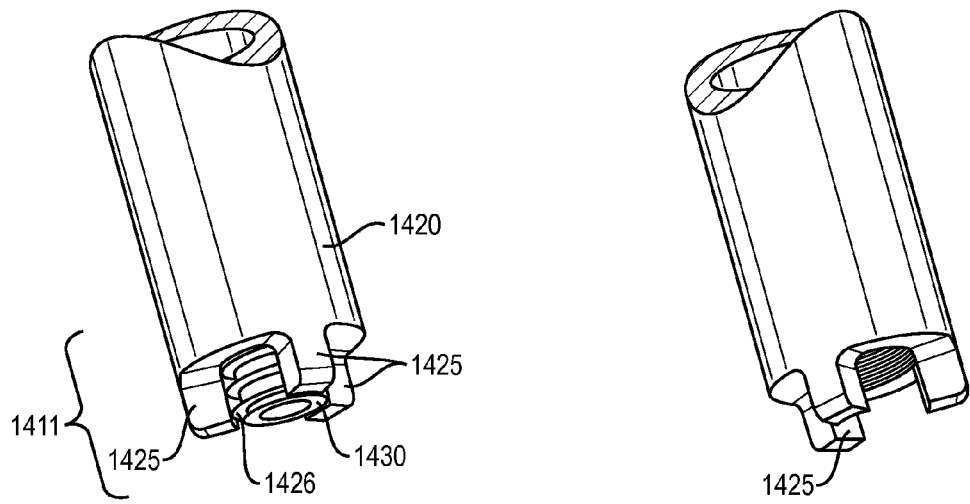
FIG. 14B
FIG. 14C
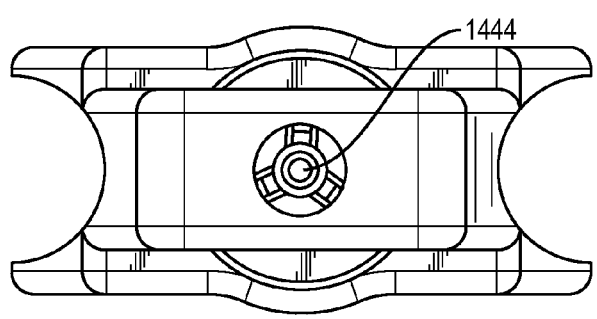
FIG. 14D

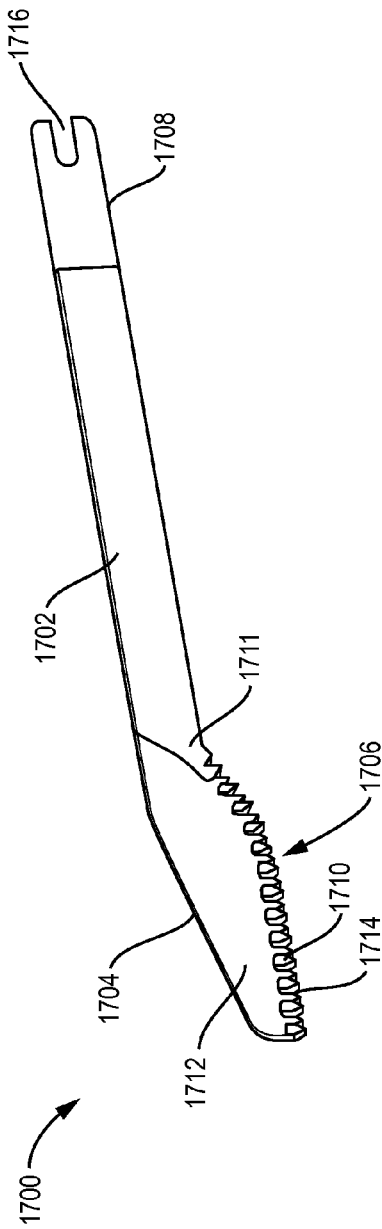
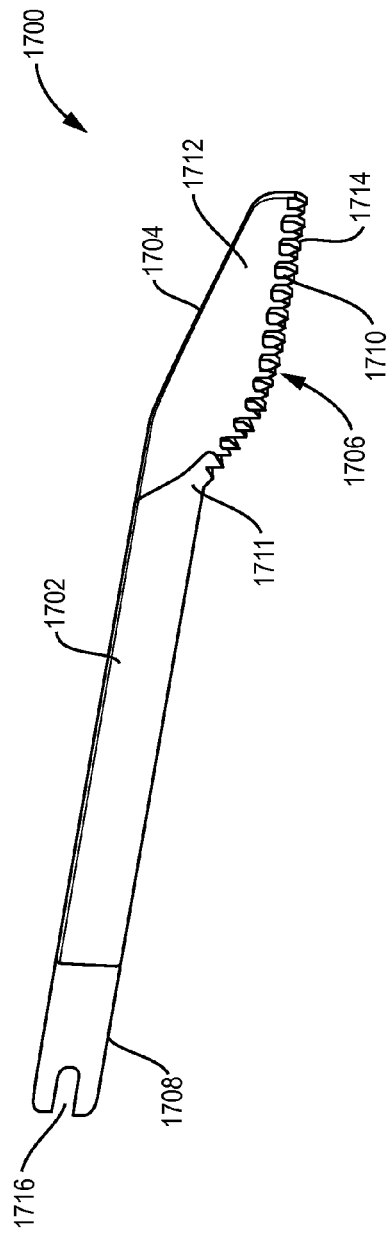
FIG. 17A
FIG. 17B

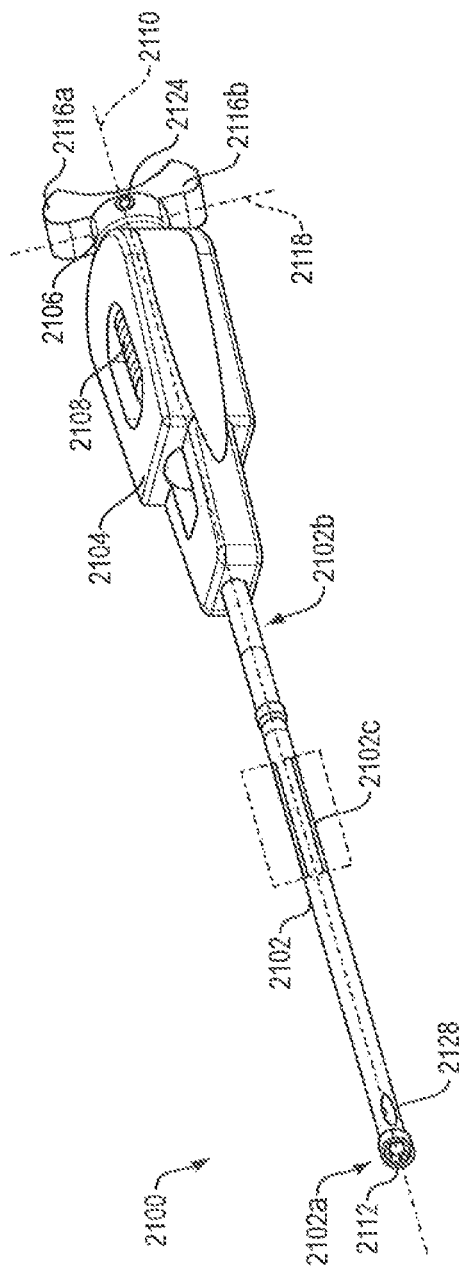
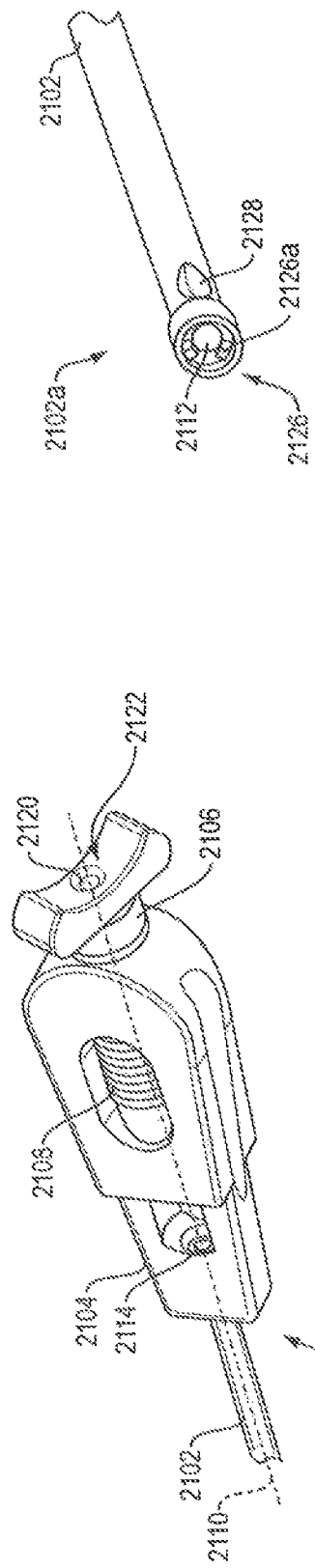
FIG. 21A
FIG. 21B
FIG. 21C

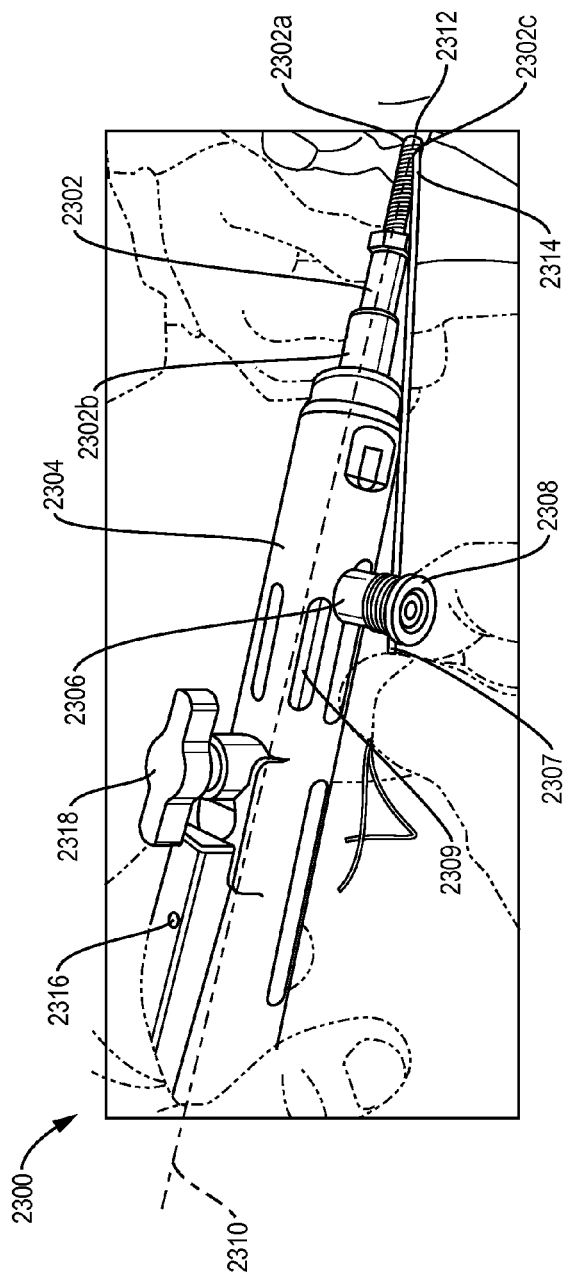
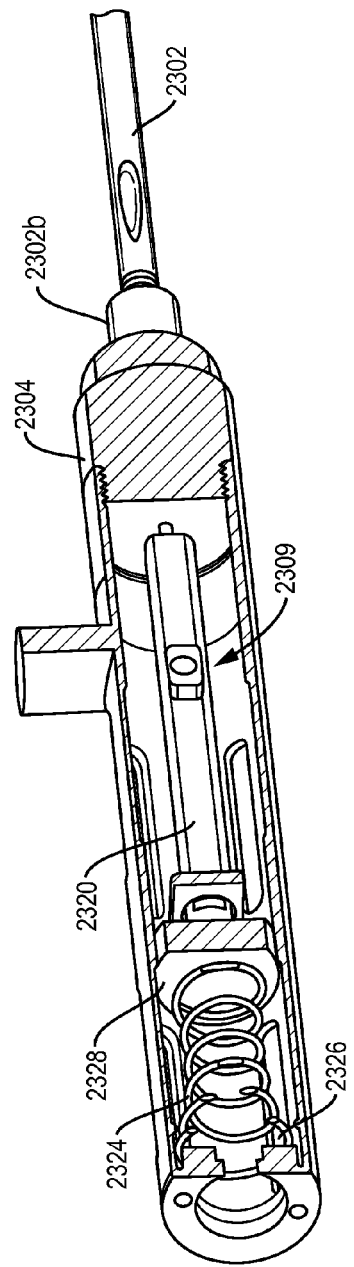
FIG. 23A
FIG. 23B

SURGICAL FASTENING

CROSS-REFERENCE TO RELATED APPLICATION(S)

This application claims the benefit of U.S. Provisional Application Number Application No. 61/794,212, entitled "Surgical Fastening," filed on Mar. 15, 2013, the entirety of which is incorporated herein by reference.

BACKGROUND

Joint and ligament injuries are common. One type of injury includes bone loss of the glenoid, resulting in anterior shoulder instability. One procedure to address this issue involves transfer of a resected portion of the coracoid to the area of glenoid bone loss to replace the missing bone. In some cases, the coracoid is transferred with its conjoined tendon. The coracoid and tendon increase stability, which may prevent dislocations.

SUMMARY

In an embodiment, a tissue spreader is provided, including a first member and a second member. The first member includes a first distal end, a first proximal end, a first shaft portion connecting the first distal end and the first proximal end, the first shaft portion defining a lumen, and a first paddle portion located at the first distal end. The first paddle portion includes a first spreading member with a first spreading surface that has a longitudinal axis parallel to, but offset from, a central, longitudinal axis of the first shaft portion by a first distance greater than a radius of the first shaft portion. The second member includes a second distal end, a second proximal end, a second shaft portion connecting the second distal end and the second proximal end and disposed within the lumen of the first shaft portion, and a second paddle portion located at the distal end. The second paddle portion includes a second spreading member with a second spreading surface that has a longitudinal axis that is parallel to but offset from the central, longitudinal axis of the first shaft portion by a second distance greater than a radius of the first shaft portion. The first member and the second member are configured to rotate relative to each other about the central longitudinal axis between an open position and a closed position, where the first spreading surface and the second spreading surface are separated by the first distance plus the second distance when the first member and the second member are in the open position.

In other embodiments, the tissue spreader may include one or more of the following, in any combination. The first spreading surface and the second spreading surface are substantially diametrically opposed relative to the central, longitudinal axis of the first shaft portion when the first member and the second member are in the open position. The first spreading surface and the second spreading surface are substantially overlapped when the first member and the second member are in the closed position. The second spreading member is nested in the first spreading member when the first member and the second member are in the closed position. The second shaft portion defines a second lumen concentric with the lumen defined by the first shaft portion. The tissue spreader further including a handle coupled to the first and second proximal ends such that rotation of the handle causes rotation of the second member relative to the first member. The tissue spreader further including a locking mechanism to stabilize the first and second members in the open position or the closed position. The locking mechanism including first and second saddle shaped notches on opposite sides of the first shaft portion and a post located on the second shaft portion, where the post rests in the first notch when the first and second members are in the open position and rests in the second notch when the first and second members are in the closed position. The locking mechanism including a spring that biases the second member along the central longitudinal axis of the first shaft portion towards the first proximal end. The first and second spreading members including lumens that align to form a single passage through the first and second spreading members when the first and second members are in the closed position. The first member including a first slot from the first distal end to the first proximal end, the second member including a second slot from the second distal end to the second proximal end, and the first and second members being configured such that the first and second slots are aligned when the first member and the second member are in the open position and the first and second slots are not aligned when the first member and the second member are in the second position.

In an embodiment, a tissue spreader is provided, including a body member, an actuating member, at least one arm, and at least one jaw member. The body member defines a first lumen. The actuating member is disposed within the first lumen and defines a second lumen that extends from a proximal end of the actuating member to a distal end of the actuating member, where the actuating member is configured to move relative to the body member. The at least one arm is coupled to the body member and the actuating member. The at least one jaw member is coupled to the arm. The arm is further coupled to the body member and the actuating member such that movement of the actuating member relative to the body member causes the arm to move the jaw member away from the body member while maintaining a longitudinal axis of the jaw member parallel to a central, longitudinal axis of the tissue spreader.

In other embodiments, the tissue spreader may include one or more of the following, in any combination. The at least one arm includes a first arm and a second arm, the first arm and the second arm coupled to the body member and the actuating member, the jaw member is coupled to the first arm and the second arm, and the first arm and the second arm are coupled to the body member and the actuating member such that movement of the actuating member relative to the body member causes the first arm and the second arm to move the jaw member away from the body member while maintaining a longitudinal axis of the jaw member parallel to a central, longitudinal axis of the tissue spreader. The at least one arm includes a first arm, a second arm, a third arm, and a fourth arm, where the first arm, the second arm, the third arm and the fourth arm are coupled to the body member and the actuating member. The at least one jaw member includes a first jaw member that is coupled to the first arm and the second arm and a second jaw member that is coupled to the third arm and the fourth arm. The first arm and the second arm are coupled to the body member and the actuating member such that movement of the actuating member relative to the body member causes the first arm and the second arm to move the first jaw member away from the body member while maintaining a longitudinal axis of the first jaw member parallel to a central, longitudinal axis of the tissue spreader, and the third arm and the fourth arm are coupled to the body member and the actuating member such that movement of the actuating member relative to the body member causes the third arm and the fourth arm to move the second jaw member away from the body member while maintaining a longitudinal axis of the second jaw member parallel to a central, longitudinal axis of the tissue spreader. The first arm, the second arm, the third arm, and the fourth arm are coupled to the body member and the actuating member such that movement of the actuating member relative to the body member causes the first arm and the second arm to move the first jaw member away from the body member in a first direction and causes the third arm and the fourth arm to move the second jaw member away from the body member in a second direction, the second direction being opposite to the first direction. A first end of the arm is coupled to the jaw member, a second end of the arm includes a first geared portion, the second end of the arm and the body member being coupled to one another by one or more arcuate grooves or flanges, and the actuating member includes a second geared portion that mates with the first gear portion such that movement of the actuating member results in movement of the second end of the arm along the grove or flange, which causes the arm to pivot relative to the central, longitudinal axis of the tissue spreader. The second lumen terminates in an opening at the proximal end of the actuating member. The actuating member is configured to move along the central, longitudinal axis of the tissue spreader.

In an embodiment, a bone contouring device is provided, including a body portion and a head portion. The head portion is coupled to the body portion and includes a first surface, a second surface opposite the first surface and defining an opening, sidewalls connecting the first and second surfaces, a plurality of teeth and gaps positioned between the teeth, and a channel that extends from the opening to the plurality of teeth and gaps along an axis perpendicular to a longitudinal axis of the head portion. At least one of the opening, the channel, the teeth, and the gaps are dimensioned to permit passage of bone fragments through at least one of the gaps, the channel, and the opening.

In other embodiments, the bone contouring device may include one or more of the following, in any combination. A handpiece connection portion coupled to the body portion at an end opposite the head portion, the handpiece connection portion configured to attach to a powered handpiece. The channel extends along the longitudinal axis of the head portion from a cutting surface of a first tooth to and past a cutting surface of a last tooth, the first tooth located at a distal end of the head portion and the last tooth located at a proximal end of the head portion. The head portion is angled upwards relative to the body portion. The head portion is angled downwards relative to the body portion. The head portion is aligned with the body portion such that a longitudinal axis of the head portion forms a straight line with a longitudinal axis of the body portion.

In a further embodiment, a suture tensioning device is provided, including a shaft, a body, and a suture tensioning member. The shaft includes a distal end and a proximal end, the shaft defining a suture lumen that extends from the distal end to the proximal end, the suture lumen configured to have suture passed from the distal end to the proximal end and out of an opening at the proximal end. The body is coupled to the proximal end of the shaft. The suture tensioning member is coupled to the body and is configured to be coupled to the suture passed out the opening at the proximal end of the shaft and, when actuated, to exert a force on the suture in a direction away from the distal end of the shaft.

In other embodiments, the suture tensioning device may include one or more of the following, in any combination. The suture tensioning member includes a retractable screw member coupled to the body such that rotating the retractable screw member moves the screw member along a central axis of the tensioning device to exert the force on the suture in the direction away from the distal end of the shaft. The retractable screw member includes a distal end and a proximal end and a suture lumen that is arranged coaxial to the suture lumen of the shaft and extends from the distal end to the proximal end, where the suture lumen is further configured to have the suture passed from the distal end of the retractable screw member to the proximal end of the retractable screw member and out of an opening at the proximal end of the retractable screw member and where the retractable screw member includes an outer feature configured to be coupled to the suture passed out the opening at the proximal end of the retractable screw member. The suture tensioning member includes a tensioner barrel configured to be coupled to the suture passed out the opening at the proximal end of the shaft and a ratchet mechanism configured to move the tensioner barrel away from the distal end of the shaft along an axis parallel to a central axis of the tensioning device to exert the force on the suture in the direction away from the distal end of the shaft. The suture tensioning member includes a tensioning bar coupled to the body such that a longitudinal axis of the tensioning bar is oriented perpendicular to a central axis of the tensioning device, the tensioning bar configured to be coupled to the suture such that rotation of the tensioning bar exerts the force on the suture in the direction away from the distal end of the shaft. The distal end of the shaft is configured to engage the second fastener.

In an embodiment, a drill guide is provided, including a body, a plurality of ports, a shaft, and a plurality of jaw members. The body is elongate and cannulated, having a distal end and a proximal end and defining a lumen extending along a longitudinal axis there-between, the body further including. The plurality of ports are formed in the distal end. The shaft is elongate and cannulated, positioned within the lumen and configured to slide within the lumen relative to the drill guide body. The shaft further includes a plurality of geared regions at a distal end, each geared region aligned with a respective one of the plurality of ports. The plurality of jaw members each including a gripping end and a geared end opposite the gripping end. Each of the geared ends are received within a respective port of the drill guide body and mesh with the geared region aligned therewith. Movement of the shaft along the longitudinal axis in a second direction urges movement of each of the plurality of jaw members into a closed position, where the gripping ends of each jaw member are distanced from the drill guide body by a first distance. Movement of the shaft along the longitudinal axis in a first direction urges movement of each of the plurality of jaw members into an open position, where the gripping ends of each jaw member are distanced from the drill guide body by a second distance, greater than the first distance.

In other embodiments, the drill guide may include one or more of the following, in any combination. A pair of arcuate flanges formed upon opposing sidewalls of each of the plurality of ports and a pair of arcuate grooves formed on opposing lateral surfaces of the geared end of each of the plurality of jaw members, where the arcuate flanges configured to slide within the arcuate grooves allowing their respective jaw member to pivot relative to the longitudinal axis of the drill guide body and where, upon axial movement of the shaft relative to the drill guide body, the arcuate flanges slide within the arcuate grooves and urge their respective jaw member to pivot between the open and closed positions. Movement of the shaft towards the distal end of the anchor body results in pivoting of the gripping ends away from the drill guide body to the open position and movement of the shaft towards the proximal end of the anchor body results in pivoting of the gripping ends towards the drill guide body to the closed position. A handle coupled to the drill guide body and the shaft, the handle including a first elongate handle member and a second elongate handle member, where a first end of the first handle is coupled to the proximal end of the drill guide body, where a first end of the second handle is coupled to the proximal end of the drill guide body, where the first end of the second handle is further coupled to the proximal end of the shaft at a pivot point, and where pivoting the second handle member about the pivot point in a first rotational direction urges the shaft in a first axial direction and pivoting the second handle member about the pivot point in a second rotational direction moves the shaft in a second axial direction. The first rotational direction is towards the first handle member and the first axial direction is towards the distal end of the drill guide body. The drill guide further including a biasing mechanism in communication with the handle, where the second handle member is biased towards the second rotational direction. The drill guide further including a locking mechanism moveable between an engaged position and a disengaged position, where, in the engaged position, the locking mechanism permits pivoting of the second handle in the first rotational direction and inhibits pivoting of the second handle in the second rotational direction.

In an embodiment, a suture construct is provided, including a surgical fastener and a continuous suture loop. The surgical fastener includes a body and a post. The body is generally circular, having opposed first and second surfaces, where the first surface is convex and the second surface is concave. A pair of first holes are formed within the body, extending from the convex first surface to the concave second surface. The post includes a first end and a second end, where the first end of the post is coupled to the concave second surface and extending along a longitudinal axis. A second hole is formed in the post, the second hole extending transverse to the longitudinal axis. The continuous suture loop is routed through either the pair of first holes or the second hole such that two suture loop ends extend from the surgical fastener.

In other embodiments, the surgical fastener may include one or more of the following, in any combination. The post is axially coincident with a portion of the first pair of holes and each of the first pair of holes extend partially through the outer surface of opposing sides of the post, parallel to the longitudinal axis, forming arcuate surfaces on the opposing sides of the post. The post further includes a plurality of chamfered surfaces formed in the second end. The continuous suture loop is routed through one of the first pair of holes, along the first convex surface, and through the other of the first pair of holes. The continuous suture loop is routed through the second hole. The suture construct further including a length of pull suture threaded through the two loop ends.

In an embodiment, a surgical repair method is provided, including preparing a first grafting surface on a glenoid bone, the first grafting surface positioned adjacent an area of bone loss within the glenoid bone, preparing a second grafting surface on an inferior surface of a coracoid process bone, drilling a first passage through the glenoid, drilling a second passage through the coracoid process, passing a guidewire through the first and second passages, wherein the guidewire is passed through the second passage and subsequently through the first passage, resecting a tip of the coracoid process, maneuvering the resected coracoid process along the guidewire such that at least a portion of the first and second grafting surfaces are in contact, and securing the resected coracoid process to the glenoid with two surgical fasteners and a suture extending there-between.

In an embodiment, a surgical repair method may include spreading tissue interposed between an incision made in the patient's shoulder and at least one of the glenoid and the coracoid process with a tissue spreader including a first member, a second member. The first member includes a first distal end a first proximal end, a first shaft portion connecting the first distal end and the first proximal end, the first shaft portion defining a lumen, a first paddle portion located at the first distal end, the first paddle portion including a first spreading member with a first spreading surface that has a longitudinal axis parallel to, but offset from, a central, longitudinal axis of the first shaft portion by a first distance greater than a radius of the first shaft portion. The second member includes a second distal end, a second proximal end, a second shaft portion connecting the second distal end and the second proximal end and disposed within the lumen of the first shaft portion, and a second paddle portion located at the distal end, the second paddle portion including a second spreading member with a second spreading surface that has a longitudinal axis that is parallel to but offset from the central, longitudinal axis of the first shaft portion by a second distance greater than a radius of the first shaft portion. The first member and the second member are configured to rotate relative to each other about the central longitudinal axis between an open position and a closed position, the first spreading surface and the second spreading surface being separated by the first distance plus the second distance when the first member and the second member are in the open position.

In other embodiments of the method, the tissue spreader may include one or more of the following, in any combination. The first spreading surface and the second spreading surface are substantially diametrically opposed relative to the central, longitudinal axis of the first shaft portion when the first member and the second member are in the open position. The first spreading surface and the second spreading surface are substantially overlapped when the first member and the second member are in the closed position. The second spreading member is nested in the first spreading member when the first member and the second member are in the closed position. The second shaft portion defines a second lumen concentric with the lumen defined by the first shaft portion. The tissue spreader further includes a handle coupled to the first and second proximal ends such that rotation of the handle causes rotation of the second member relative to the first member. The tissue spreader further includes a locking mechanism to stabilize the first and second members in the open position or the closed position. The locking mechanism includes first and second saddle shaped notches on opposite sides of the first shaft portion and a post located on the second shaft portion, where the post rests in the first notch when the first and second members are in the open position and rests in the second notch when the first and second members are in the closed position. The locking mechanism includes a spring that biases the second member along the central longitudinal axis of the first shaft portion towards the first proximal end. The first and second spreading members include lumens that align to form a single passage through the first and second spreading members when the first and second members are in the closed position. The first member includes a first slot from the first distal end to the first proximal end, the second member includes a second slot from the second distal end to the second proximal end, and the first and second members are configured such that the first and second slots are aligned when the first member and the second member are in the open position and the first and second slots are not aligned when the first member and the second member are in the second position.

In an alternative embodiment, the method may include spreading tissue interposed between an incision made in the patient's shoulder and at least one of the glenoid and the coracoid process with a tissue spreader, the tissue spreader including a body member, an actuating member, at least one arm, and at least one jaw member. The body member defines a first lumen. The actuating member is disposed within the first lumen and defines a second lumen that extends from a proximal end of the actuating member to a distal end of the actuating member, the actuating member configured to move relative to the body member. The at least one arm is coupled to the body member and the actuating member. The at least one jaw member is coupled to the arm. The arm is coupled to the body member and the actuating member such that movement of the actuating member relative to the body member causes the arm to move the jaw member away from the body member while maintaining a longitudinal axis of the jaw member parallel to a central, longitudinal axis of the tissue spreader.

In other embodiments of the method, the tissue spreader may include one or more of the following, in any combination. The at least one arm includes a first arm and a second arm, the first arm and the second arm coupled to the body member and the actuating member, the jaw member is coupled to the first arm and the second arm, and the first arm and the second arm are coupled to the body member and the actuating member such that movement of the actuating member relative to the body member causes the first arm and the second arm to move the jaw member away from the body member while maintaining a longitudinal axis of the jaw member parallel to a central, longitudinal axis of the tissue spreader. The at least one arm includes a first arm, a second arm, a third arm, and a fourth arm, wherein the first arm, the second arm, the third arm and the fourth arm are coupled to the body member and the actuating member; the at least one jaw member includes a first jaw member that is coupled to the first arm and the second arm and a second jaw member that is coupled to the third arm and the fourth arm; the first arm and the second arm are coupled to the body member and the actuating member such that movement of the actuating member relative to the body member causes the first arm and the second arm to move the first jaw member away from the body member while maintaining a longitudinal axis of the first jaw member parallel to a central, longitudinal axis of the tissue spreader; and the third arm and the fourth arm are coupled to the body member and the actuating member such that movement of the actuating member relative to the body member causes the third arm and the fourth arm to move the second jaw member away from the body member while maintaining a longitudinal axis of the second jaw member parallel to a central, longitudinal axis of the tissue spreader. The first arm, the second arm, the third arm, and the fourth arm are coupled to the body member and the actuating member such that movement of the actuating member relative to the body member causes the first arm and the second arm to move the first jaw member away from the body member in a first direction and causes the third arm and the fourth arm to move the second jaw member away from the body member in a second direction, the second direction being opposite to the first direction. A first end of the arm is coupled to the jaw member; a second end of the arm includes a first geared portion, the second end of the arm and the body member being coupled to one another by one or more arcuate grooves or flanges; and the actuating member includes a second geared portion that mates with the first gear portion such that movement of the actuating member results in movement of the second end of the arm along the grove or flange, which causes the arm to pivot relative to the central, longitudinal axis of the tissue spreader. The second lumen terminates in an opening at the proximal end of the actuating member. The actuating member is configured to move along the central, longitudinal axis of the tissue spreader.

In an embodiment of the method, preparing the first grafting surface may include forming a flat on an anterior surface of the glenoid adjacent the area of bone loss with a bone contouring device to prepare a flat and preparing the second grafting surface includes forming a flat on an inferior surface of the coracoid with the bone contouring device. The bone contouring device includes a body portion and a head portion coupled to the body portion. The head portion includes a first surface; a second surface opposite the first surface and defining an opening; sidewalls connecting the first and second surfaces; a plurality of teeth and gaps positioned between the teeth; and a channel that extends from the opening to the plurality of teeth and gaps along an axis perpendicular to a longitudinal axis of the head portion; where at least one of the opening, the channel, the teeth, and the gaps are dimensioned to permit passage of bone fragments through at least one of the gaps, the channel, and the opening.

In other embodiments of the method, the bone contouring device may include one or more of the following, in any combination. The bone contouring device further includes a handpiece connection portion coupled to the body portion at an end opposite the head portion, the handpiece connection portion configured to attach to a powered handpiece. The channel extends along the longitudinal axis of the head portion from a cutting surface of a first tooth to and past a cutting surface of a last tooth, the first tooth located at a distal end of the head portion and the last tooth located at a proximal end of the head portion. The head portion is angled upwards relative to the body portion. The head portion is angled downwards relative to the body portion. The head portion is aligned with the body portion such that a longitudinal axis of the head portion forms a straight line with a longitudinal axis of the body portion.

In an embodiment of the method, drilling the first passage through the glenoid may include securing a distal end of a glenoid drill guide to the glenoid; and distally advancing a drill bullet through the drill guide, wherein the drill bullet includes a sleeve and a drill; advancing the drill and sleeve from the posterior glenoid surface to the second grafting surface to form the first passageway; and removing the glenoid drill guide, the bullet, and the drill from the patient after forming the first passageway while retaining the sleeve in place.

In an embodiment of the method, drilling the second passage through the coracoid may include grasping a superior surface of the coracoid process with a distal end of a coracoid drill guide; advancing a drill through the coracoid drill guide and the coracoid process, from the superior coracoid surface to the second grafting surface, to form the second passageway; and removing the coracoid drill guide and the drill from the patient after forming the second passageway.

In other embodiments of the method, the coracoid drill guide may include an elongate, cannulated body having a distal end and a proximal end and defining a lumen extending along a longitudinal axis there-between. The body further includes a plurality of ports formed in the distal end; an elongate, cannulated shaft positioned within the lumen and configured to slide within the lumen relative to the drill guide body, the shaft including a plurality of geared regions at a distal end, each geared region aligned with a respective one of the plurality of ports; and a plurality of jaw members, each including a gripping end; and a geared end opposite the gripping end; where each of the geared ends are received within a respective port of the drill guide body and mesh with the geared region aligned therewith; and wherein movement of the shaft along the longitudinal axis in a second direction urges movement of each of the plurality of jaw members into a closed position, where the gripping ends of each jaw member are distanced from the drill guide body by a first distance; and where movement of the shaft along the longitudinal axis in a first direction urges movement of each of the plurality of jaw members into an open position, where the gripping ends of each jaw member are distanced from the drill guide body by a second distance, greater than the first distance.

In further embodiments of the method, the coracoid drill guide may include one or more of the following, in any combination. A pair of arcuate flanges formed upon opposing sidewalls of each of the plurality of ports; and a pair of arcuate grooves formed on opposing lateral surfaces of the geared end of each of the plurality of jaw members; where the arcuate flanges configured to slide within the arcuate grooves allowing their respective jaw member to pivot relative to the longitudinal axis of the drill guide body; and where, upon axial movement of the shaft relative to the drill guide body, the arcuate flanges slide within the arcuate grooves and urge their respective jaw member to pivot between the open and closed positions. Movement of the shaft towards the distal end of the anchor body results in pivoting of the gripping ends away from the drill guide body to the open position and movement of the shaft towards the proximal end of the anchor body results in pivoting of the gripping ends towards the drill guide body to the closed position. A handle coupled to the drill guide body and the shaft, the handle including a first elongate handle member, wherein a first end of the first handle is coupled to the proximal end of the drill guide body; a second elongate handle member, wherein a first end of the second handle is coupled to the proximal end of the drill guide body and wherein the first end of the second handle is further coupled to the proximal end of the shaft at a pivot point; where pivoting the second handle member about the pivot point in a first rotational direction urges the shaft in a first axial direction and pivoting the second handle member about the pivot point in a second rotational direction moves the shaft in a second axial direction. The first rotational direction is towards the first handle member and the first axial direction is towards the distal end of the drill guide body. The coracoid drill guide further includes a biasing mechanism in communication with the handle, wherein the second handle member is biased towards the second rotational direction. The coracoid drill guide further includes a locking mechanism moveable between an engaged position and a disengaged position, wherein, in the engaged position, the locking mechanism permits pivoting of the second handle in the first rotational direction and inhibits pivoting of the second handle in the second rotational direction.

In an embodiment, the method may further include, prior to resecting the tip of the coracoid process, securing the first surgical fastener to the superior coracoid surface by insertion of a portion of the first surgical fastener into the second passageway.

In an embodiment of the method, passing the guidewire through the first and second passages may include advancing a first end of the guidewire through the second passage, from the superior coracoid surface to the second graft surface; guiding the first end of the guidewire towards the sleeve; capturing the first end of the guidewire at a distal end of a capture device extending through the sleeve; and retracting the first end of the guidewire through the sleeve to the posterior surface of the glenoid with the capture device.

In an embodiment of the method, securing the resected coracoid process to the glenoid may include providing a suture construct, including a second surgical fastener, including a generally circular body having opposed first and second surfaces, wherein the first surface is convex and the second surface is concave; a pair of first holes formed within the body, extending from the convex first surface to the concave second surface; a post having a first end and a second end, wherein the first end of the post is coupled to the concave second surface and extending along a longitudinal axis; a second hole formed in the post, the second hole extending transverse to the longitudinal axis; and the suture, where the suture is formed in continuous suture loop; where the continuous suture loop is routed through either the pair of first holes or the second hole of the second fastener such that two suture loop ends extend from the concave second surface; attaching the suture loop ends to the guidewire; and advancing the suture loop through the first and second passageways, from the posterior glenoid surface to the superior coracoid surface, using the guidewire; where the second fastener is secured to the anterior glenoid surface by insertion of a portion of the second fastener into the first passageway during said suture advancement through the first and second passageways; and where the suture loop ends are passed through the first fastener.

In other embodiments of the method, the suture construct may include one or more of the following, in any combination. The post is axially coincident with a portion of the first pair of holes; and each of the first pair of holes extend partially through the outer surface of opposing sides of the post, parallel to the longitudinal axis, forming arcuate surfaces on the opposing sides of the post. The post of the second fastener further includes a plurality of chamfered surfaces formed in the second end. The continuous suture loop is routed through one of the first pair of holes, along the first convex surface, and through the other of the first pair of holes. The continuous suture loop is routed through the second hole.

In an embodiment of the method, securing the resected coracoid process to the glenoid may include forming a half-hitch knot in the suture loop ends extending through the superior coracoid surface and the first fastener; advancing the half-hitch knot into contact with the first fastener; coupling the suture loop ends of the suture to a suture tensioning device; and applying tension to the suture with the suture tensioning device.

In other embodiments of the method, the suture tensioning device includes one or more of the following, in any combination. The suture tensioning device includes a shaft including a distal end and a proximal end, the shaft defining a suture lumen that extends from the distal end to the proximal end, the suture lumen configured to have suture passed from the distal end to the proximal end and out of an opening at the proximal end; a body coupled to the proximal end of the shaft; and a suture tensioning member coupled to the body, the suture tensioning member configured to be coupled to the suture passed out the opening at the proximal end of the shaft and, when actuated, to exert a force on the suture in a direction away from the distal end of the shaft. The suture tensioning member further includes a retractable screw member coupled to the body such that rotating the retractable screw member moves the screw member along a central axis of the tensioning device to exert the force on the suture in the direction away from the distal end of the shaft. The retractable screw member includes a distal end and a proximal end; and a suture lumen that is arranged coaxial to the suture lumen of the shaft and extends from the distal end to the proximal end; where the suture lumen is further configured to have the suture passed from the distal end of the retractable screw member to the proximal end of the retractable screw member and out of an opening at the proximal end of the retractable screw member, and where the retractable screw member includes an outer feature configured to be coupled to the suture passed out the opening at the proximal end of the retractable screw member. The suture tensioning member further includes a tensioner barrel configured to be coupled to the suture passed out the opening at the proximal end of the shaft; and a ratchet mechanism configured to move the tensioner barrel away from the distal end of the shaft along an axis parallel to a central axis of the tensioning device to exert the force on the suture in the direction away from the distal end of the shaft. The suture tensioning member further includes a tensioning bar coupled to the body such that a longitudinal axis of the tensioning bar is oriented perpendicular to a central axis of the tensioning device, the tensioning bar configured to be coupled to the suture such that rotation of the tensioning bar exerts the force on the suture in the direction away from the distal end of the shaft. The distal end of the shaft is configured to engage the second fastener.

In an embodiment, a surgical repair method is provided, including preparing a first grafting surface on a glenoid bone, the first grafting surface positioned adjacent an area of bone loss within the glenoid bone; preparing a second grafting surface on an inferior surface of a coracoid process bone; drilling a first passage through the glenoid; drilling a second passage through the coracoid process; passing a guidewire through the first and second passages, wherein the guidewire is passed through the first passage and subsequently through the second passage; resecting a tip of the coracoid process; maneuvering the resected coracoid process along the guidewire such that at least a portion of the first and second grafting surfaces are in contact; and securing the resected coracoid process to the glenoid with two surgical fasteners and a suture extending there-between.

In an embodiment, the method may include spreading tissue interposed between an incision made in the patient's shoulder and at least one of the glenoid and the coracoid process with a tissue spreader. The tissue spreader includes a first member and a second member. The first member includes a first distal end; a first proximal end; a first shaft portion connecting the first distal end and the first proximal end, the first shaft portion defining a lumen; and a first paddle portion located at the first distal end, the first paddle portion including a first spreading member with a first spreading surface that has a longitudinal axis parallel to, but offset from, a central, longitudinal axis of the first shaft portion by a first distance greater than a radius of the first shaft portion. The second member includes a second distal end; a second proximal end; a second shaft portion connecting the second distal end and the second proximal end and disposed within the lumen of the first shaft portion; and a second paddle portion located at the distal end, the second paddle portion including a second spreading member with a second spreading surface that has a longitudinal axis that is parallel to but offset from the central, longitudinal axis of the first shaft portion by a second distance greater than a radius of the first shaft portion; wherein the first member and the second member are configured to rotate relative to each other about the central longitudinal axis between an open position and a closed position, the first spreading surface and the second spreading surface being separated by the first distance plus the second distance when the first member and the second member are in the open position.

In other embodiments of the method, the tissue spreader may include one or more of the following, in any combination. The first spreading surface and the second spreading surface are substantially diametrically opposed relative to the central, longitudinal axis of the first shaft portion when the first member and the second member are in the open position. The first spreading surface and the second spreading surface are substantially overlapped when the first member and the second member are in the closed position. the second spreading member is nested in the first spreading member when the first member and the second member are in the closed position. The second shaft portion defines a second lumen concentric with the lumen defined by the first shaft portion. The tissue spreader further includes a handle coupled to the first and second proximal ends such that rotation of the handle causes rotation of the second member relative to the first member. The tissue spreader further includes a locking mechanism to stabilize the first and second members in the open position or the closed position. The locking mechanism includes first and second saddle shaped notches on opposite sides of the first shaft portion and a post located on the second shaft portion, wherein the post rests in the first notch when the first and second members are in the open position and rests in the second notch when the first and second members are in the closed position. The locking mechanism includes a spring that biases the second member along the central longitudinal axis of the first shaft portion towards the first proximal end. The first and second spreading members include lumens that align to form a single passage through the first and second spreading members when the first and second members are in the closed position. The first member includes a first slot from the first distal end to the first proximal end; the second member includes a second slot from the second distal end to the second proximal end; and the first and second members are configured such that the first and second slots are aligned when the first member and the second member are in the open position and the first and second slots are not aligned when the first member and the second member are in the second position.

In an embodiment, the method may further include spreading tissue interposed between an incision made in the patient's shoulder and at least one of the glenoid and the coracoid process with an alternative tissue spreader. The tissue spreader includes a body member defining a first lumen; an actuating member disposed within the first lumen and defining a second lumen that extends from a proximal end of the actuating member to a distal end of the actuating member, the actuating member configured to move relative to the body member; and at least one arm coupled to the body member and the actuating member; at least one jaw member coupled to the arm; where the arm is coupled to the body member and the actuating member such that movement of the actuating member relative to the body member causes the arm to move the jaw member away from the body member while maintaining a longitudinal axis of the jaw member parallel to a central, longitudinal axis of the tissue spreader.

In other embodiments of the method, the tissue spreader may include one or more of the following, in any combination. The at least one arm includes a first arm and a second arm, the first arm and the second arm coupled to the body member and the actuating member; the jaw member is coupled to the first arm and the second arm; and the first arm and the second arm are coupled to the body member and the actuating member such that movement of the actuating member relative to the body member causes the first arm and the second arm to move the jaw member away from the body member while maintaining a longitudinal axis of the jaw member parallel to a central, longitudinal axis of the tissue spreader. The at least one arm includes a first arm, a second arm, a third arm, and a fourth arm, wherein the first arm, the second arm, the third arm and the fourth arm are coupled to the body member and the actuating member; the at least one jaw member includes a first jaw member that is coupled to the first arm and the second arm and a second jaw member that is coupled to the third arm and the fourth arm; the first arm and the second arm are coupled to the body member and the actuating member such that movement of the actuating member relative to the body member causes the first arm and the second arm to move the first jaw member away from the body member while maintaining a longitudinal axis of the first jaw member parallel to a central, longitudinal axis of the tissue spreader; and the third arm and the fourth arm are coupled to the body member and the actuating member such that movement of the actuating member relative to the body member causes the third arm and the fourth arm to move the second jaw member away from the body member while maintaining a longitudinal axis of the second jaw member parallel to a central, longitudinal axis of the tissue spreader. The first arm, the second arm, the third arm, and the fourth arm are coupled to the body member and the actuating member such that movement of the actuating member relative to the body member causes the first arm and the second arm to move the first jaw member away from the body member in a first direction and causes the third arm and the fourth arm to move the second jaw member away from the body member in a second direction, the second direction being opposite to the first direction. The first end of the arm is coupled to the jaw member; a second end of the arm includes a first geared portion, the second end of the arm and the body member being coupled to one another by one or more arcuate grooves or flanges; and the actuating member includes a second geared portion that mates with the first gear portion such that movement of the actuating member results in movement of the second end of the arm along the grove or flange, which causes the arm to pivot relative to the central, longitudinal axis of the tissue spreader. The second lumen terminates in an opening at the proximal end of the actuating member. The actuating member is configured to move along the central, longitudinal axis of the tissue spreader.

In an embodiment of the method, preparing the first grafting surface may include forming a flat on an anterior surface of the glenoid adjacent the area of bone loss with a bone contouring device to prepare a flat; and preparing the second grafting surface includes forming a flat on an inferior surface of the coracoid with the bone contouring device. The bone contouring device includes a body portion and a head portion coupled to the body portion. The head portion includes a first surface; a second surface opposite the first surface and defining an opening; sidewalls connecting the first and second surfaces; a plurality of teeth and gaps positioned between the teeth; and a channel that extends from the opening to the plurality of teeth and gaps along an axis perpendicular to a longitudinal axis of the head portion, where at least one of the opening, the channel, the teeth, and the gaps are dimensioned to permit passage of bone fragments through at least one of the gaps, the channel, and the opening.

In other embodiments of the method, the bone contouring device may include one or more of the following, in any combination. The bone contouring device further includes a handpiece connection portion coupled to the body portion at an end opposite the head portion, the handpiece connection portion configured to attach to a powered handpiece. The channel extends along the longitudinal axis of the head portion from a cutting surface of a first tooth to and past a cutting surface of a last tooth, the first tooth located at a distal end of the head portion and the last tooth located at a proximal end of the head portion. The head portion is angled upwards relative to the body portion. The head portion is angled downwards relative to the body portion. The head portion is aligned with the body portion such that a longitudinal axis of the head portion forms a straight line with a longitudinal axis of the body portion.

In an embodiment of the method, drilling the first passage through the glenoid may include securing a distal end of a glenoid drill guide to the glenoid; and distally advancing a drill bullet through the drill guide, wherein the drill bullet includes a sleeve and a drill; advancing the drill and sleeve from the posterior glenoid surface to the second grafting surface to form the first passageway; and removing the glenoid drill guide, the bullet, and the drill from the patient after forming the first passageway while retaining the glenoid sleeve in place.

In an embodiment of the method, drilling the second passage through the coracoid may include grasping a superior surface of the coracoid process with a distal end of a coracoid drill guide; advancing a drill through the coracoid drill guide and the coracoid process, from the superior coracoid surface to the second grafting surface, to form the second passageway; and removing the coracoid drill guide and the drill from the patient after forming the second passageway while retaining the coracoid sleeve in place.

In further embodiments of the method, the coracoid drill guide may include an elongate, cannulated body having a distal end and a proximal end and defining a lumen extending along a longitudinal axis there-between, the body further including a plurality of ports formed in the distal end; an elongate, cannulated shaft positioned within the lumen and configured to slide within the lumen relative to the drill guide body, the shaft including a plurality of geared regions at a distal end, each geared region aligned with a respective one of the plurality of ports; and a plurality of jaw members, each including a gripping end; and a geared end opposite the gripping end; where each of the geared ends are received within a respective port of the drill guide body and mesh with the geared region aligned therewith; and where movement of the shaft along the longitudinal axis in a second direction urges movement of each of the plurality of jaw members into a closed position, where the gripping ends of each jaw member are distanced from the drill guide body by a first distance; and where movement of the shaft along the longitudinal axis in a first direction urges movement of each of the plurality of jaw members into an open position, where the gripping ends of each jaw member are distanced from the drill guide body by a second distance, greater than the first distance.

In embodiments of the method, the coracoid drill guide may include a pair of arcuate flanges formed upon opposing sidewalls of each of the plurality of ports; and a pair of arcuate grooves formed on opposing lateral surfaces of the geared end of each of the plurality of jaw members; where the arcuate flanges configured to slide within the arcuate grooves allowing their respective jaw member to pivot relative to the longitudinal axis of the drill guide body; and where, upon axial movement of the shaft relative to the drill guide body, the arcuate flanges slide within the arcuate grooves and urge their respective jaw member to pivot between the open and closed positions.

In other embodiments of the method, the coracoid drill guide may include one or more of the following, in any combination. Movement of the shaft towards the distal end of the anchor body results in pivoting of the gripping ends away from the drill guide body to the open position and movement of the shaft towards the proximal end of the anchor body results in pivoting of the gripping ends towards the drill guide body to the closed position. The coracoid drill guide further includes a handle coupled to the drill guide body and the shaft, the handle including a first elongate handle member, wherein a first end of the first handle is coupled to the proximal end of the drill guide body; a second elongate handle member, where a first end of the second handle is coupled to the proximal end of the drill guide body and wherein the first end of the second handle is further coupled to the proximal end of the shaft at a pivot point; where pivoting the second handle member about the pivot point in a first rotational direction urges the shaft in a first axial direction and pivoting the second handle member about the pivot point in a second rotational direction moves the shaft in a second axial direction. The first rotational direction is towards the first handle member and the first axial direction is towards the distal end of the drill guide body. The coracoid drill guide further includes a biasing mechanism in communication with the handle, where the second handle member is biased towards the second rotational direction. The coracoid drill guide further includes a locking mechanism moveable between an engaged position and a disengaged position, where, in the engaged position, the locking mechanism permits pivoting of the second handle in the first rotational direction and inhibits pivoting of the second handle in the second rotational direction.

In an embodiment of the method, passing the guidewire through the first and second passages may include advancing a first end of the guidewire through the glenoid sleeve, from the posterior glenoid surface to the first graft surface; guiding the first end of the guidewire towards the coracoid sleeve; capturing the first end of the guidewire at a distal end of a capture device extending through the coracoid sleeve; retracting the first end of the guidewire through the coracoid sleeve to the superior surface of the coracoid with the capture device; and removing the coracoid and glenoid sleeves while retaining the guidewire in place.

In an embodiment of the method, securing the resected coracoid process to the glenoid may include providing a suture construct, including a first surgical fastener and a suture. The first surgical fastener includes a generally circular body having opposed first and second surfaces, where the first surface is convex and the second surface is concave; a pair of first holes formed within the body, extending from the convex first surface to the concave second surface; a post having a first end and a second end, where the first end of the post is coupled to the concave second surface and extending along a longitudinal axis; a second hole formed in the post, the second hole extending transverse to the longitudinal axis; the suture is formed in continuous suture loop, where the continuous suture loop is routed through either the pair of first holes or the second hole of the first fastener such that two suture loop ends extend from the concave second surface; attaching the suture loop ends to the guidewire; and advancing the suture loop through the first and second passageways, from the superior coracoid surface to the anterior glenoid surface, using the guidewire; where the first fastener is secured to the superior coracoid surface by insertion of a portion of the first fastener into the second passageway during said suture advancement through the first and second passageways; and wherein the suture loop ends are passed through anterior glenoid surface.

In further embodiments of the method, the suture construct may include one or more of the following, in any combination. The post is axially coincident with a portion of the first pair of holes; and each of the first pair of holes extend partially through the outer surface of opposing sides of the post, parallel to the longitudinal axis, forming arcuate surfaces on the opposing sides of the post. The post of the first fastener further includes a plurality of chamfered surfaces formed in the second end. The continuous suture loop is routed through one of the first pair of holes, along the first convex surface, and through the other of the first pair of holes. The continuous suture loop is routed through the second hole.

In an embodiment of the method, securing the resected coracoid process to the glenoid may include providing a second fastener, the second fastener including a generally circular body having opposed first and second surfaces, wherein the first surface is convex and the second surface is concave; a pair of holes formed within the body, extending from the convex first surface to the concave second surface; a post having a first end and a second end, wherein the first end of the post is coupled to the concave second surface and extending along a longitudinal axis; passing a first end loop of the suture through one of the pair of holes of the second fastener; passing a second end loop of the suture through the other hole of the pair of holes of the second fastener; forming a half-hitch knot using the suture loop ends extending through the second fastener; advancing the half-hitch knot into contact with the second fastener; and further advancing the half-hitch knot so as to urge the second fastener post into the first passageway.

In an embodiment of the method, securing the resected coracoid process to the glenoid may include coupling the suture ends to a suture tensioning device; and applying tension to the suture with the suture tensioning device.

In embodiments of the method, the suture tensioning device may include one or more of the following, in any combination. A shaft including a distal end and a proximal end, the shaft defining a suture lumen that extends from the distal end to the proximal end, the suture lumen configured to have suture passed from the distal end to the proximal end and out of an opening at the proximal end; a body coupled to the proximal end of the shaft; and a suture tensioning member coupled to the body, the suture tensioning member configured to be coupled to the suture passed out the opening at the proximal end of the shaft and, when actuated, to exert a force on the suture in a direction away from the distal end of the shaft.

In an embodiment, the suture tensioning member may include a retractable screw member coupled to the body such that rotating the retractable screw member moves the screw member along a central axis of the tensioning device to exert the force on the suture in the direction away from the distal end of the shaft. The retractable screw member includes a distal end and a proximal end; and a suture lumen that is arranged coaxial to the suture lumen of the shaft and extends from the distal end to the proximal end; where the suture lumen is further configured to have the suture passed from the distal end of the retractable screw member to the proximal end of the retractable screw member and out of an opening at the proximal end of the retractable screw member, where the retractable screw member includes an outer feature configured to be coupled to the suture passed out the opening at the proximal end of the retractable screw member.

In an embodiment of the method, the suture tensioning member may include a tensioner barrel configured to be coupled to the suture passed out the opening at the proximal end of the shaft; and a ratchet mechanism configured to move the tensioner barrel away from the distal end of the shaft along an axis parallel to a central axis of the tensioning device to exert the force on the suture in the direction away from the distal end of the shaft.

In an embodiment of the method, the suture tensioning member may further include a tensioning bar coupled to the body such that a longitudinal axis of the tensioning bar is oriented perpendicular to a central axis of the tensioning device, the tensioning bar configured to be coupled to the suture such that rotation of the tensioning bar exerts the force on the suture in the direction away from the distal end of the shaft.

In an embodiment of the method, the distal end of the shaft is configured to engage the second fastener.

BRIEF DESCRIPTION OF THE DRAWINGS

The foregoing and other objects, features and advantages will be apparent from the following more particular description of the embodiments, as illustrated in the accompanying drawings in which like reference characters refer to the same parts throughout the different views. The drawings are not necessarily to scale, emphasis instead being placed upon illustrating the principles of the embodiments.

FIG. 6 is a schematic illustration of an embodiment of a pin-less joint of the parallel tissue spreader of FIG. 5;

FIGS. 9A-9D are schematic illustrations of embodiments of a drill guide (e.g., a glenoid drill guide); (A) side view; (B, C) perspective views, distal end; (D) perspective view, proximal end;

FIGS. 10A-10D are schematic illustrations of an embodiment of another drill guide (e.g., a coracoid drill guide) in a closed position; (A); top-down view; (B); side view of jaw members, cutaway; (C) perspective view; (D) perspective view of jaw members;

FIGS. 11A-11D are schematic illustrations of an embodiment of the drill guide of FIGS. 10A-10D in a closed position; (A); side view; (B); top-down view; (C) side view of jaw members, cutaway; (D) perspective view of jaw members;

FIGS. 14A-14D are further schematic illustrations of the self-retaining driver system of FIG. 12; (A) handle portion; (B, C) distal end of external shaft; (D) end-on view;

FIG. 17 is a schematic illustration of an embodiment of a surgical saw;

FIGS. 21A-21C are schematic illustrations of an embodiment of a suture tensioner; (A) perspective view, overall; (B) perspective view, proximal end; (C) perspective view, distal end;

FIGS. 23A-23C illustrate an embodiment of a ratcheting tensioner; (A) photograph, perspective; (B) schematic illustration, cutaway; (C) photo, magnified view of ratcheting mechanism.

DETAILED DESCRIPTION

Figure 1A:
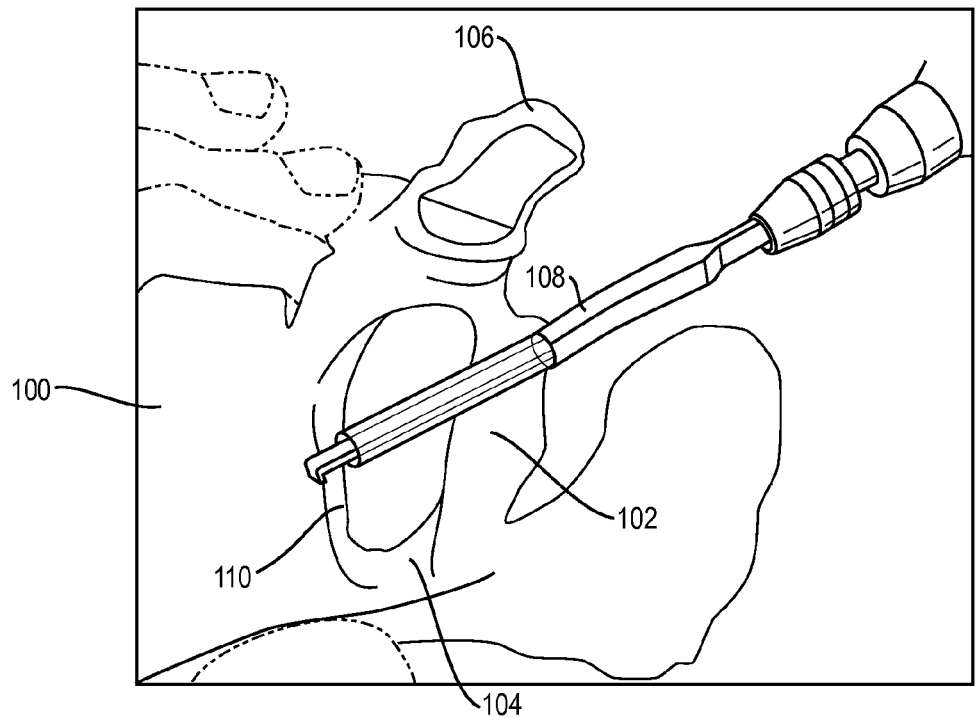
FIGS. 1A-1N illustrate embodiments of a procedure for repairing an area of glenoid bone loss in a patient's shoulder.
Figure 1B:
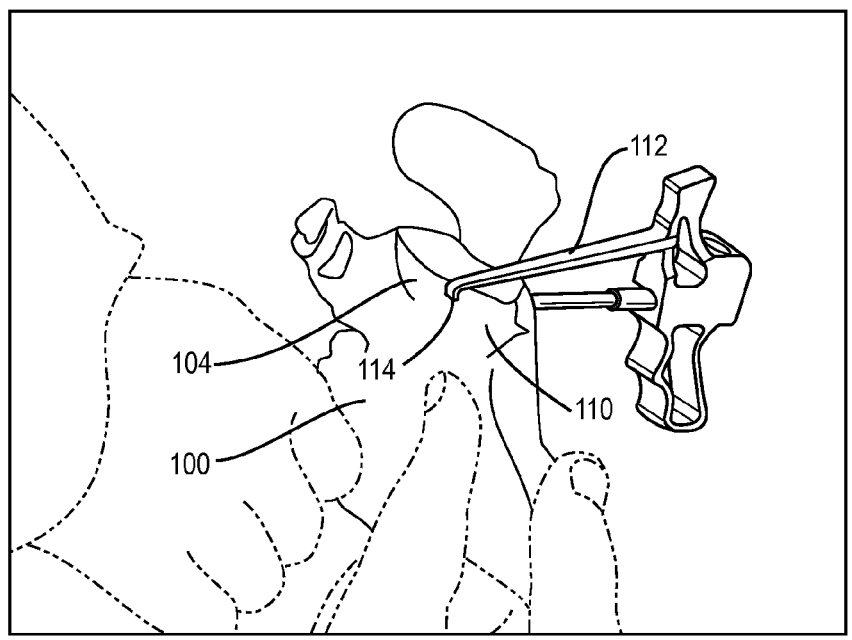
Figure 1C:
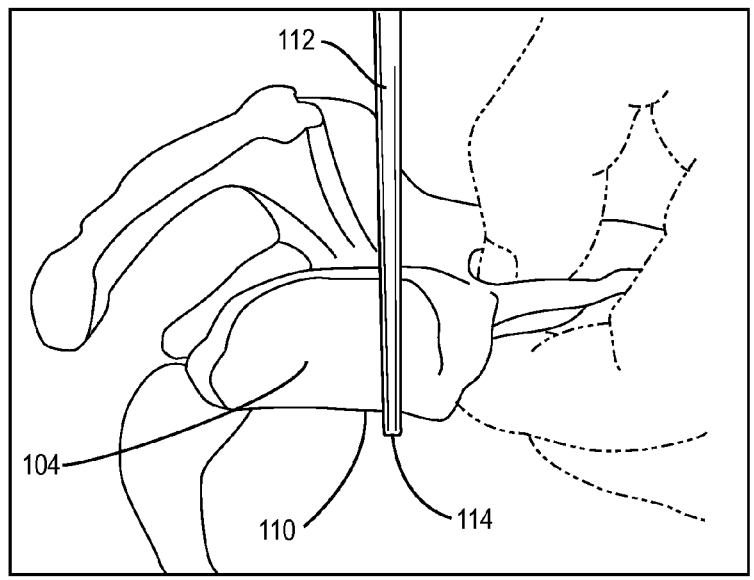
Figure 1D:
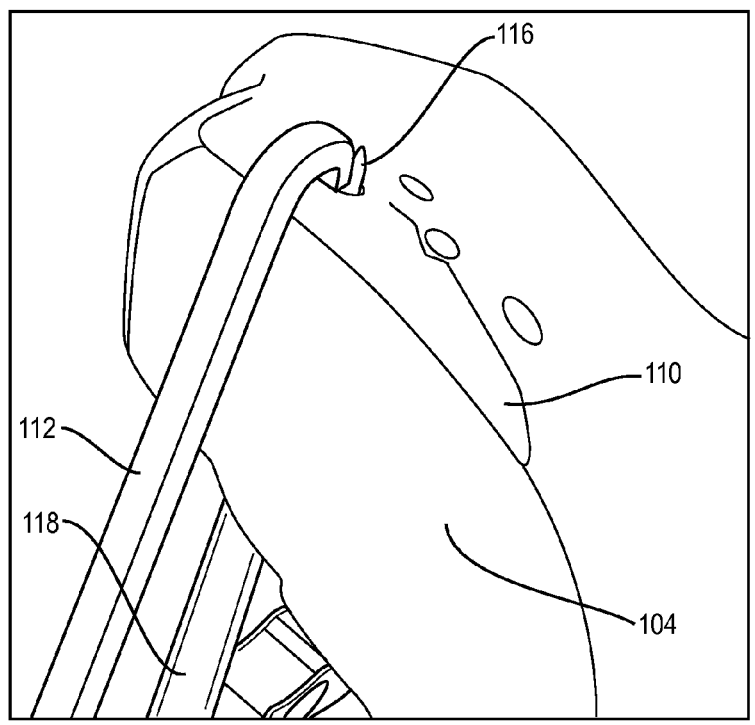
Figure 1E:
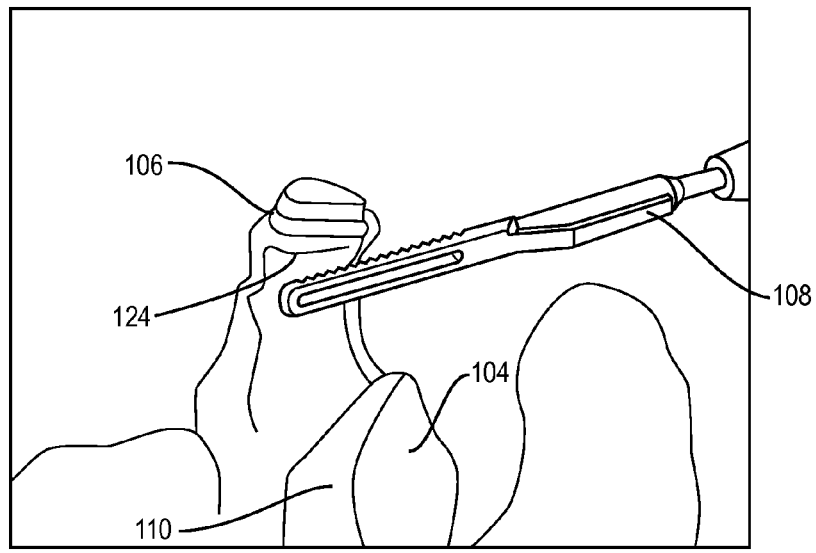
Figure 1F:
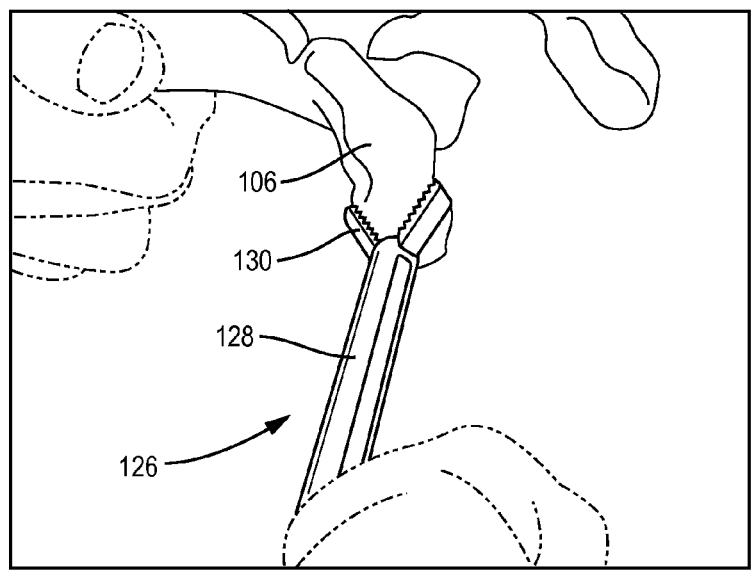
Figure 1G:
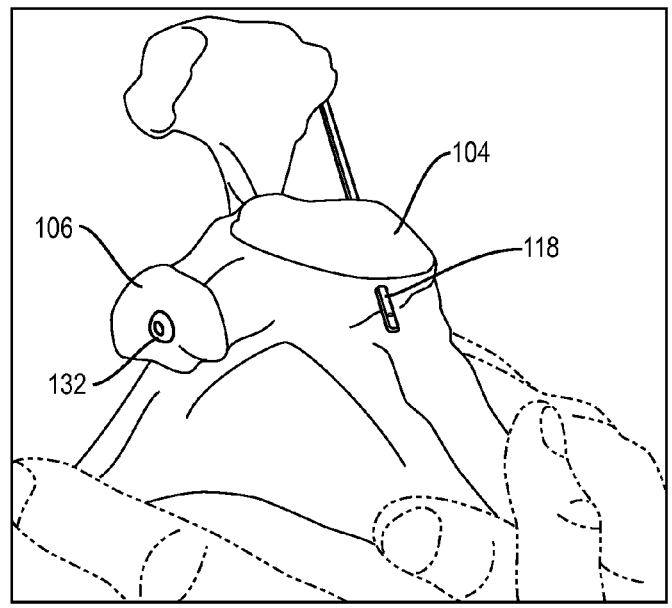
Figure 1H:
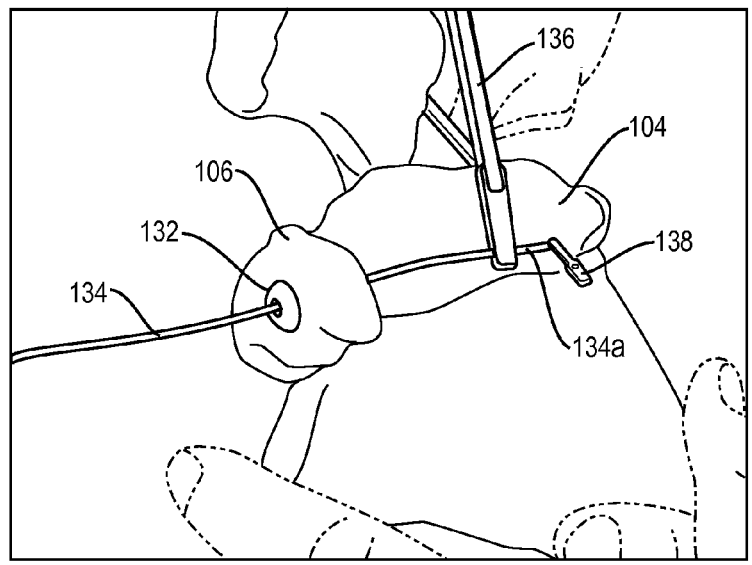
Figure 1I:
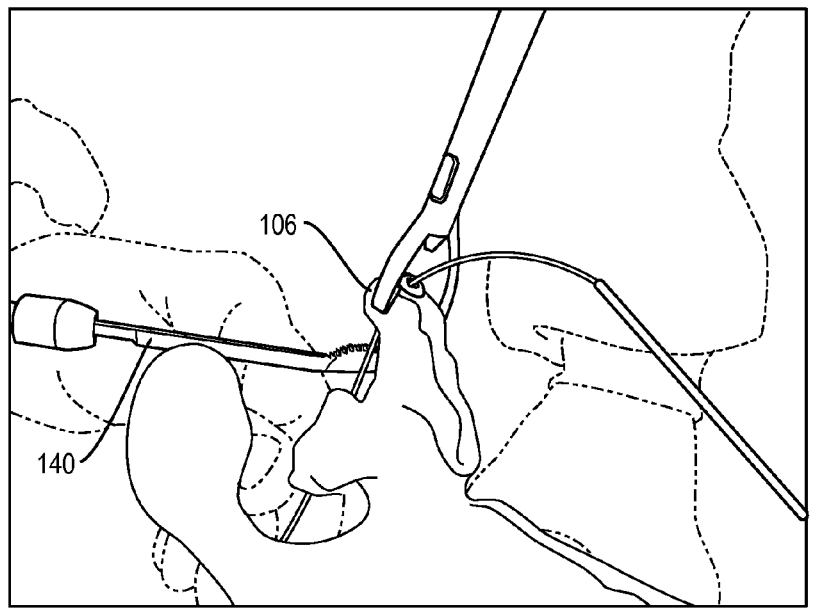
Figure 1J:
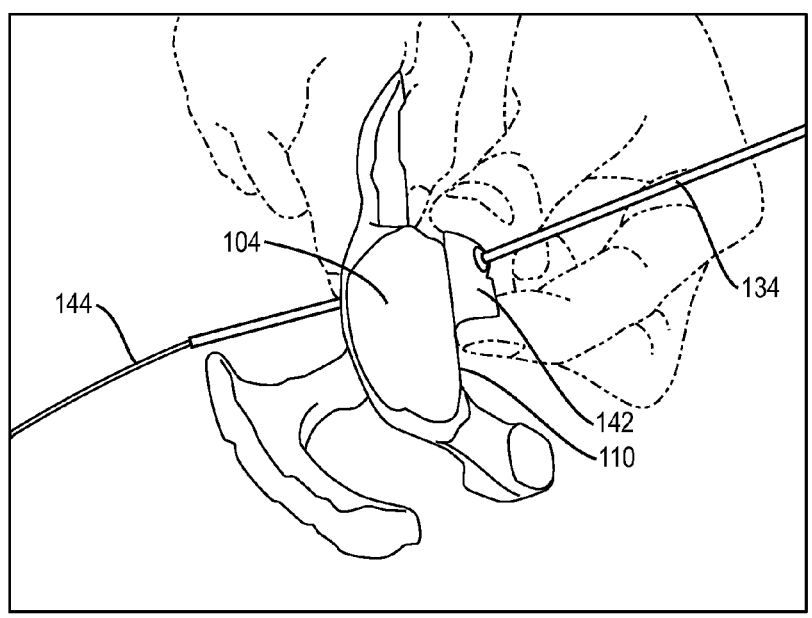
Figure 1K:
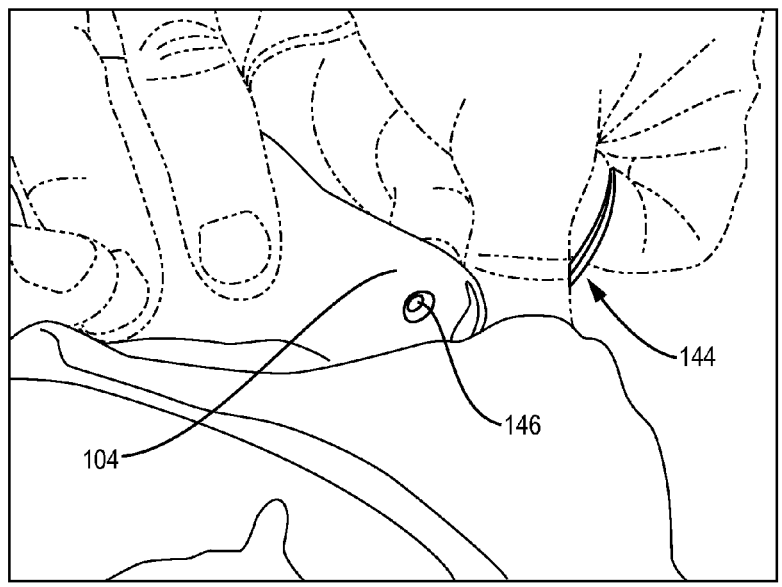
Figure 1L:
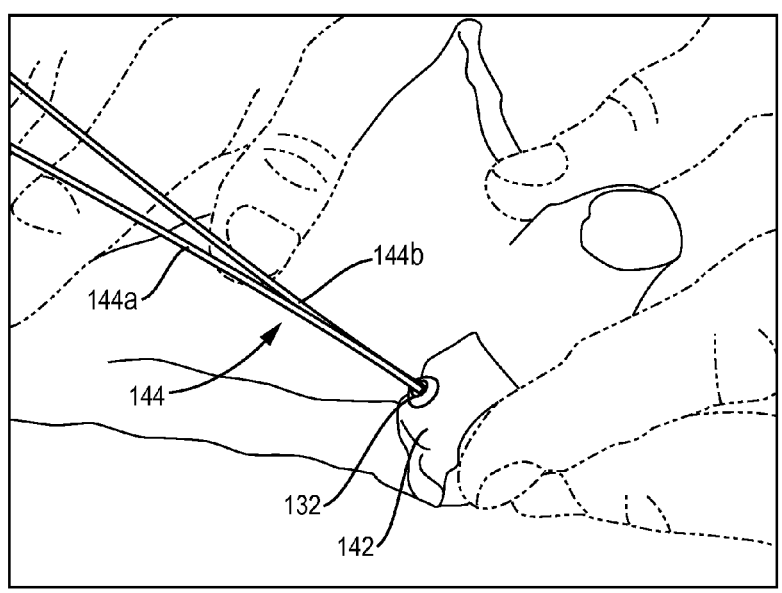
Figure 1M:
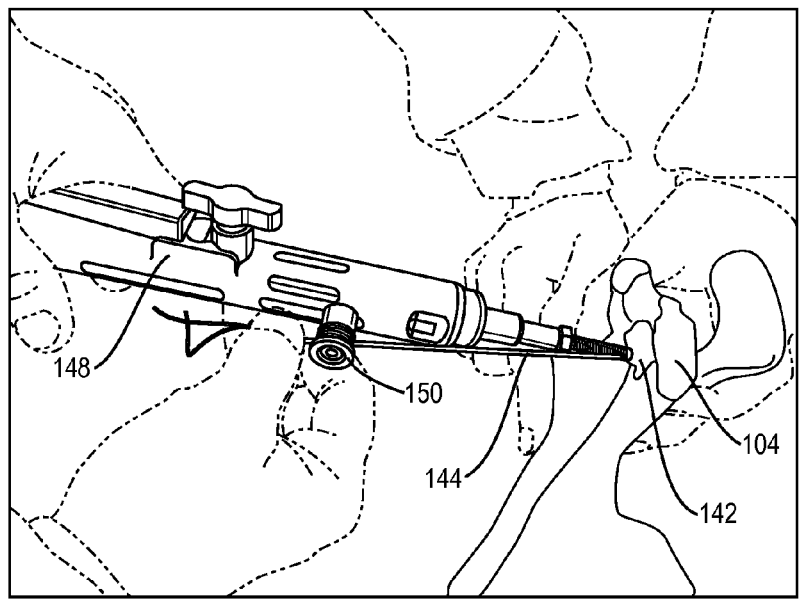
Figure 1N:
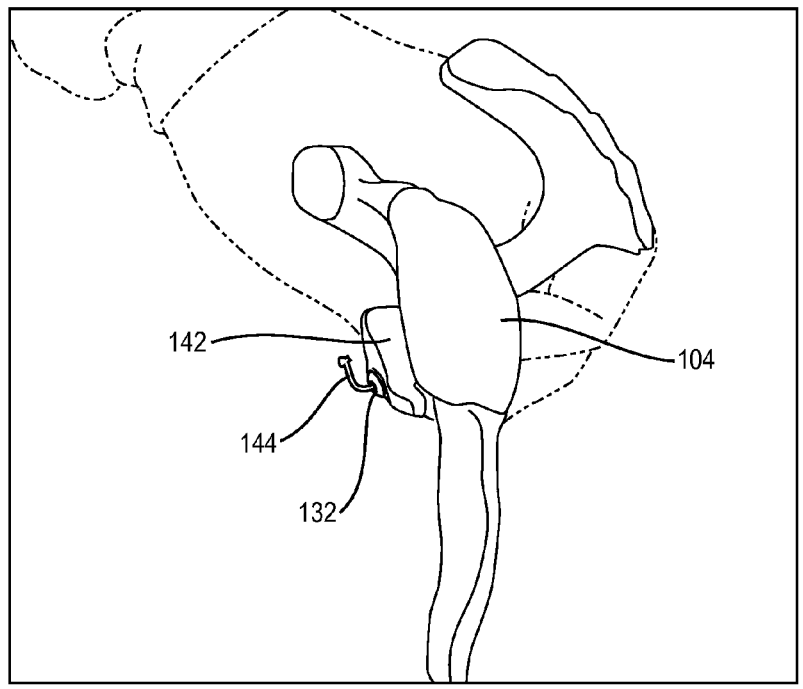

FIGS. 1A-1N illustrate an embodiment of a procedure for repairing an area of glenoid bone loss in a patient's shoulder. FIGS. 1A-1N show a scapula 100 with a glenoid 104, including a region of glenoid bone loss 102, and a coracoid process 106. As discussed in detail below, the procedure includes preparing grafting surfaces on the glenoid 104 near the area of bone loss 102 and on an inferior surface of the coracoid process 106. Passages are then drilled through the glenoid 104 and coracoid process 106. A guidewire is then passed through the passages in the coracoid process 106 and the glenoid 104 to serve as a guide for a portion of the coracoid process 106 which will be grafted onto the glenoid 104 in the area of bone loss 102. The tip of the coracoid process 106 is then resected and maneuvered along the guidewire to bring at least a portion of the prepared grafting surfaces of the glenoid 104 and the coracoid process 106 (see. e.g., FIGS. 1C, 1E, 1J, 110, 124) into contact. Once positioned, the resected tip is secured in place using a suture construct that includes at least two surgical fasteners (e.g., an endobutton and a screw button) and suture extending there-between.

Embodiments of the procedure are described in more detail and illustrated in FIGS. 1A-1N using an artificial scapula 100. However, in practice, the procedure is a minimally invasive arthroscopic procedure. Initially a patient is prepared for surgery and a plurality of anterior and posterior incisions are made in the patient's shoulder. Tissue spreaders (e.g. as shown in FIGS. 2-6) are used to gain access the glenoid and coracoid process by spreading muscle and/or tissue, as necessary, throughout the procedure.

FIG. 1A shows a rasp 108 (e.g. as shown in FIGS. 7 and 8) being used to prepare a grafting surface 110 on the glenoid's 104 anterior surface adjacent to an area of bone loss 102. The rasp 108 is used to form a clean, flat mating surface 110 for the bone graft. In certain embodiments, not shown, the rasp may be attached to a powered reciprocating handle.

Figure 9A:
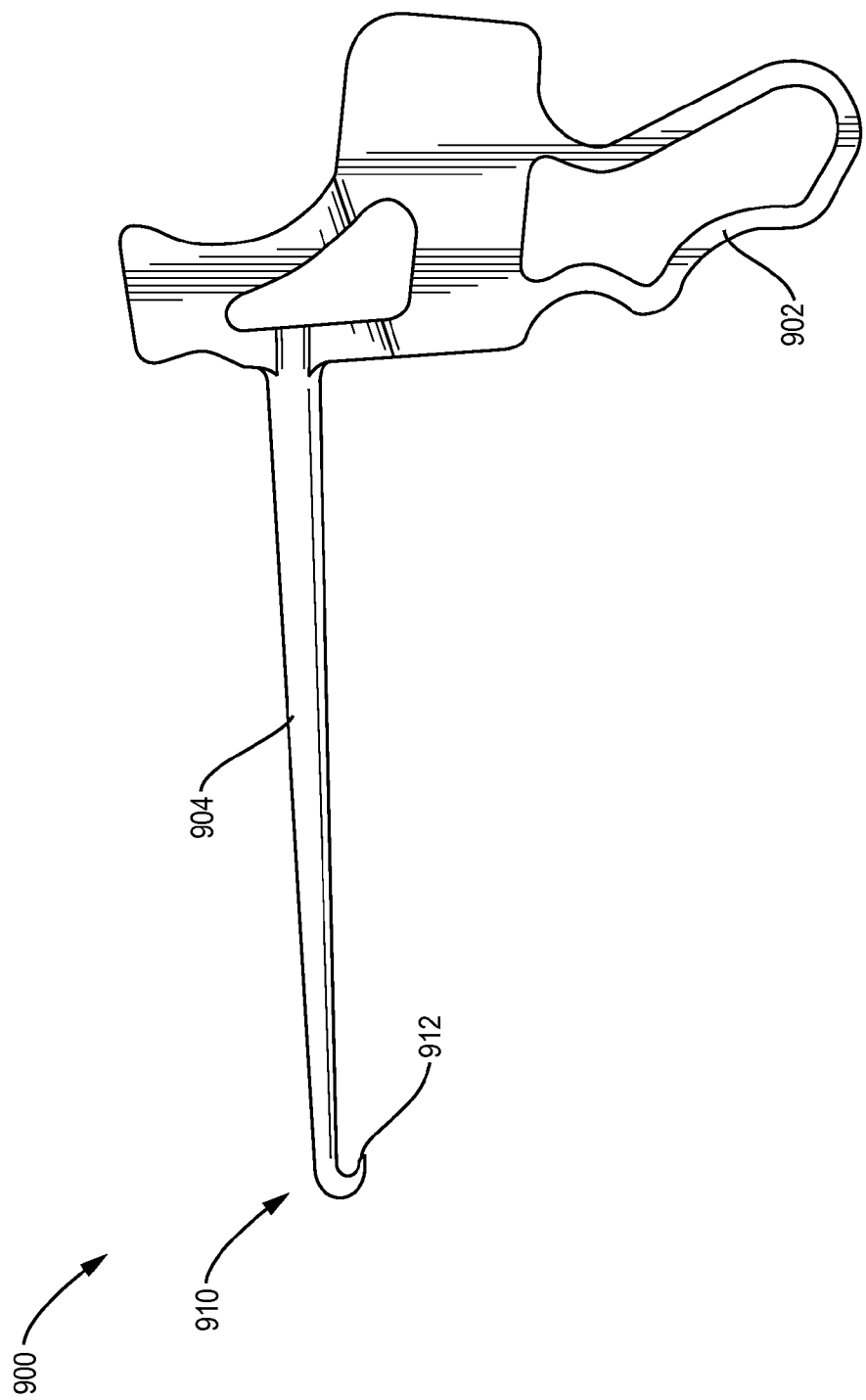
Figure 9B:
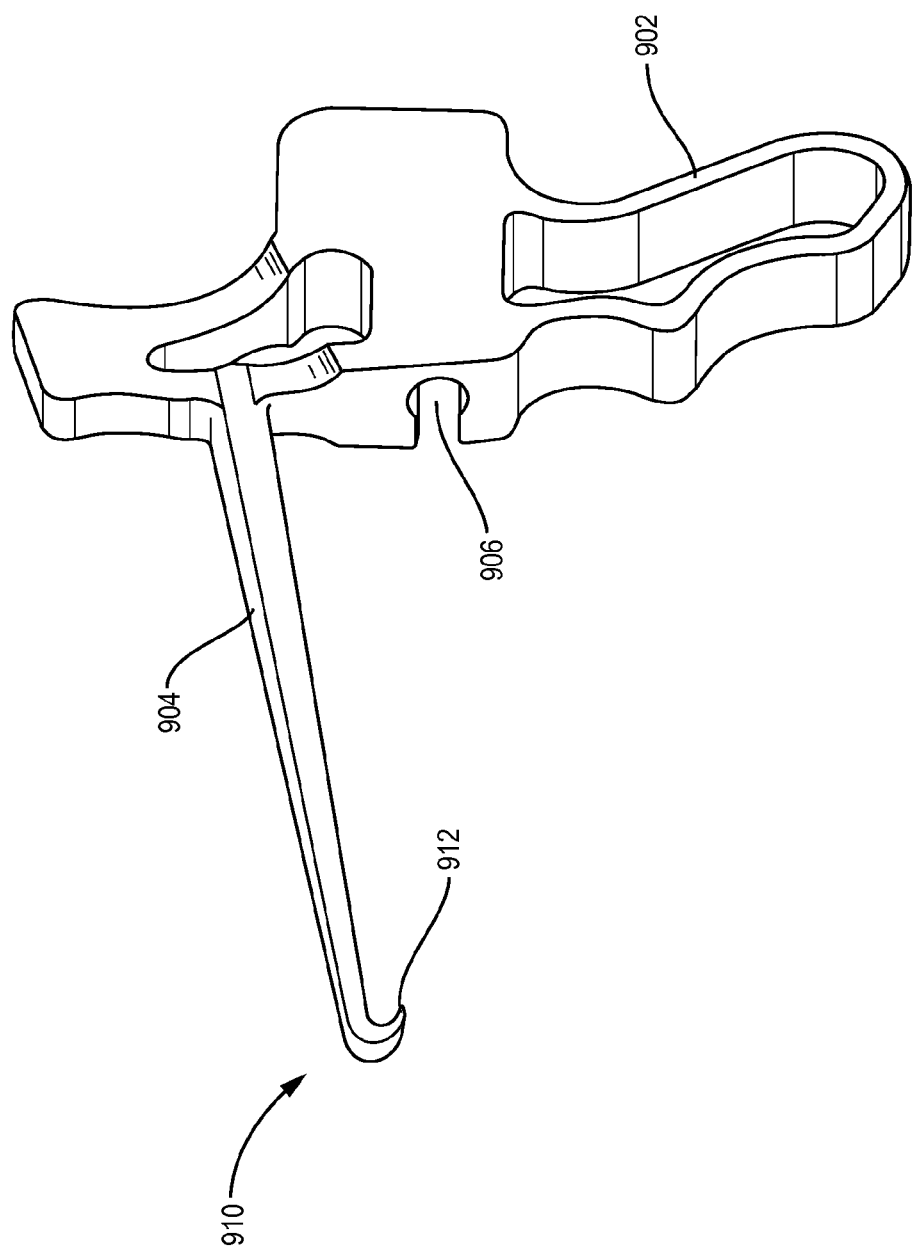
Figure 9D:
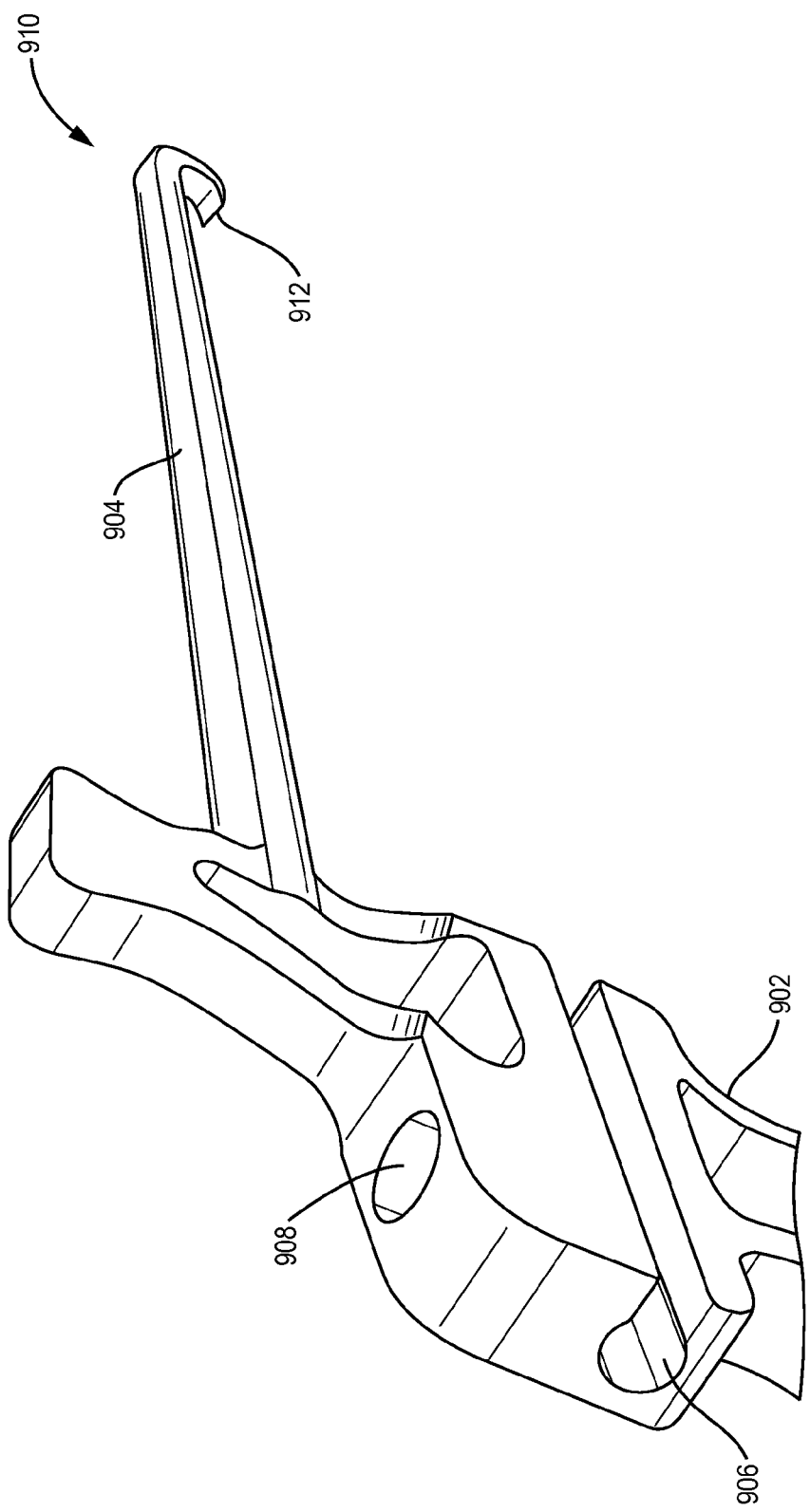

Next, as shown in FIGS. 1B-C, a glenoid drill guide 112 (e.g. as shown in FIG. 9) is positioned on the glenoid 104. The glenoid drill guide 112 is inserted through a posterior portal in the patient's shoulder along a half cannula (not shown) to protect the articular cartilage. An engagement member on the distal end of the glenoid drill guide 112 (e.g., a hook 114) is placed at a selected position on the glenoid 104 (e.g., the "five o'clock" position) and the drill guide 112 is visually aligned perpendicular to the prepared grafting surface 110 (FIG. 1C). Properly aligning the drill guide 112 to the prepared grafting surface 110 helps to prevent misalignment or post-operative graft movement. In certain embodiments, not shown, visual alignment of the drill guide may be accomplished through one of the incisions.

Next, as shown in FIG. 1D, a passage is drilled through the glenoid 104 in a direction from the posterior surface to the prepared graft surface 110 on the glenoid's anterior side. A drill bullet 116 is advanced through the drill guide 112. Inside the bullet 116 is a sleeve 117 and a drill 118. The drill 118 and sleeve 117 are advanced through the glenoid 104 until the sleeve 117 is barely exposed visibly on the anterior surface of the glenoid 104. The drill 118, bullet 116, and guide 112 are then removed, leaving the sleeve 117 in place to provide a cannula for passing a guidewire and suture.

Once the glenoid 104 passage has been drilled through the glenoid 104, cortical bone on the inferior coracoid is removed with the rasp 108 to prepare a flat grafting surface 124 on the coracoid process (FIG. 1E). Removing the cortical bone exposes bleeding, cancellous bone which will be mated to the grafting surface 110 on the anterior 30 glenoid 104.

Figure 11C:
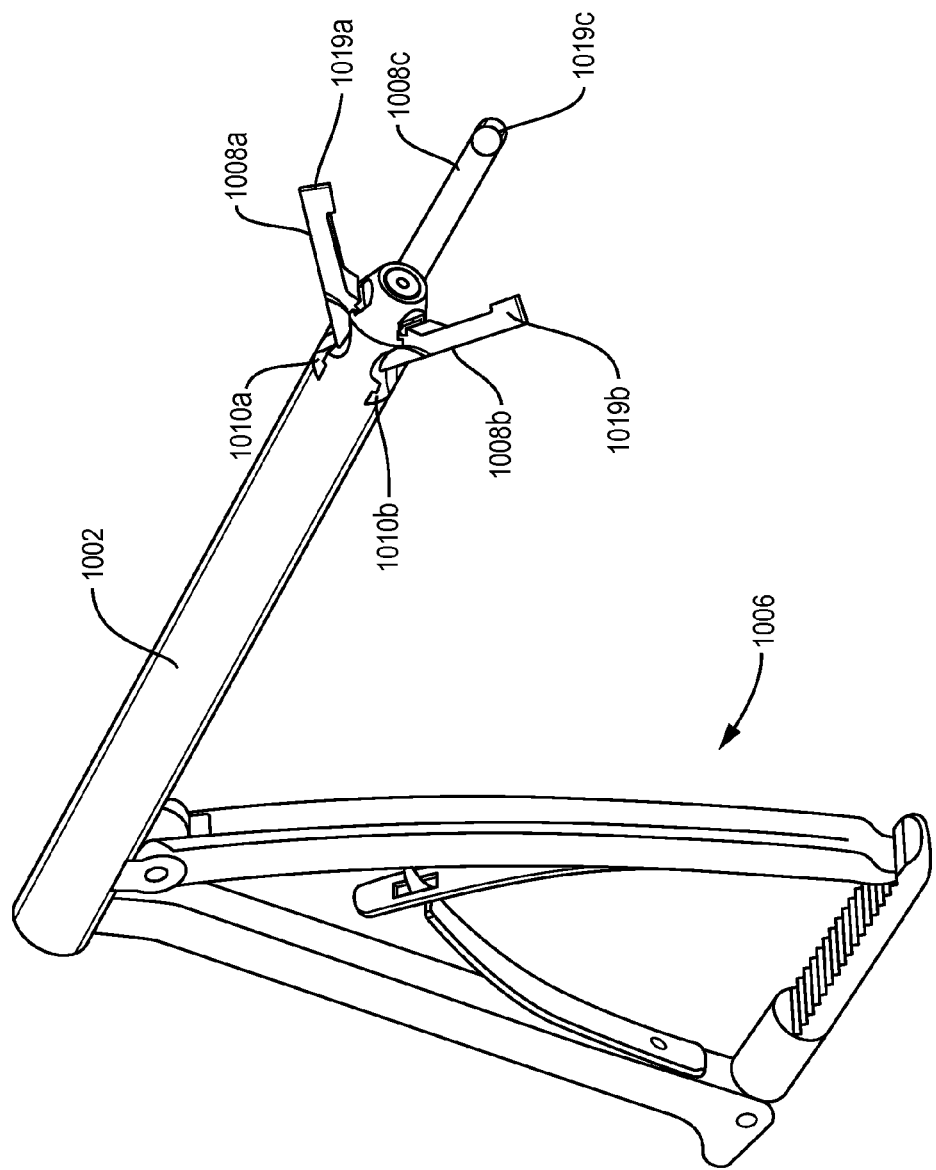

Next, as shown in FIG. 1F, the superior aspect of the coracoid process 106 is grasped with a coracoid drill guide 126 (e.g. as shown in FIGS. 10 and 11). Coracoid drill guide 126 includes a cannulated body 128 and a plurality of jaw members (e.g., three jaw members 130). The coracoid drill guide 126 is positioned on the superior aspect of the coracoid process 106 and the jaw members 130 are closed around the coracoid process 106 securing the drill guide 126 in position. A drill (e.g., a 1.9 mm drill, not shown) is passed down the cannula in the drill guide body 128 and a passage is drilled through the coracoid process 106 from the superior surface through the prepared grafting surface 124 on the inferior side.

Once the passage is drilled in the coracoid process 106, the coracoid drill guide 126 is removed and a first fastener (e.g. cannulated screw button 132 as shown in FIGS. 13A-13C and 16) is inserted in the passage on the superior aspect of the coracoid process 106 (FIG. 1G). A driver (e.g., as shown in FIGS. 12 and 14A-14D) is used to capture the screw button 132 (e.g., as shown in FIGS. 15A-15D), pass the screw button 132 over the drill (by passing the drill through the central cannula of the screw button), and screw the screw button 132 into the passage drilled into the coracoid process. After the screw button 132 is in place a looped guidewire 134 is passed through the screw button 132, coracoid process 106, and out of the graft surface 124 on the coracoid's 106 inferior surface. In alternative embodiments, the drill may be removed and the guidewire passed through the passages before inserting the screw button 132. The guidewire 134 may then be used to guide the screw button 132 into position.

As shown in FIG. 1H, the looped guidewire 134 is then guided towards the sleeve 118 in the anterior glenoid 104 using a grasper 136. A capture device (e.g., hook 138) placed through the sleeve 118 is used to capture the looped end 134a of the guidewire 134 and pull the guidewire 134 through the sleeve 118 to the posterior side of the glenoid 104. The sleeve 118 is then removed from the glenoid passage.

Figure 18:
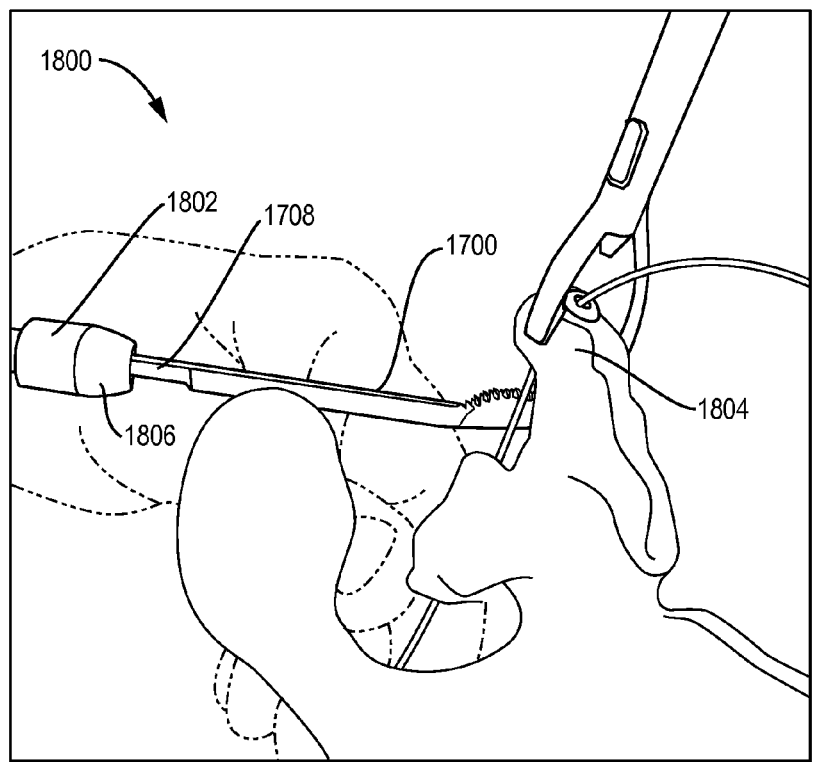
FIG. 18 is a photograph illustrating an embodiment of the surgical saw of FIG. 17 in use.

As shown in FIG. 1I, the tip of the coracoid process 106 is subsequently resected, at a length determined by the surgeon using a (e.g., a reciprocating saw 140 as shown in FIGS. 17 and 18). Next (FIG. 1J), the resected coracoid 142, also referred to herein as a graft, is transferred along the guidewire 134 through a tunnel in the subscapularis muscle to the grafting surface 110 on the anterior glenoid 104. The conjoined tendon remains attached to the resected coracoid 142 and provides a sling effect and dynamic tensioning of the inferior part of the subscapularis when the arm is abducted. The resected coracoid 142 with the attached conjoined tendon maintains the subscapularis split open, and it may be desirable to not attempt to close the split because doing so may limit rotation.

With the resected coracoid 142 positioned on the anterior glenoid 104 graft surface 110, a suture construct 144 including an attached surgical fastener 146 (e.g. as shown in FIGS. 19 and 20) is pulled through the glenoid and coracoid passages to secure the graft in place (FIGS. 1J-1L). A pull suture 144a is threaded through two looped ends (not shown) in the suture construct 144 and attached to the looped end 134a of the guidewire 134. As the guidewire 134 is withdrawn from the anterior side of the glenoid 104, the suture construct 144 is pulled with the guidewire 134, from the glenoid's 104 posterior side, through the glenoid and coracoid passages, and out of the screw button 132. The surgical fastener 146 includes a post with a hole through the post through which a looped portion 144b of the suture construct 144 is threaded. When the surgical construct 144 is pulled through the glenoid 104 the post on the surgical fastener 146 is drawn into the passage on the posterior glenoid 104, the body of the fastener 146 resting on the glenoid's 104 posterior surface and forming an anchor point (e.g. similar to a washer).

Once the suture construct 144 has been passed through the glenoid and coracoid passages, tension is applied to suture construct 144 and the resected coracoid 142 is secured in place. The two looped ends of the suture bundle, which will be extending out of the screw button 132, are tied into a half-hitch knot 152, also known as a Nice knot, while the surgical fastener 146 rests on the posterior glenoid surface. The sliding Nice knot 152 is transported down the suture by pulling one of the two loops until the knot arrives at the screw button 132.

Figure 22:
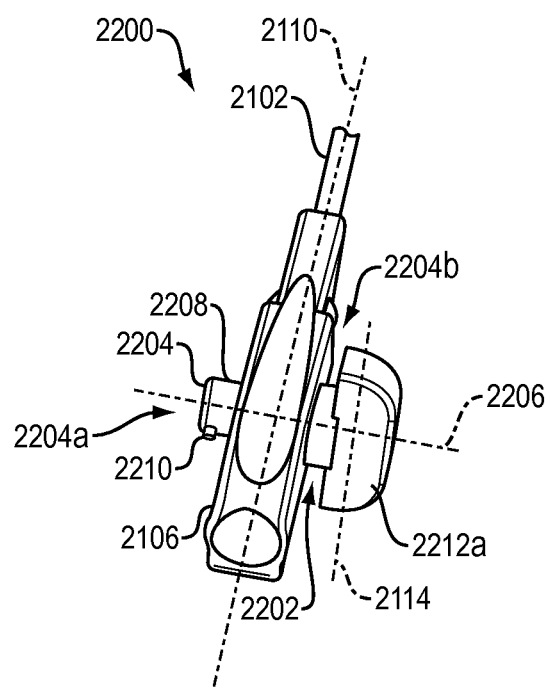
FIG. 22 is a schematic illustration of an embodiment of a suture tensioner having a transverse suture tensioning member.

As shown in FIG. 1M, a suture tensioner 148 (e.g. as shown in FIGS. 21-23) is used to compress the resected coracoid 142 against the glenoid 104. The suture loop is wrapped around a tensioning member 150 on the suture tensioner 148. In operation, the suture tensioner 148 draws tension on the suture knot and compresses the graft. Once in tension, several throws of a surgeon's knot or several half-hitches are tied to secure the Nice knot 152 and the graft 142. Finally (FIG. 1N), any extra length of suture is cut and the coracoid graft 142 onto the anterior glenoid 104 can heal.

Figure 24A:
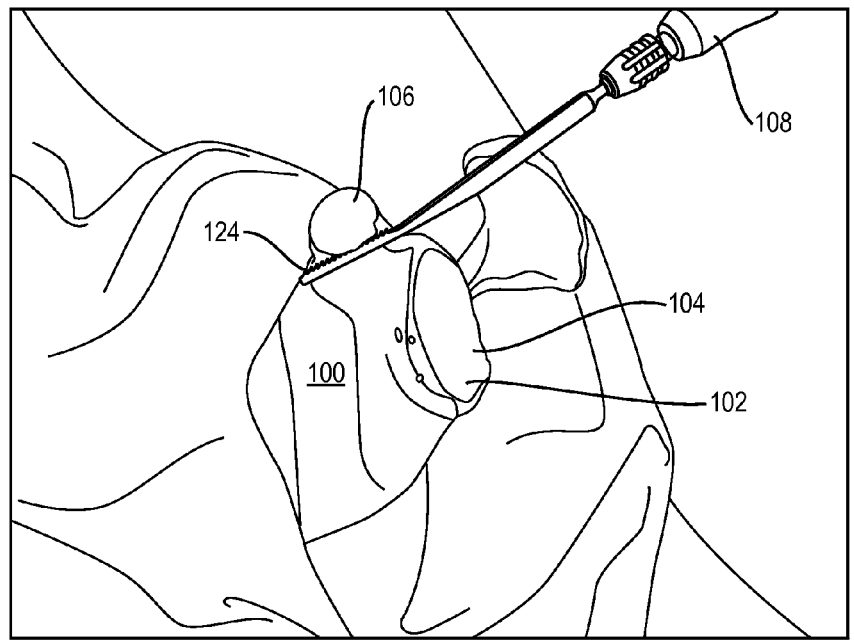
FIGS. 24A-24T illustrate an alternative embodiment of a procedure for repairing an area of glenoid bone loss in a patient's shoulder.
Figure 24B:
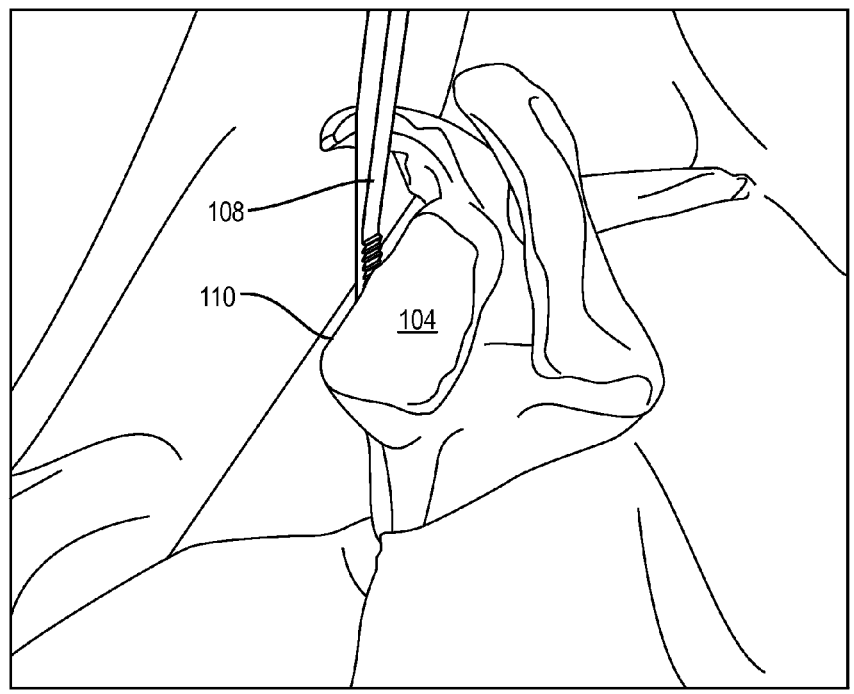
Figure 24C:
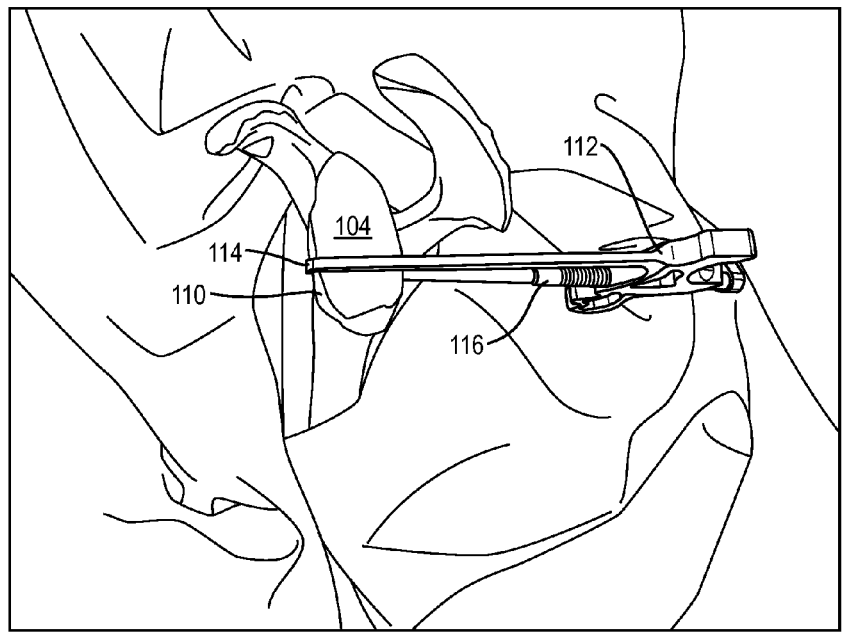
Figure 24D:
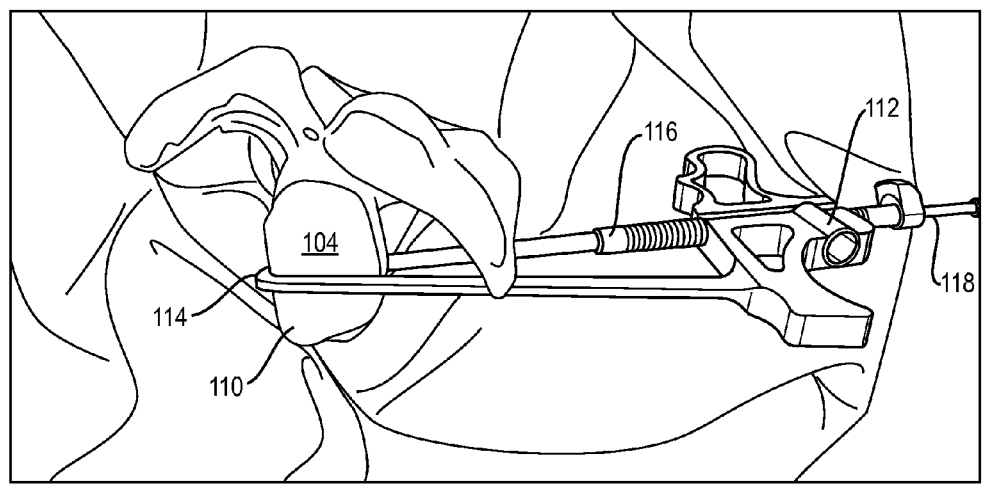
Figure 24E:
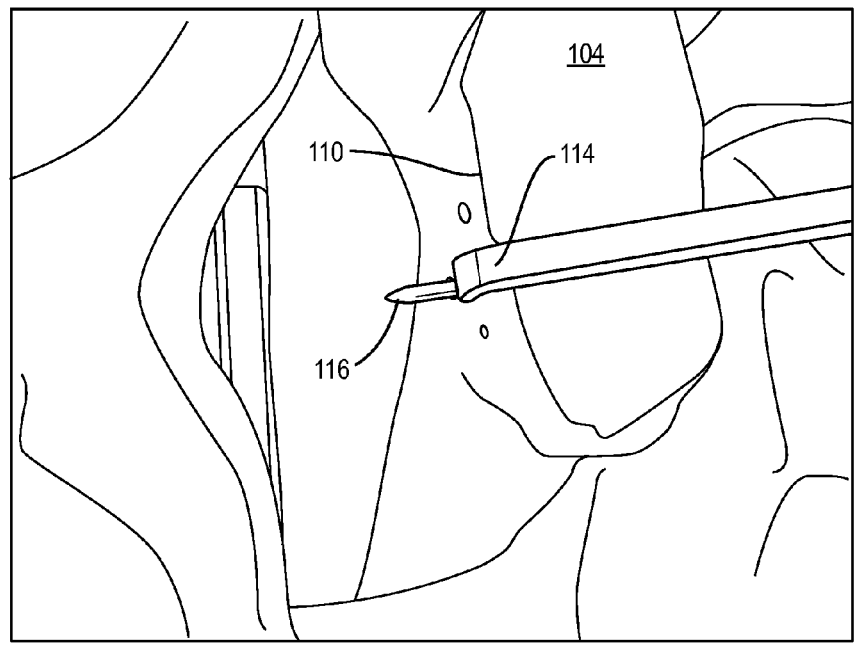
Figure 24F:
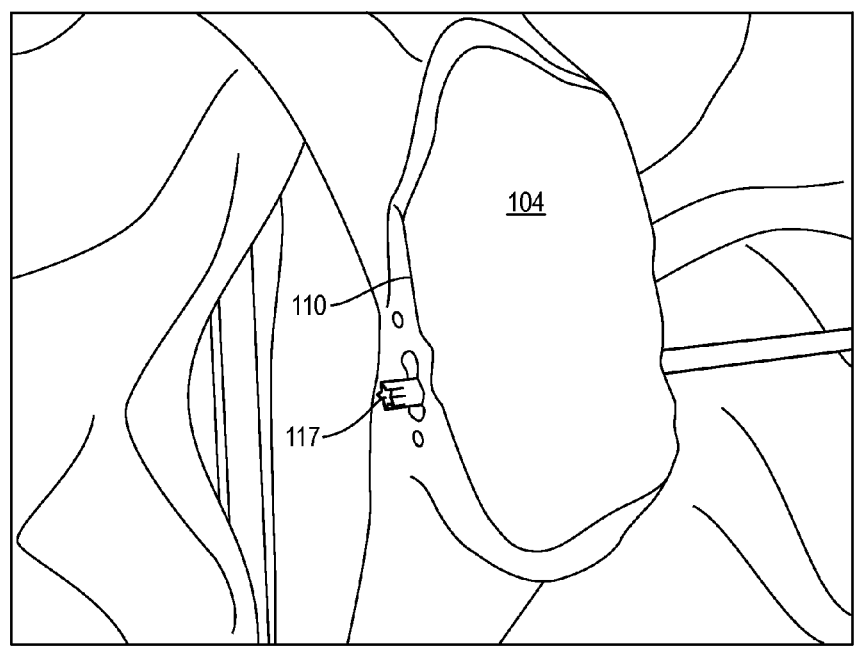
Figure 24G:
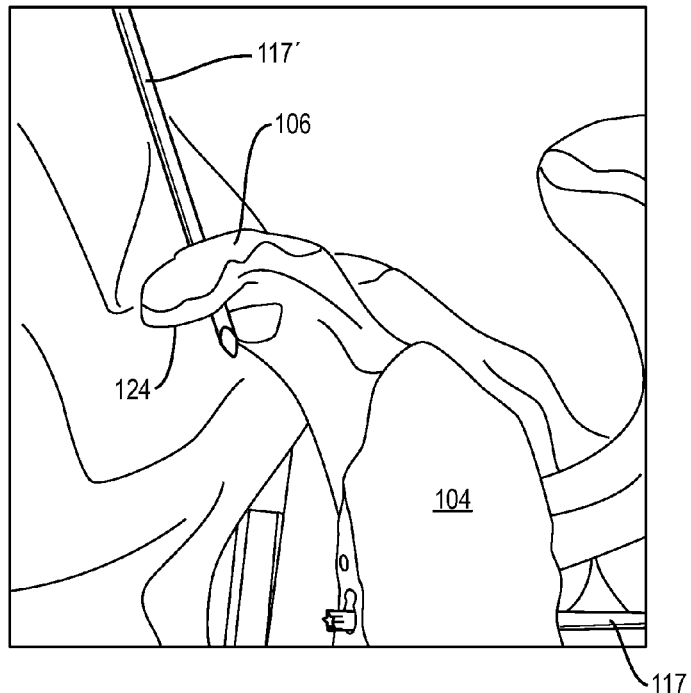
Figure 24H:
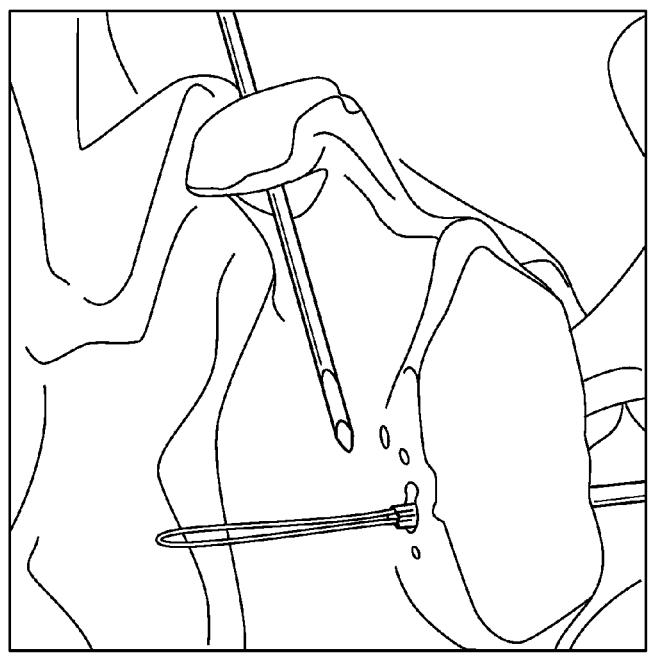
Figure 24I:
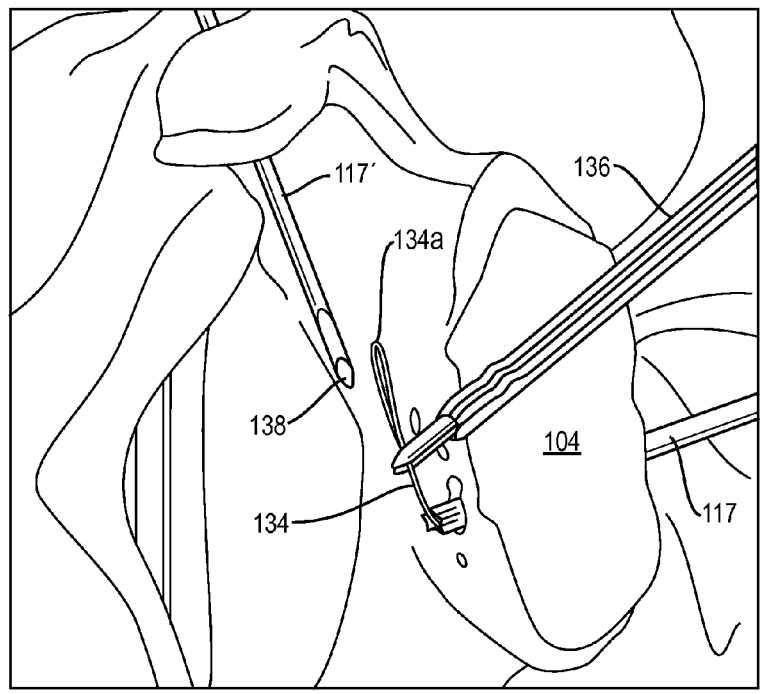
Figure 24J:
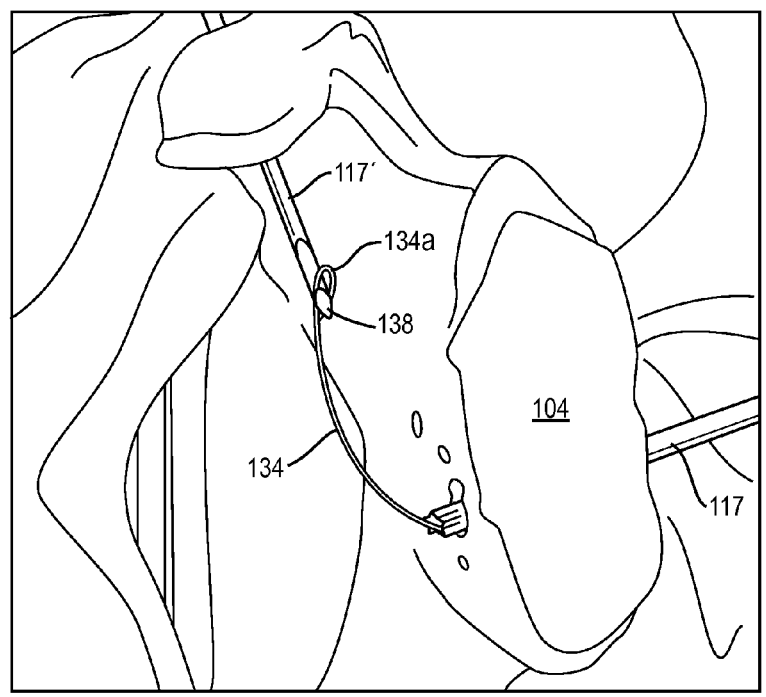
Figure 24K:
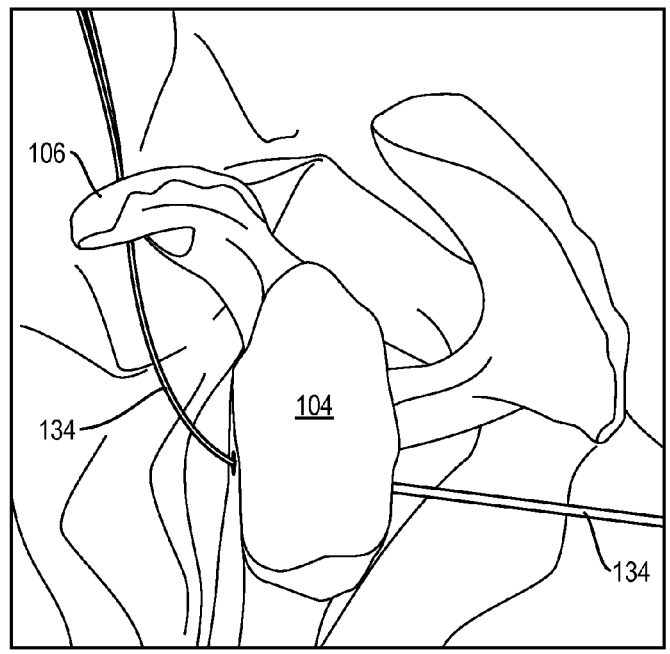
Figure 24L:
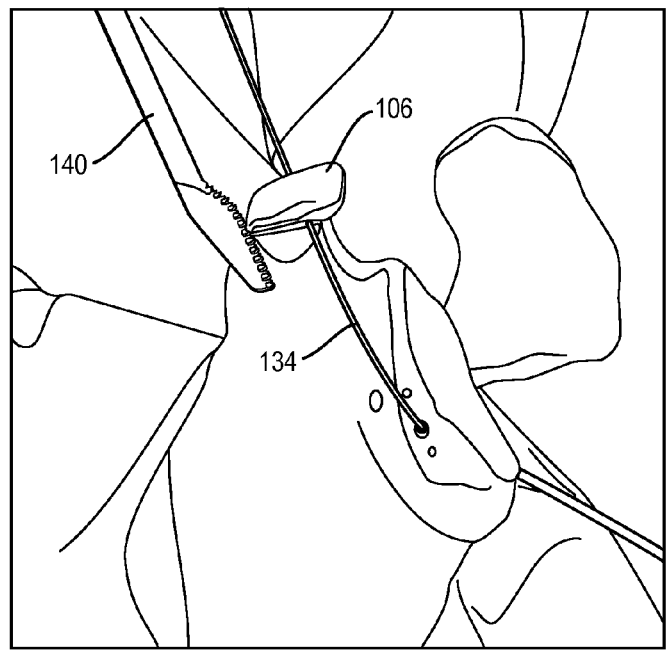
Figure 24M:
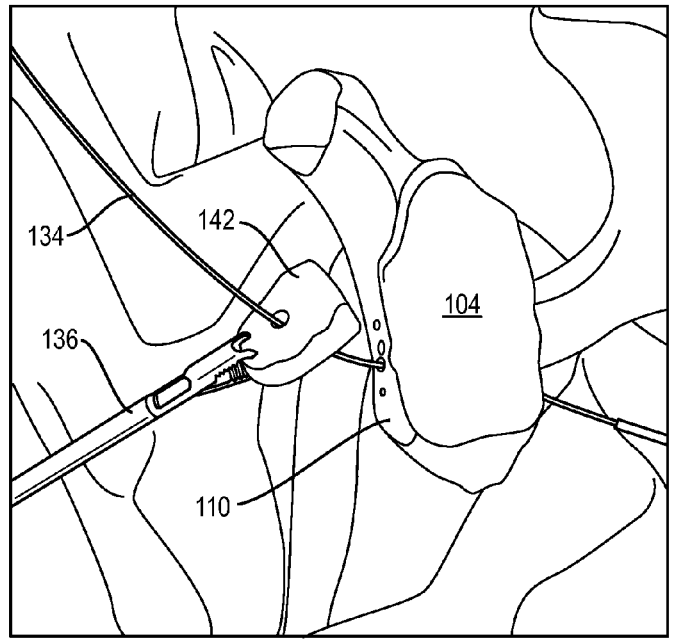
Figure 24N:
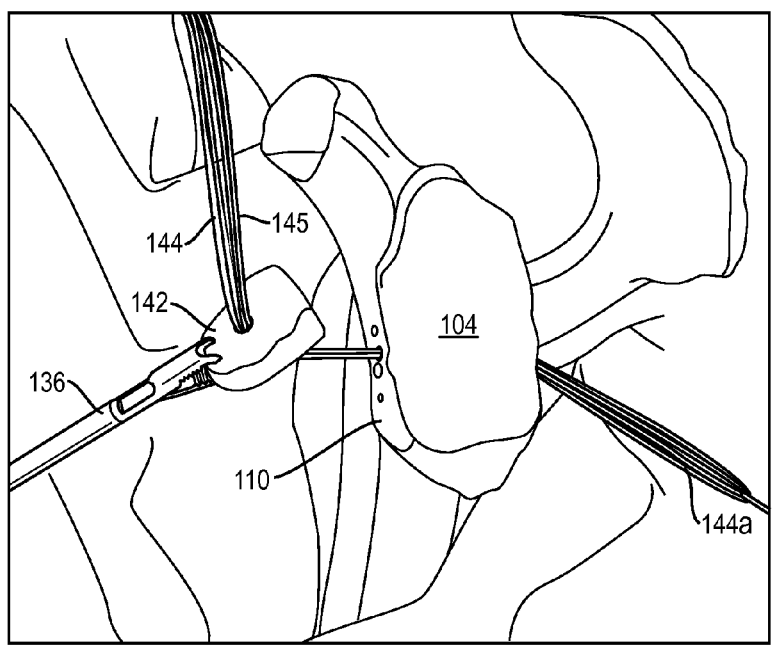
Figure 24O:
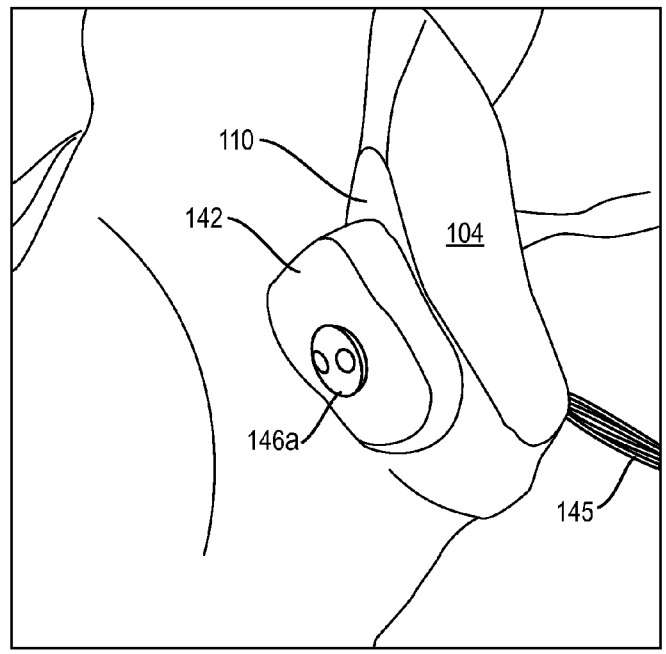
Figure 24P:
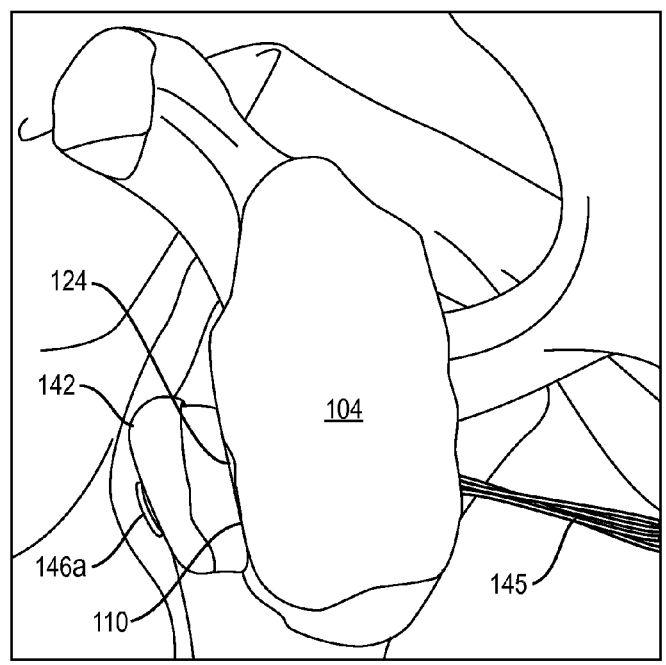
Figure 24Q:
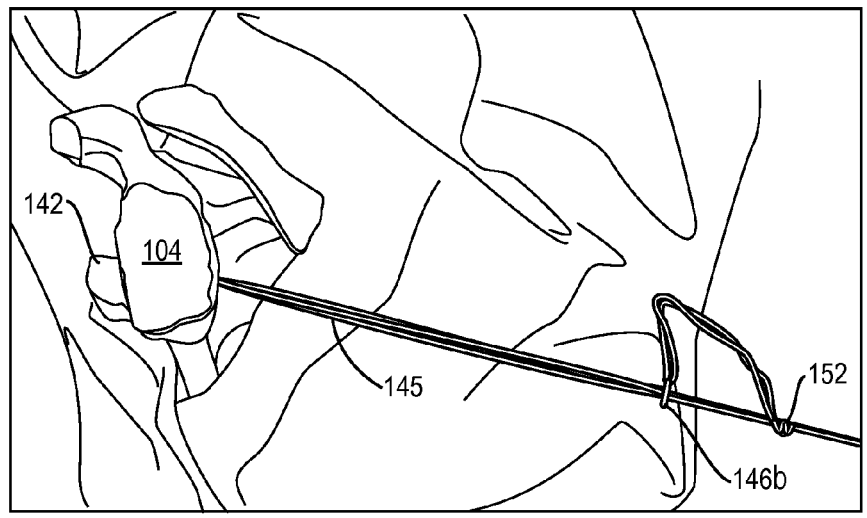
Figure 24R:
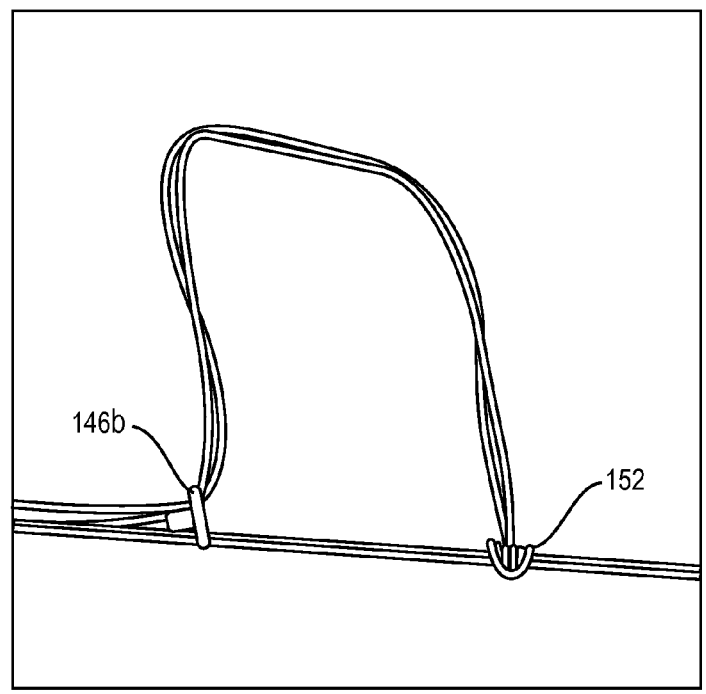
Figure 24S:
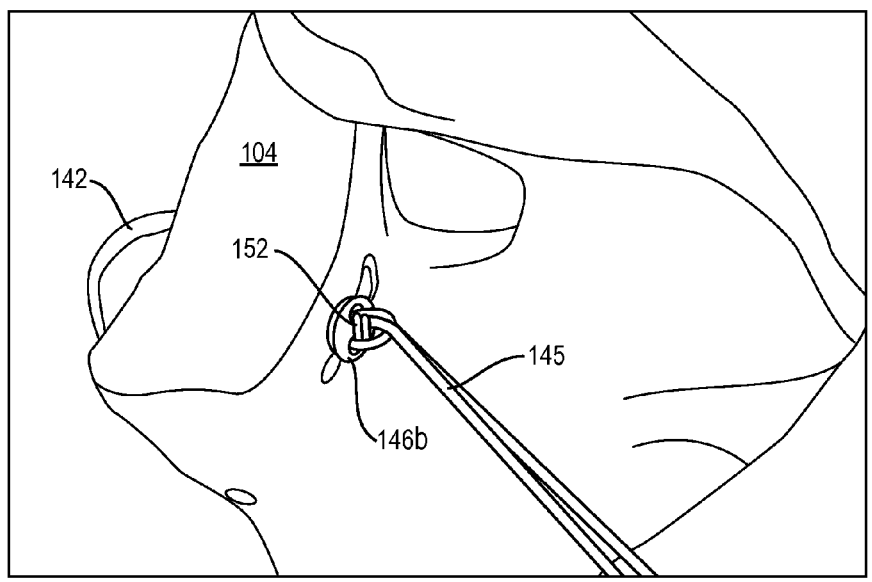
Figure 24T:
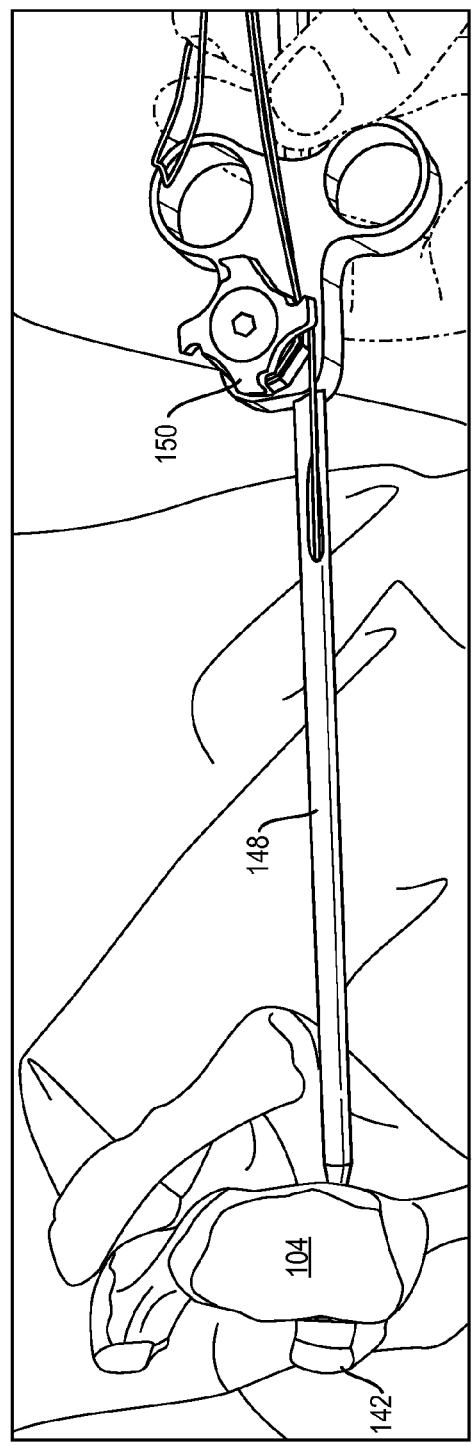

FIGS. 24A-24T illustrate an alternative embodiment of a procedure for repairing an area of glenoid bone loss in a patient's shoulder. FIGS. 24A-24T show a scapula 100 with a glenoid 104, including a region of glenoid bone loss 102, and a coracoid process 106.

FIGS. 24A-24B show a rasp 108 (e.g. as shown in FIGS. 7 and 8) being used to prepare the grafting surface 110 on the anterior surface of the glenoid 104, adjacent to an area of bone loss 102, and the grafting surface 124 on the inferior surface of the coracoid 106. In certain embodiments, not shown, the rasp may be attached to a powered reciprocating handle.

Next, as shown in FIG. 24C, a glenoid drill guide 112 (e.g. as shown in FIG. 9) is positioned on the glenoid 104. The glenoid drill guide 112 is inserted through a posterior portal in the patient's shoulder along a half cannula (not shown) to protect the articular cartilage. An engagement member on the distal end of the glenoid drill guide 112 (e.g., hook 114) is placed at a selected position on the glenoid 104 (e.g., the "five o'clock" position) and the drill guide 112 is visually aligned perpendicular to the prepared grafting surface 110 (FIG. 1C). Properly aligning the drill guide 112 to the prepared grafting surface 110 helps to prevent misalignment or post-operative graft movement. In certain embodiments, not shown, visual alignment of the drill guide may be accomplished through one of the incisions.

Next, as shown in FIGS. 24D-24F, a passage is drilled through the glenoid 104 in a direction from the posterior surface to the prepared graft surface 110 on the anterior glenoid surface. The drill bullet 116, including glenoid sleeve 117 and the drill 118, is advanced through the drill guide 112 the sleeve 117 is barely exposed visibly on the anterior surface of the glenoid 104 (FIG. 24E). The drill 118, bullet 116, and guide 112 are then removed leaving the glenoid sleeve 117 in place to provide a cannula for passing the guidewire (FIG. 24F).

Next, as shown in FIG. 24G, another passage is drilled through the coracoid process. As discussed above, the superior aspect of the coracoid process is grasped with a coracoid drill guide (e.g., 126 as shown in FIGS. 10 and 11). Coracoid drill guide includes a cannulated body and a plurality of jaw members. The coracoid drill guide is positioned on the superior aspect of the coracoid process and the jaw members are closed around the coracoid process 106 securing the drill guide in position. A drill (e.g., a 1.9 mm drill, not shown) is passed down the cannula in the drill guide body and a passage is drilled through the coracoid process from the superior surface through the prepared grafting surface on the inferior side. A glenoid sleeve 117' is further guided through the coracoid passageway using the drill as a guide. Once the passage is drilled in the coracoid process 106, the coracoid drill guide and drill 126 are removed, retaining the coracoid sleeve 117' in place.

As shown in FIG. 24H-24K, a looped guidewire (e.g., 134) is then advanced from the anterior surface of the glenoid 104 to the superior surface of the coracoid, through the glenoid and coracoid passages. For example, the guidewire 134 is passed through the glenoid sleeve 117, from the posterior surface of the glenoid 104 to the glenoid graft surface 110 (FIG. 24H). A capture device (e.g., hook 138) is also placed through the coracoid sleeve 117' to capture the looped end 134a of the guidewire 134. A grasper 136 is employed to guide the looped end 134a of the guidewire 134 towards the coracoid sleeve 117' to facilitate such capture (FIG. 24I). Using the hook 138, the guidewire is further retracted through the coracoid sleeve 117 to the superior surface of the coracoid 106 (FIG. 24J). Subsequently, the coracoid sleeve 117' and the glenoid sleeve 117 are removed (FIG. 24K).

As shown in FIGS. 24L-24P, the tip of the coracoid process 106 is subsequently resected and transferred into contact with the glenoid 104. For example, as illustrated in FIG. 24L, a saw (e.g., reciprocating saw 140) may be employed to resect the coracoid 106 at a length determined by the surgeon. Next the resected coracoid 142, also referred to herein as a graft, is transferred along the guidewire 134 through a tunnel in the subscapularis muscle to the grafting surface 110 on the anterior glenoid 104. For example, a device such as grasper 136 may be employed to facilitate the transfer (FIG. 24M). The conjoined tendon remains attached to the resected coracoid 142 and provides a sling effect and dynamic tensioning of the inferior part of the subscapularis when the arm is abducted.

The resected coracoid 142 with the attached conjoined tendon maintains the subscapularis split open, and it may be desirable to not attempt to close the split because doing so may limit rotation.

With further reference to FIGS. 24N-24O, the resected coracoid 142 is positioned on the anterior glenoid 104 graft surface 110. For example, a suture construct 144 including a suture 145 and an attached surgical fastener 146 (e.g. as shown in FIGS. 19 and 20) is attached to the guidewire 134 extending through the superior surface of the glenoid 106 (FIG. 24N). For example, a pull suture 144a is threaded through two looped ends (not shown) in the suture construct 144 and attached to the looped end 134a of the guidewire 134. As the guidewire 134 is withdrawn from the coracoid passage, a portion of the suture 145, including the suture ends, is pulled with the guidewire 134, through the coracoid and glenoid passages, and out of posterior surface of the glenoid 104.

The surgical fastener 146 includes a post with a hole through the post through which a looped portion 144b of the suture construct 144 is threaded. When the suture 145 is pulled through the glenoid 104, the post on the surgical fastener 146 is drawn into the coracoid passage, with the body of the fastener 146 resting on the formerly superior coracoid surface (FIG. 24O, 24P). In this manner, the surgical fastener 146 can urge the resected coracoid 142 towards the glenoid 104, facilitating transfer of the resected coracoid 142.

With reference to FIGS. 24Q-24T, the resected coracoid 142 is secured in place. Once the ends of the suture 145 have been passed through the glenoid and coracoid passages, the suture ends are routed through a second surgical fastener 146b (FIGS. 24Q, 24R). In certain embodiments, the second surgical fastener 146b may be the same as surgical fastener 146 (e.g. as shown in FIG. 19), including a body, a pair of holes extending through the body, and a post extending from a surface of the body. One of the ends of the suture 145 is passed through one of the pair of holes and another end of the suture 145 is passed through the other of the pair of holes. The two looped ends of the suture 145, which will be extending out of the second fastener 146b, are tied into a half-hitch knot 152, also known as a Nice knot. The half-hitch knot is subsequently advanced into contact with the second fastener 146b and then further advanced so as to urge the post of the second fastener 146b into the glenoid passageway (FIG. 24S).

As shown in FIG. 24T, a suture tensioner 148 (e.g. as shown in FIGS. 21-23) is used to compress the resected coracoid 142 against the glenoid 104. The suture loop is wrapped around a tensioning member 150 on the suture tensioner 148 and the suture tensioner 148 draws tension on the suture knot and compresses the graft. Once in tension, several throws of a surgeon's knot or several half-hitches are tied to secure the Nice knot 152 and the graft 142. Finally, any extra length of suture is cut and the coracoid graft 142 onto the anterior glenoid 104 can heal.

Figure 2A:
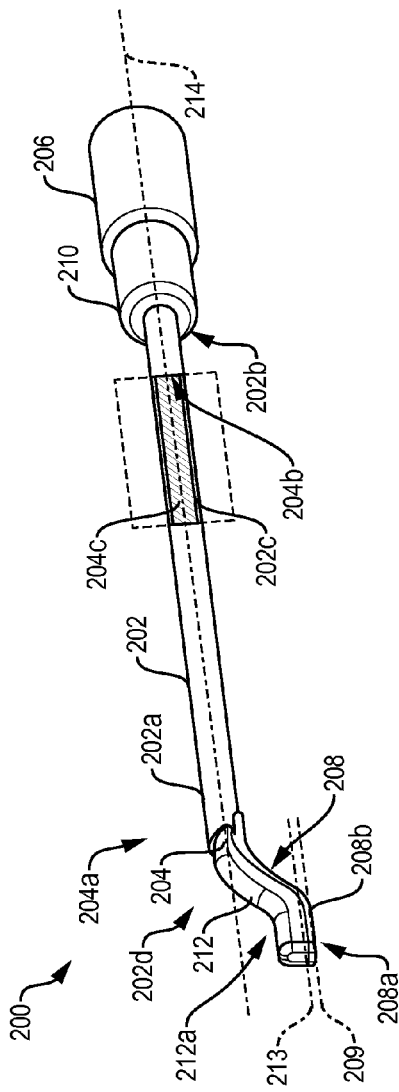
FIGS. 2A-2B are schematic illustrations of an embodiment of a radial opening tissue spreader; (A) open position; (B) closed position.
Figure 2B:
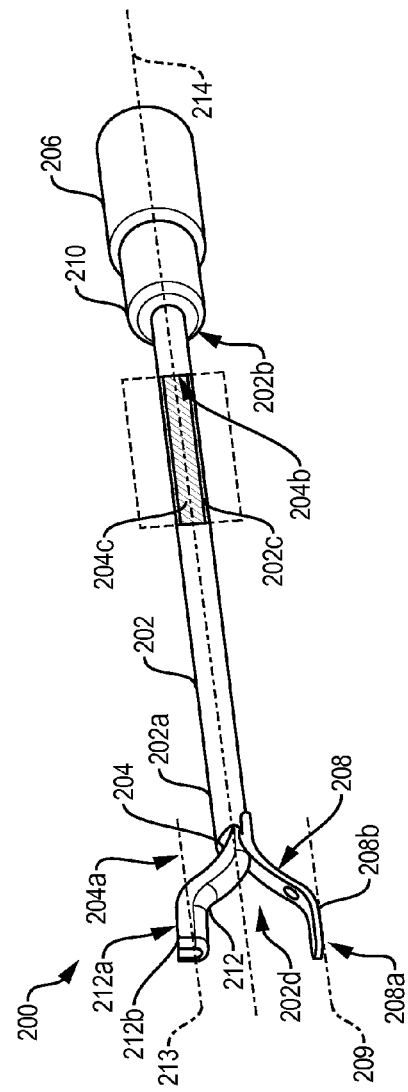

FIGS. 2A and 2B illustrate an example of a radial opening tissue spreader 200 used, for example, to spread muscle tissue during a surgical procedure. Spreader 200 includes a first member 202, a second member 204, and a handle 206.

The first member 202 includes a body 202 shaped like an elongated hollow rod. The body 202 includes a distal end 202a, a proximal end 202b, and a shaft portion 202c. The body 202 further defines a lumen 202d and connects the distal end 202a and the proximal end 202b. In addition, the body 202 includes a paddle portion 208 (e.g. a fixed paddle) located at the distal end 202a. The paddle portion 208 includes a spreading member 208a with a spreading surface 208b that has a longitudinal axis 209 which is parallel to, but offset from, a central longitudinal axis 214 of the shaft portion 202c.

The offset distance between the spreading surface's longitudinal axis 209 and the central longitudinal axis 214 is greater than the radius of the shaft portion 202c. The body 202 also includes an enlarged cylinder portion 210 at the proximal end 202b having a diameter greater than the diameter of the shaft portion 202c on which the handle 206 rests.

The handle 206 is coupled to the second member 204, which is, for example, a shaft that includes a distal end 204a, a proximal end 204b, and a shaft portion 204c that connects the distal end 204a and the proximal end 204b and is disposed within the lumen defined by the shaft portion 202c of the body 202. In addition, the shaft 204 includes a paddle portion 212, e.g. a movable paddle, located at the distal end 204a of the shaft 204. The paddle portion 212 includes a spreading member 212a with a spreading surface 212b that has a longitudinal axis 213 which is parallel to but offset from a central longitudinal axis 214 of the shaft portion 202c of the body 202. The offset distance between the spreading surface's longitudinal axis 209 and the central longitudinal axis 214 is also greater than the radius of the shaft portion 202c of the body 202.

The shaft 204 and the body 202 are configured to rotate relative to each other about the central longitudinal axis 214 between a closed position (FIG. 2A) and an open position (FIG. 2B). The handle 206 is coupled to the proximal end 202b of the body and the proximal end 204b of the shaft 204 such that rotation of the handle 206 causes the shaft 204 to rotate relative to the body 202. When the spreader 200 is in the open position, the spreading members 208 and 212, and their respective spreading surfaces 208b, 212b, are substantially diametrically opposed relative to the central longitudinal axis 214. Also, when in the open position, the first spreading surface 208b and the second spreading surface 212b are separated by a distance equal to the first offset distance between the axis 209 and 214 plus the second offset distance between the axis 213 and axis 214. For example, the first offset distance may be 0.55 inches and the second offset distance may be 0.45 inches forming a total spreading distance of 1.0 inch. By contrast, when the spreader 200 is in the closed position, the second spreading member 212a is nested in the first spreading member 208a and the first spreading surface 208b substantially overlaps with the second spreading surface 212b. So positioned, the spreader adopts a relatively low profile, permitting the spreader 200 to be easily inserted into an incision.

In use, the paddle portions 208 and 212 are placed in the closed position and into an incision. Subsequently, the paddle portions 208 and 212 are rotated to the open position. The spreading surfaces 208b and 212b spread the tissue apart and thereby create an accessible opening in the tissue.

Figure 3A:
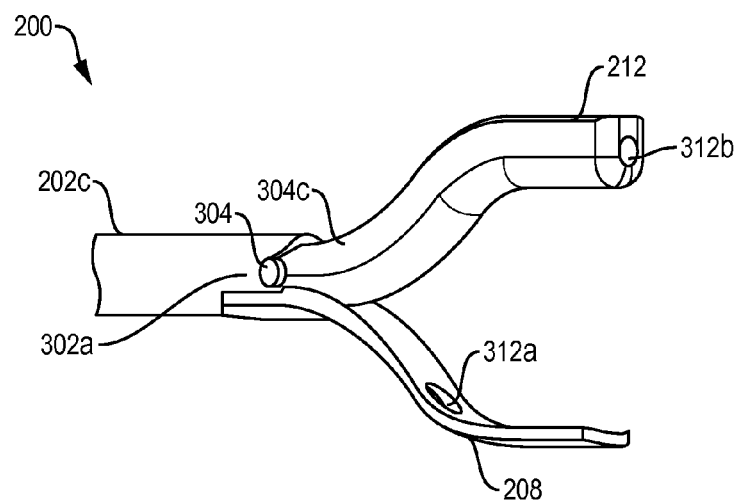
FIGS. 3A-3C are schematic illustrations of an embodiment of a locking mechanism for the radial opening spreader of FIGS. 2A-2B; (A) open position; (B) closed position; (C) spring of locking mechanism.
Figure 3B:
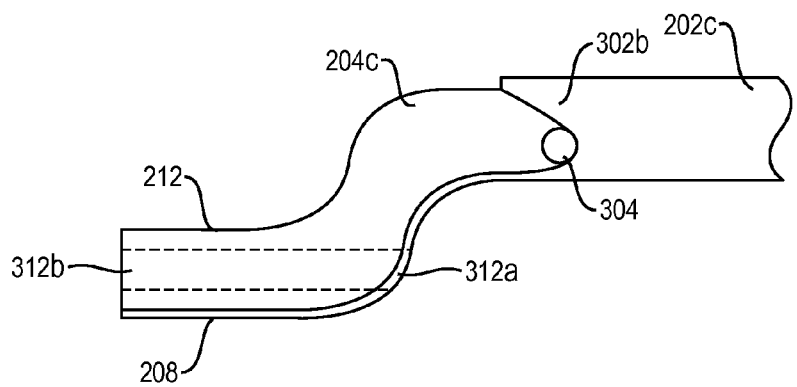
Figure 3C:
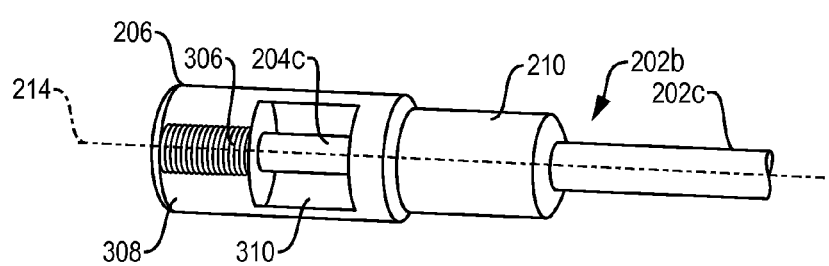

FIGS. 3A-3C are detailed illustrations of an example of a locking mechanism for a radial opening spreader 200. The spreader 200 may include a locking mechanism to stabilize the first and second members in to the open and closed position, for example, to prevent the spreader 200 from inadvertently closing or opening during a surgical procedure. The locking mechanism includes first and second saddle shaped notches 302a and 302b formed on opposite sides of the body's shaft portion 202c at the distal end 202a and a post 304 located on the shaft portion 204c at the second distal end 204a of the shaft 204. As illustrated in FIG. 3A, when the body 202 and the shaft 204 are in the open position, the post 304 rests in the first notch 302a. As illustrated in FIG. 3B, when the body 202 and the shaft 204 are in the closed position (FIG. 3B) the post 304 rests in the second notch 302b. In addition, the locking mechanism includes a spring 306 that biases the shaft 204 along the body's central longitudinal axis 214 towards the first proximal end 202b. For example, the spring 306 may be compressed inside the handle 206 (FIG. 3C) against an inner surface 308 of the handle 206 and the enlarged cylindrical portion 210 of the body 202 to create a force along the central longitudinal axis 214, biasing the shaft 204 towards the proximal end 202b of the body 202. Moreover, the spring force holds the post 304 in either of the notches 302a and 302b, thereby locking the spreader 200 in either the open or closed position.

The first and second spreading members 208a and 212a include respective lumens 312a and 312b that align to form a single passage through the first and second spreading members 208a and 212a when the spreader 200 is in the closed position. These lumens may, for example, permit the use of a guide wire to direct the closed paddle portions 208 and 212 into an incision, for example. Also, in some implementations, the shaft portion 204c defines a second lumen 310 concentric with the lumen 202d defined by the first shaft portion 202c, for example, to permit passing another surgical tool (e.g. a drill or guide wire) into the spread tissue.

FIGS. 4A-4D illustrate a half-cannulated radial opening tissue spreader 400 used, for example, to spread muscle tissue during a surgical procedure and allow a secondary tool, such as a screwdriver, to be passed through the spread tissue. The half-cannulated radial opening spreader device 400 includes a first member 402, a second member 404, and a removable obturator 406. The half-cannulated spreader 400 may be similar to spreader 200 except that a side of the body 402 and shaft 404 is cutaway resulting in a "C"-shaped cross section.

The first member 402 is, e.g., a body shaped like an elongated hollow rod with a "C"-shaped cross section. The body 402 includes a first distal end 402a, a proximal end 402b, a shaft portion 402c, and a slot 402e in the shaft portion 402c which extends from the distal end 402a to the proximal end 402b. The shaft portion 402c further defines a lumen 402d and connects the distal end 402a and the proximal end 402b. In addition, the body 402 includes a paddle portion 408, e.g. a fixed paddle, located at the distal end 402a. The paddle portion 408 includes a spreading member 408a with a spreading surface 408b that has a longitudinal axis 409 which is parallel to but offset from a central longitudinal axis 407 of the shaft portion 402c. The offset distance between the longitudinal axis 409 and the central longitudinal axis 407 is greater than the radius of the shaft portion 402c.

The second member 404, which is, for example, a shaft that includes a distal end 404a, a proximal end 404b, and a shaft portion 404c that defines a lumen 404d and connects the distal end 404a and the proximal end 404b and is disposed within the lumen defined by the shaft portion 402c of the body 402. The shaft portion 404c also includes a slot 404e which extends from the distal end 404a to the proximal end 404b. Similar to the body's shaft portion 402c, the shaft portion 404c forms a "C"-shaped cross section in the second shaft portion 404c. In addition, the shaft 404 includes a paddle portion 410, e.g. a moveable paddle, located at the second distal end 404a. The paddle portion 410 includes a spreading member 410a with a spreading surface 410b that has a longitudinal 30 axis 411 which is parallel to but offset from the central longitudinal axis 407. This second offset distance between the spreading surface's longitudinal axis 409 and the central longitudinal axis 407 is also greater than the radius of the shaft portion 402c.

Figure 4A:
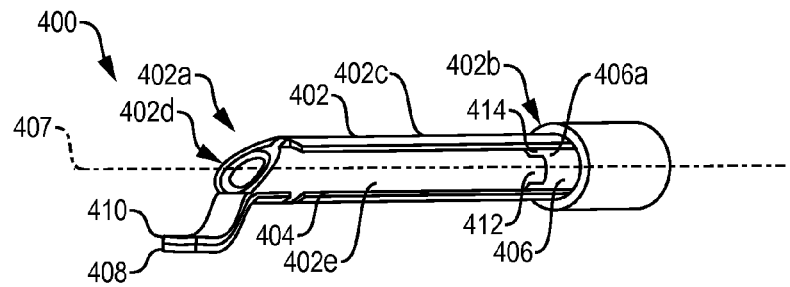
FIGS. 4A-4D are schematic illustrations of a half-cannulated radial opening tissue spreader; (A) closed position; (B) open position; (C) open position, cutaway; (D) open position, cutaway with inserted secondary tool.
Figure 4B:
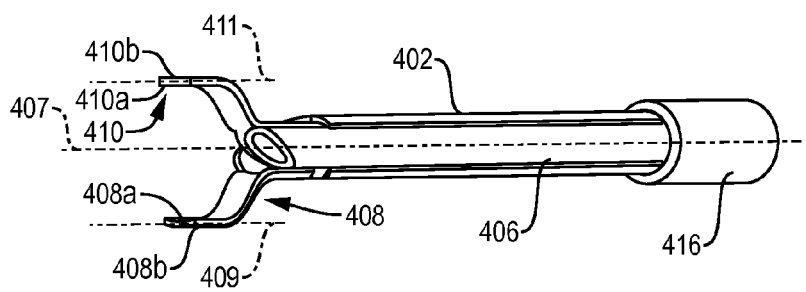
Figure 4C:
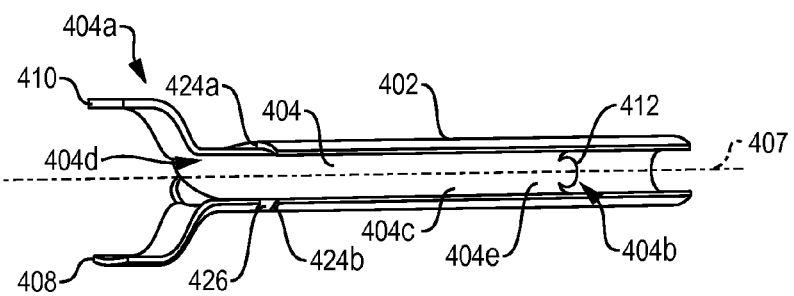

The shaft 404 also includes a first set of teeth 412 located at the shaft's proximal end 404b. The removable obturator 406 engages the shaft 404 by way of a second set of corresponding teeth 414 located at an obturator proximal end 406a that meshes with the shaft's first set of teeth 412. The obturator 406 is used to rotate the shaft 404 relative to the body 402 about the central longitudinal axis 407 between a closed position (FIG. 4A) and an open position (FIG. 4B) in a fashion similar to the operation of spreader 200 described above. In addition, the body 402 and the shaft 404 are configured such that when the half-cannulated spreader 400 is in the open position, the first and second slots 402e and 404e are aligned (FIG. 4B) and when the half-cannulated spreader 400 is in the closed position, the first and second slots 402e and 404e are not aligned (FIG. 4A).

Figure 4D:
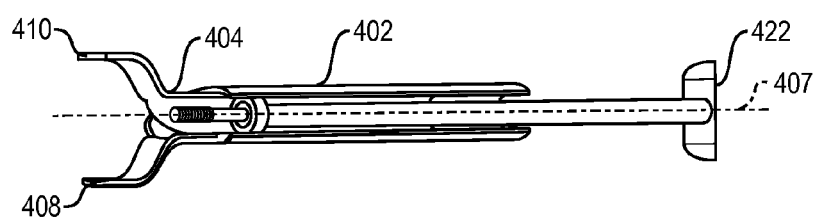

The obturator 406 may be removed (FIG. 4C) thereby making room for a secondary tool 422 to be inserted through the shaft 404 and body 402 into an incision (FIG. 4D). The slots 402e and 404e are aligned when the spreader 400 is in the open position to prevent confining the secondary tool 422 to the center of the spreader device 400, for example.

Figure 5:
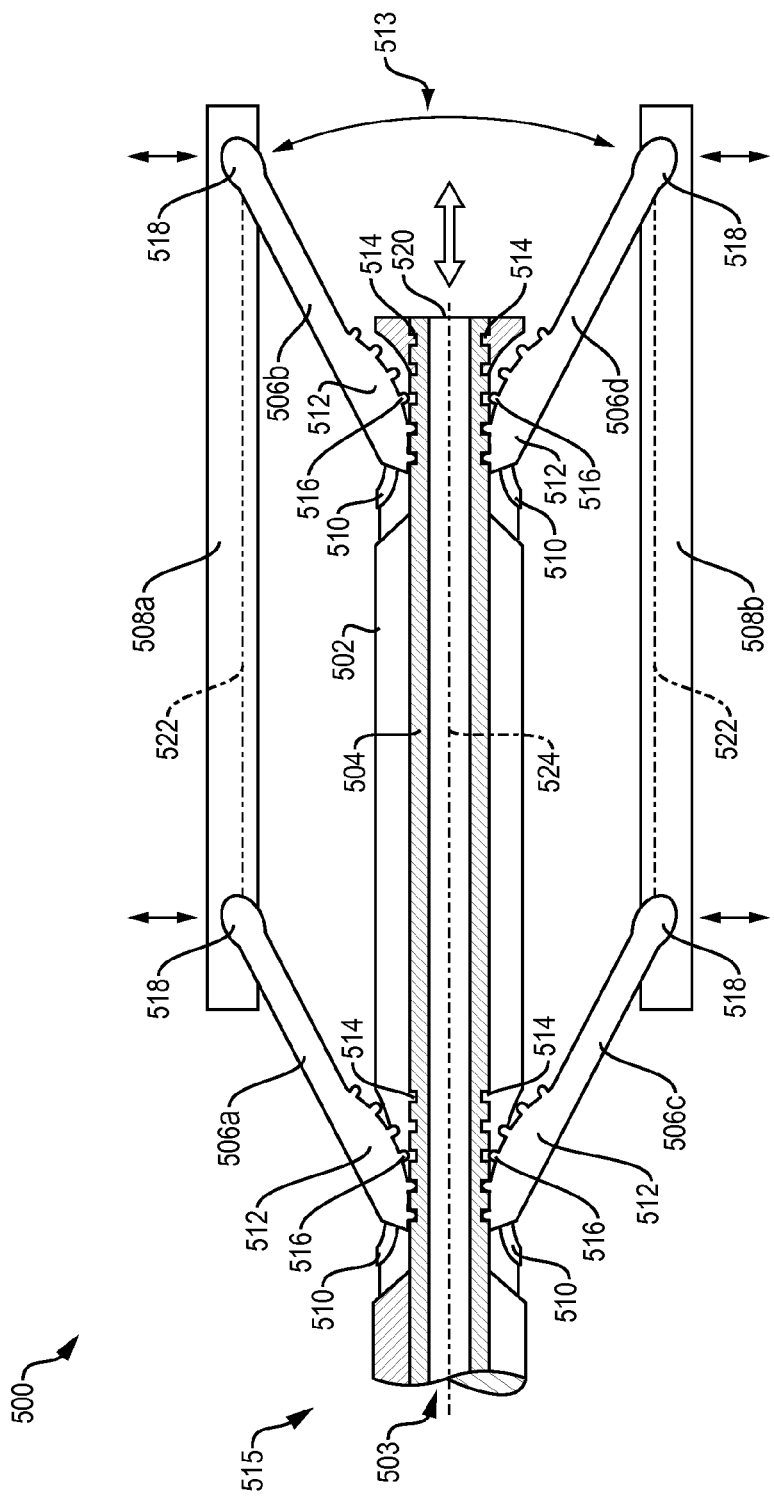
FIG. 5 is a schematic illustration of an embodiment of a parallel tissue spreader.

Furthermore, friction between the inner surface of the body 402 and the outer surface of the shaft 404 may prevent the spreader device 400 from inadvertently closing. Additionally, a first guide notch 424a and a second guide notch 424b are cut into opposite sides of the shaft portion 402c at the distal end 402a and a post 426 located on one side of the shaft portion 404c to prevent over rotation of the shaft when opening and closing the spreader 400. For example, the post 426 may rest in the first guide notch 424a when the spreader device 400 is in the closed position and the post 426 may rest in the second guide notch 424b when the spreader 400 is in the open position. FIG. 5 illustrates a parallel tissue spreader 500 used, for example, to spread muscle tissue during a surgical procedure. The spreader 500 includes a body member 502, an actuating member 504, a plurality of arms (e.g., 506a-506d), and a plurality of jaw members (e.g., 508a-508b).

The body member 502 includes a first lumen 503, and four ports 510, each of which is configured to accept a toothed end 512 of an arm 506a-506d. The body member 502 also includes a distal end 513 and a proximal end 515 opposite the distal end, the distal end 513 being configured for insertion into tissue and the proximal end 515 including a handle or actuator. The actuating member is a shaft 504 that is disposed within the first lumen 503 of the body member 502 and is configured to move axially relative to the body member 502 and along the central longitudinal axis 520. The shaft 504 includes toothed regions 514 aligned with the ports 510 and is coupled to the handle at the proximal end 515, the handle used to provide an axial force on the shaft 504. The teeth in the toothed regions 514 of the shaft 504 are configured to mesh with the teeth 512 on the arms 506a-506d, as illustrated in FIG. 6. The arms 506a-506d are coupled to the body member 502 at the ports 510 on a pivot, for example, a pin-less pivot joint 516 at the toothed end 512 of the arms 506a-506d. Furthermore, the arms 506a-506d are generally oriented with the toothed end 512 towards the proximal end of the body 515 and a second end of the arms 518 towards the distal end of the body 513.

In the example shown, two jaw members 508a and 508b are each coupled by pivots to a pair of arms 506a and 506b and 506c and 506d, respectively. In particular, a first jaw member 508a is coupled by a pivot at a proximal end of the jaw member 508a to the second end 518 of a first arm 506a and at a distal end of the jaw member 508a to the second end 518 of a second arm 506b. A second jaw member 508b is coupled by a pivot at a proximal end of the jaw member 508b to the second end 518 of a third arm 506c and at a distal end of the jaw member 508b to the second end 518 of a second arm 506d. The first jaw member 508a, the first arm 506a, and the second arm 506b are located on an opposite side of the body member 502 from the second jaw member 508b, the third arm 506c, and the fourth arm 506d.

The arms 506a and 506b and the shaft 504 are configured such that movement of the shaft 504 relative to the body member 502 causes the arms 506a and 506b to move the jaw member 508a away from the body member 502 while maintaining a longitudinal axis 522 of the jaw member 508a parallel to the central longitudinal axis 520 of the parallel tissue spreader 500. For example, when the shaft 504 is moved axially within the body member 502 along the central axis 520 the shaft teeth mesh with the arm teeth causing the arms 506a and 506b to pivot and the second end 518 of the arms 506a and 506b with the coupled jaw member 508a to move towards or away from the body member 502. In the example shown, when the shaft 504 is driven axially towards the distal end 513 of the body member 502, the arms 506a and 506b pivot outwards moving the jaw member 508a away from the body member 502, for example, opening the parallel tissue spreader 500. When the shaft 504 is driven axially towards the proximal end 515 of the body member 502, the arms 506a and 506b pivot inwards moving the jaw member 508a towards the body member 502, for example, closing the parallel tissue spreader 500. The arms 506c and 506d and jaw member 508b operate in the same manner. Thus, when the shaft 504 is driven towards the distal end 513, the first jaw member 508a moves in a first direction and the second jaw member 508b moves in a second direction, both directions being away from the body member 502. Similarly, when the shaft is driven axially towards the proximal end 515 of the body 502, the first jaw member 508a and the second jaw member 508b move towards the body member 502.

The shaft 504 includes a lumen 524 that extends through the shaft 504 from the proximal end 515 to the distal end 513 and includes an opening at the proximal end of the shaft 504 to receive another surgical instrument, for example, a drill or a guide wire, that can be passed down the lumen 524 to exit from an opening of the lumen located at distal end of the shaft 504.

In some embodiments, the parallel tissue spreader includes only one pair of arms and a single jaw member such that tissue spreading is performed between the body member and the single jaw member, instead of between two jaw members 508a and 508b located on opposite sides of the body member 502. In further alternative embodiments, three or more arms may be coupled to each jaw member, for example, to increase the spreading force applied by each jaw member to the tissue. Additionally, some implementations may include three or more jaw members coupled to three or more sets of arms each set coupled to the body member, spaced around the body member (e.g., evenly spaced). For example, a parallel tissue spreader may include three jaw members each coupled to a pair of arms, the pairs of arms coupled to the body in locations spaced 120° apart around the body member, thereby spreading tissue in a wider pattern.

FIG. 6 illustrates an embodiment of a pin-less joint 516 used for the arm 506a (and 506b-506d) of the spreader 500. The arm 506a and port 510 located in the body 502 are sized such that the side surfaces 602 of the arm 506a either nearly contact or loosely contact the corresponding inner surfaces 604 of the port 510. The toothed end 512 of the arm 506a includes a pair of arcuate flanges 606 projecting outward from the arm's side surfaces 602. Likewise, the port 510 includes a corresponding pair of arcuate grooves 608 cut into the port's inner surfaces 604. The arcuate flanges 606 and grooves 604 are configured to be of appropriate radius and size such that the arcuate flanges 606 are slidable within the arcuate grooves 608. Thus, the flanges 606 and grooves 608 form an arcuate lug and groove arrangement which allows the arm 506a to pivot about the axis 610. For example, as the shaft 504 is moved relative to the body member 502, the shaft teeth 514 engage the arm teeth 512 causing the arcuate flanges 606 to slide within the arcuate grooves 608 thereby causing the arm 506a to pivot.

In some implementations the location of the arcuate flanges 606 and grooves 608 may be reversed. For example, the flanges 606 may be located on the inner surfaces 604 of the port 510 while the grooves 608 may be cut into the side surfaces 602 of the arm 506a. Furthermore, some implementations may use different shaped arcuate flanges 606 and grooves 608, for example, the flanges 606 and grooves 608 may have a dovetail cross section, a rectangular cross section, or a key-hole shaped cross section.

Figure 7A:
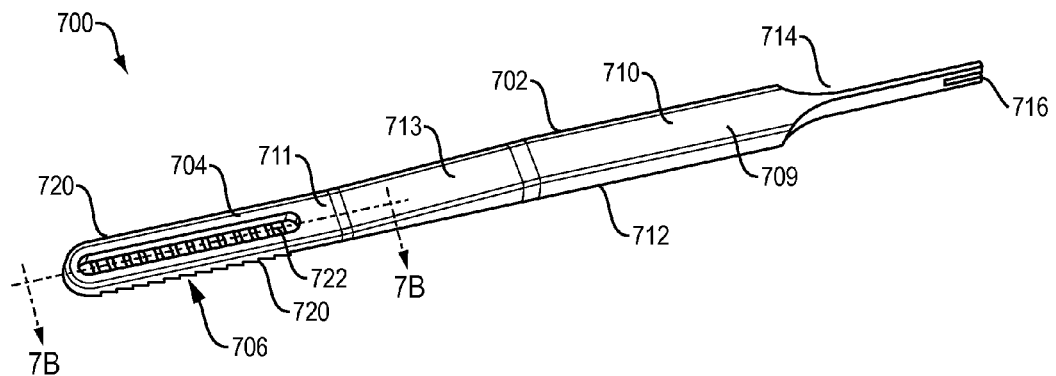
FIGS. 7A-7B are schematic illustrations of an embodiment of a bone contouring device; (A) perspective view; (B) cutaway view.
Figure 7B:
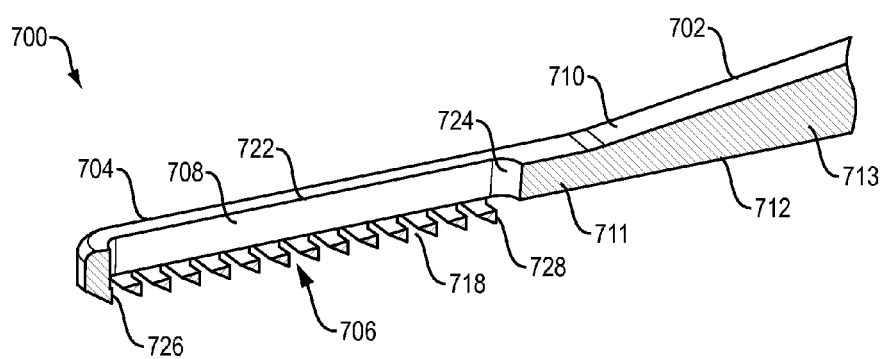

FIGS. 7A and 7B illustrate a bone contouring device, or rasp, 700 used, for example, to prepare the surface of a joint to receive a bone graft during a surgical procedure. The rasp 700 includes a body portion 702 and a head portion 704, including a plurality of teeth 706 and a channel 708 above the teeth 706. FIG. 7B shows a detailed view of cross section A-A of the head portion 704.

The body portion 702 is an elongated rectangular structure having an upper surface 710 and a lower surface 712. The upper surface 710 and lower surface 712 are generally flat with the upper surface 710 tapered at the end nearest the head portion 704. In particular, the body portion 702 has a first portion 709 with a distance between the upper surface 710 and lower surface 712 of D1, a second portion 711 with a distance between upper surface 710 and lower surface 712 of D2, and a tapering portion 713 in which the distance tapers from D1 to D2. Additionally, the taper portion 713 tapers from the upper surface 710 towards the lower surface 712 with the lower surface 712 remaining substantially straight along its full length.

The end of the body portion 702 opposite the head portion 704 includes a powered handpiece connection portion 714. The handpiece connection portion 714 is configured to permit attaching the rasp 700 to a powered handpiece. In the example shown, the two sidewalls 720 of the rasp 700 are beveled inwards to narrow from the body portion 702 to the connection portion 714 and a notch is located at the end 716 of the connection portion 714 to permit attaching the rasp 700 to a powered handpiece, for example, a powered reciprocating saw handpiece.

The head portion 704 is generally rectangular in shape with a rounded distal end and includes a plurality of teeth 706 protruding from the lower surface 712 and a channel 708 cut into the upper surface 710 above the teeth. The array of teeth 706 may be used, for example, to cut away uneven areas on a bone. As shown in FIG. 7B, the channel 708 is cut completely through the head portion 704 from the upper 710 surface to the lower surface 712 such that gaps 718 are formed between the teeth 706. In other words, the head portion includes an upper surface 712, a lower surface 710 opposite the first surface, and sidewalls 720 connecting the first and second surfaces. The first surface includes the multiple teeth 706 and gaps 718 positioned between the teeth. The second surface defines an opening 722 of the channel and the channel 708 extends from the opening to the multiple teeth 706 and gaps 718 along an axis perpendicular to a longitudinal axis of the head portion 704.

The opening 722, channel 708, teeth 706, and gaps 718 are configured such that, during use, bone fragments are able to move through the gaps 718, through the channel 708, and out the opening 722 of the channel. Thus, the channel 708 cut above the teeth 706 may facilitate the flow of bone chips away from the teeth 706 through the gaps 718 and thereby reduce the possibility of the chips clogging the area or obscuring a user's view of a rasped bone structure, for example.

Embodiments of the rasp 700 may employ various shapes for the channel 708, as necessary. For example, the channel may be rectangular, oblong, or any other suitable shape. In some implementations, the channel may extend slightly past the teeth. For example, as illustrated in FIGS. 7A, 7B, the channel 708 extends along the longitudinal axis of the head portion 704 from the cutting surface of a first tooth 726 (at a distal end) past the cutting surface of a last tooth 728 (at a proximal end).

Figure 8A:
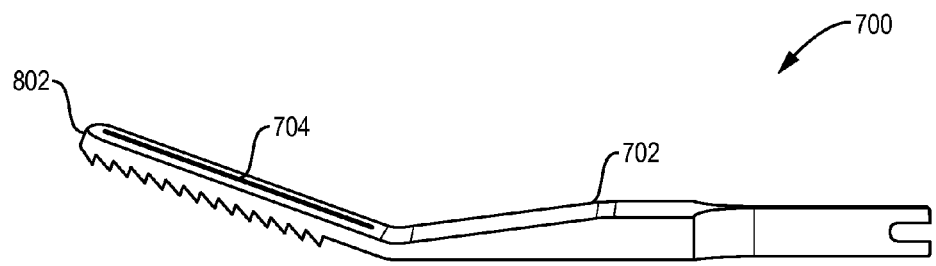
FIGS. 8A-8C are schematic illustrations of alternative embodiments of the bone contouring device of FIGS. 7A-7B having varied orientation of a head portion with respect to a body portion; (A) positive angle; (B) straight line; (C) negative angle.
Figure 8B:
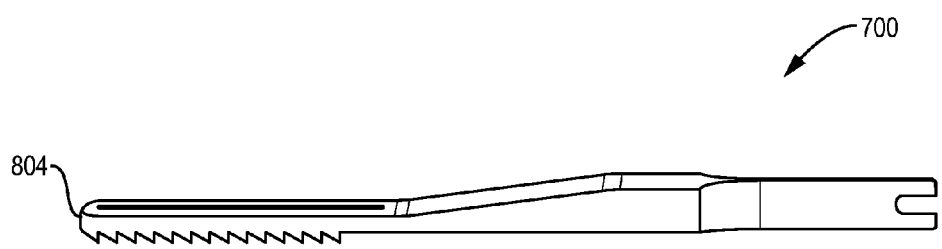
Figure 8C:
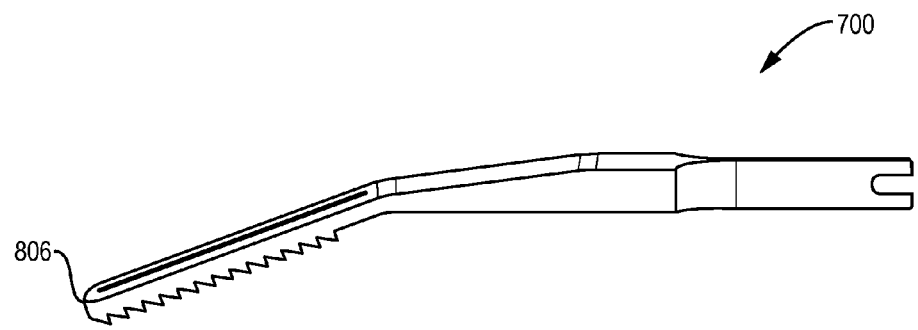

FIGS. 8A-8C illustrate several variations of the rasp 700. As depicted in the embodiments of FIGS. 8A-8C, the head portion 704 may be angled with respect to the body portion 702, for example, to accommodate different patients or surgical procedures. For instance, in one embodiment, the head portion 704 is angled upwards relative to the body portion 702 such that a longitudinal axis of the head portion 704 forms a positive angle with respect to a longitudinal axis of the body portion 702 (device 802, FIG. 8A). In another embodiment, the head portion 704 is aligned with the body portion 702 such that a longitudinal axis of the head portion 704 forms a straight line with the longitudinal axis of the body portion 702 (device 804, FIG. 8B). In a further embodiment, the head portion 704 is angled downwards relative to the body portion 702 such that a longitudinal axis of the head portion 704 forms a negative angle with respect to a longitudinal axis of the body portion 702 (device 806, FIG. 8C).

FIGS. 9A-9D illustrate a drill guide 900 for positioning a bone tunnel. Drill guide 900 includes a handle 902 located at a first end, in the form of a pistol grip, so that the surgeon may easily grasp and manipulate drill guide 900 during surgery, and an elongate aimer arm 904 towards a second end. Handle 902 includes a cylindrical bullet channel 906 for receiving an elongate drill bullet (not shown). In the illustrated embodiment, the bullet channel 906 and drill bullet are orientated horizontally relative to a slightly backwards sloping handle 902—thus providing a pistol style construction. In alternative embodiments, not shown, the handle is an in-line handle, formed substantially coaxially with the bullet channel.

In addition, the handle 902 includes a passage 908 that receives a one-way ratchet pawl adjacent to bullet channel 906, such that the ratchet pawl can engage with the drill bullet to prevent its movement within bullet channel 906. Drill bullet is sized for insertion through bullet channel 906, and has an elongated body and an angled distal tip. The elongated body of drill bullet has a cylindrical bore which provides a passageway for receipt of a guidewire. Drill bullet also includes a rack, in the form of a series of ratchet teeth or radial grooves along one side of body. The one-way ratchet pawl of handle engages with the rack and holds the drill bullet in place within bullet channel 906. Such an arrangement is shown in WO2012/061733, incorporated herein by reference in its entirety The distal tip of the drill bullet has an angled opening surrounded by teeth. The extent of the angle will largely depend on the architecture of the particular bone surface that is to be drilled. When drill bullet is inserted through bullet channel 906, the distal tip of the drill bullet provides a stable engagement with a bone surface because of the contact made between the teeth and bone surface. The drill bullet is configured to direct a guidewire into a bone surface to locate the bone tunnel.

The elongate aimer arm 904 is rounded, and has a proximal arm portion and a distal arm portion. The proximal arm portion is connected to, and extends distally from handle 902.

The distal arm portion of the aimer arm 904 includes a distal tip 910 with a spiked hook 912, and is configured to contact a bone surface (e.g., the glenoid) to secure the glenoid drill guide 900 to the glenoid. The hook 912 is small enough and positioned so as to be offset from the drill bullet and resulting drill path. Consequently, the drill will not be stopped from advancing past the hook.

FIGS. 10A-11D illustrate a drill guide 1000 used, for example, to position a drill when drilling through bone, such as a coracoid process. The guide 1000 includes a body member 1002, an actuating member or shaft 1004, a handle 1006, and a gripping head that includes a plurality of jaw members (e.g., 1008a-1008c). As discussed in detail below, the plurality of jaw members are adapted to move between an open position and a closed position for grasping a bone to be drilled. FIGS. 10A-10D illustrate the jaw members 1008a-1008c in a closed position, while FIGS. 11A-11D illustrate the jaw members 1008a-1008c in an open position.

The body member 1002 includes a distal end 1013 and a proximal end 1015 opposite the distal end 1013. The body member 1002 is fully cannulated and defines a lumen 1003 that extends from the proximal end 1015 to the distal end 1013. The lumen 1003 terminates in a first opening (not shown) at the proximal end 1015 and a second opening 1003a at the distal end 1013. The lumen 1003 is substantially straight and extends along a longitudinal axis of the body member 1002.

The body member 1002 includes a plurality of ports formed in the distal end 1013 and distributed about the circumference. For example, as illustrated in FIGS. 10A-11D, the drill guide 100 includes three ports 1010a-1010c (1010b and 1010c not shown) located at approximately 120 degrees around the circumference of the body member 1002. Each of the ports 1010a-1010c is configured to accept a corresponding geared end of a jaw member (e.g., 1012a-1012c of a jaw member 1008a-1008c). Each jaw member 1008a-1008c further includes a gripping end 1017a-1017c (1017c not shown) opposite the geared end 1012a-1012c. Each gripping end 1017a-1017c includes a protrusion 1019a-1019c.

Each jaw member 1008a-1008c and corresponding port 1010a-1010c are sized such that the side surfaces 1005 of each jaw member 1008a-1008c either nearly contact or loosely contact the corresponding inner surfaces 1007 of the port 1010a-1010c. The geared end 1012a-1012c of each jaw member 1008a-1008c includes a pair of arcuate grooves 1009 formed in the jaw member's side surfaces 1005 (one grove on each side of the jaw member). Likewise, each port 1010a-1010c includes a corresponding pair of arcuate flanges 1011 formed on opposing inner surfaces 1007 (e.g., one flange on each opposing sidewall). The arcuate flanges 1011 and grooves 1009 are configured to be of appropriate radius and size such that the arcuate flanges 1011 are slidable within the arcuate grooves 1009. Thus, the flanges 1011 and grooves 1009 form an arcuate lug and groove arrangement that allows the jaw members 1008a-1008c to pivot relative to the longitudinal axis of the body member 1002. In particular, the lug and groove arrangement allows the gripping ends 1017a-1017c to pivot towards and away from the body member 1002.

The actuating member 1004 is an elongate shaft that is disposed within the lumen 1003 of the body member 1002. The shaft 1004 is fully cannulated and defines a lumen 1024 that extends through the shaft 1004 from a proximal end of the shaft 1004 (which coincides with the proximal end 1015 of the body 1002) to the distal end of the shaft 1004 (which coincides with the distal end 1013 of the body 1002). The lumen 1024 further includes an opening (not shown) at the proximal end of the shaft 1004 to receive another surgical instrument, for example, a drill or a guide wire. So configured, a drill or guide wire inserted within the lumen 1024 can be passed from the proximal opening of the lumen 1024 to an opening 1024a of the lumen 1024 located at the distal end of the shaft 1004.

The shaft 1004 is configured to move relative to the body member 1002 along the longitudinal axis of the body member 1002, which coincides with the longitudinal axis of the shaft 1004. The shaft 1004 includes geared regions 1014a-1014c (1014c not shown) formed in a distal end and aligned with the ports 1010a-1010c. The teeth in the geared regions 1014a-1014c of the shaft 1004 are configured to mesh with the teeth in the geared regions 1012a-1012c on the jaw members 1008a-1008c. As the shaft 1004 is moved along the longitudinal axis of the shaft 1004 and body 1002, the meshed teeth cause the jaw members 1008a-1008c to move, and the arcuate lug and groove arrangement (the flanges 1011 and grooves 1009) translates this movement into a pivoting motion of the jaw members 1008a-1008c relative to the longitudinal axis of the body member 1002. In particular, as the shaft 1004 is moved relative to the body member 1002, the meshed teeth cause the arcuate flanges 1011 to slide within the arcuate grooves 1009 thereby causing the jaw members 1008a-1008c to pivot. Movement of the shaft 1004 towards the distal end 1013 results in the gripping ends 1017a-1017c pivoting away from the body member 1002 to an open position (FIGS. 11A-11D), while movement of the shaft 1004 towards the proximal end 1015 results in the gripping ends 1017a-1017c pivoting towards the body member 1002 to a closed position (FIGS. 10A-10D).

The handle 1006 is coupled to the body member 1002 and the shaft 1004 at the distal ends of the body member 1002 and the shaft 1004. The handle 1006 includes a first handle member 1006b that is coupled to the body member 1002 and a second handle member 10061006a that is coupled to the shaft 1004 at an end 1006f and to the body member 1002 at a pivot point 1006e. As the handle 1006 is squeezed, the second handle member 1006a pivots in a first rotational direction about the pivot point 1006e (e.g., clockwise). In turn, the shaft 1004 is urged in a first axial direction along the longitudinal axis of the shaft 1004 (e.g., towards the distal end 1013). Conversely, pivoting second handle member 1006a pivots in a second rotational direction about the pivot point 1006e (e.g., counter-clockwise) urges the shaft 1004 in a second axial direction along the longitudinal axis of the shaft 1004 (e.g., towards the proximal end 1015).

In certain embodiments, the handle 1006 is biased. For example, the handle includes a biasing mechanism (e.g., a scissor spring 1006c) that applies a force that tends to cause the second handle member 1006a to pivot in a desired rotational direction (e.g., counter-clockwise).

In further embodiments, the handle 1006 includes a locking mechanism (e.g., a ratchet 1006d) adapted to move between an engaged position and a disengaged position. In the engaged position, the ratchet mechanism 1006d permits pivoting of the second handle member 1006a in the first rotational direction (e.g., clockwise) and inhibits pivoting of the second handle member 1006a in the second direction (e.g., counter-clockwise). In the disengaged position, the ratchet mechanism 1006d allows pivoting of the second handle member 1006a in the second direction (e.g., counter-clockwise).

During use, when the handle 1006 is squeezed, the shaft 1004 is driven axially towards the distal end 1013 of the body member 1002, which results in the jaw members 1008a-1008c pivoting outwards to an open position. The ratchet mechanism 1006d holds the jaw members 1008a-1008c in the open position until released. Once the ratchet mechanism 1006d is released, the scissor spring 1006c forces the handle 1006 to open, which moves the shaft axially towards the proximal end 1015 of the body member 1002. When the shaft 1004 is driven axially towards the proximal end 1015 of the body member 1002, the jaw members 1008a-1008c pivot towards the body member 1002 to the closed position.

When used in a surgical procedure, a bone, such as the coracoid process, can be gripped with the jaw members 1008a-1008c to align the lumen 1024 in the proper position with respect to the bone. A guide wire or drill can then be passed through the lumen 1024 and drilled through the bone. In the event a guide wire is used, the guidewire can be left in the bone. A cannulated drill can then be placed over the guide wire and used to drill a hole through the bone.

In some implementations, the handle 1006 is coupled to the body member 1002 and the shaft 1004 such that squeezing the handle 1006 moves the shaft 1004 axially towards the proximal end 1015, thereby resulting in the jaw members 1008a-1008c pivoting towards the body member 1002 to a closed position with the ratchet mechanism 1006d holding the jaw members 1008a-1008c in the closed position. When the ratchet mechanism 1006d is released, the scissor spring 1006c opens the handle 1006, result in the jaw members 1008a-1008c pivoting away from the body member 1002 towards the open position.

It may be understood that, in alternative embodiments, mechanisms other than those illustrated herein may be provided for biasing and/or locking the handle. Furthermore, the number of jaw members may be varied. In some embodiments, the drill guide includes only a pair of jaw members arranged around the circumference of the body member (e.g., 180° apart). In other implementations, the guide includes more than three jaw members, which may be spaced equally or unequally around the circumference of the body member. In some implementations the location of the arcuate flanges and grooves are reversed. For example, the flanges may be located on the surfaces of the jaw members, while the grooves are formed on the inner surfaces of the ports. Furthermore, some implementations may use different shaped arcuate flanges and grooves, for example, the flanges and grooves may have a dovetail cross section, a rectangular cross section, or a key-hole shaped cross-section.

Figure 12:
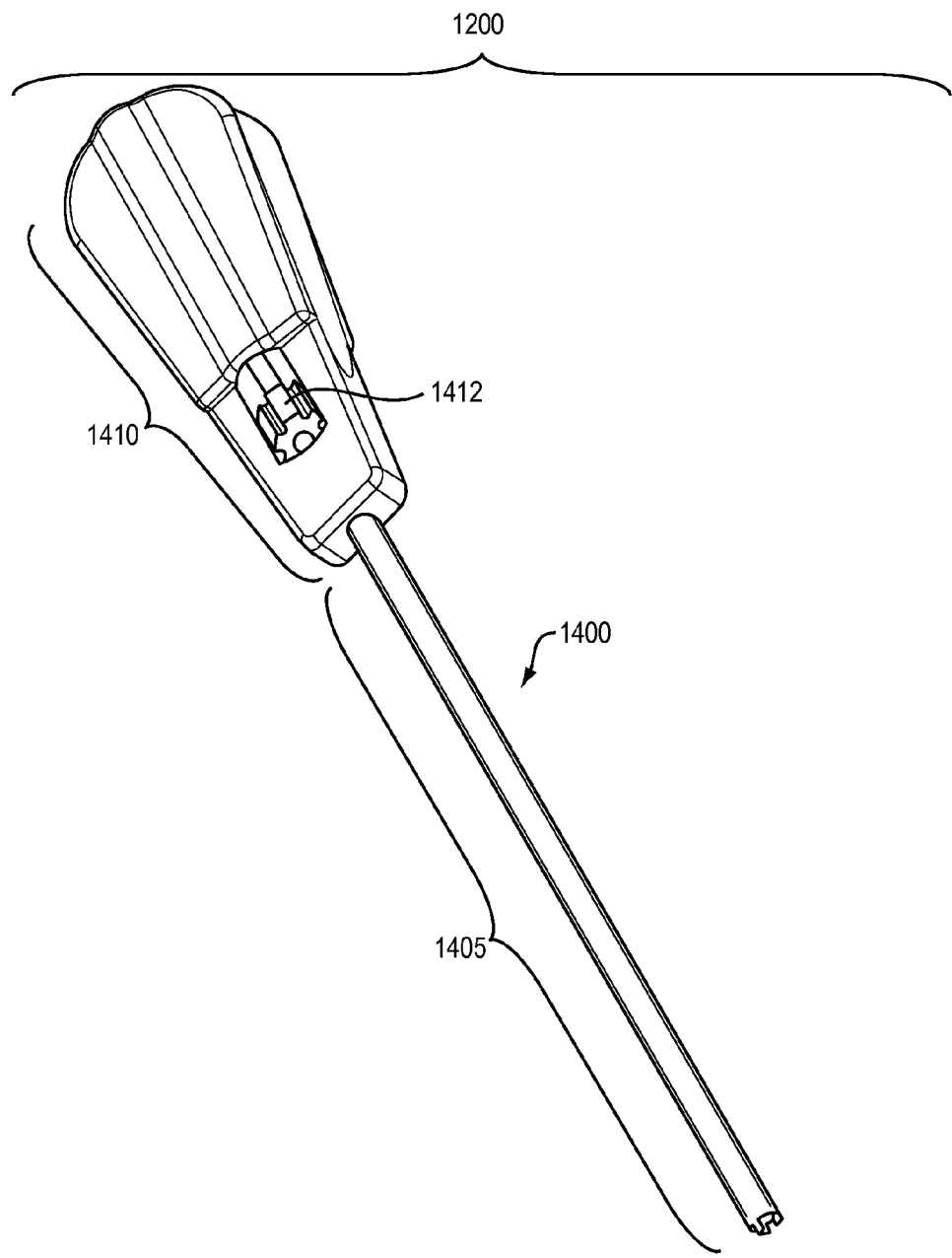
FIG. 12 is a schematic illustration of an embodiment of a self-retaining driver system.

FIG. 12 illustrates an example perspective view of a screw button and self-retaining driver system 1200. This system includes screw button 1300 and screwdriver 1400. The screw button 1300 and screwdriver 1400 include an active self-retaining mechanism that securely and rigidly connects the screw button 1300 to a tip of screwdriver 1400. This secure attachment is such that the screw button 1300 can be driven into bone or other media without requiring manually holding the screw button 1300 on the tip of the screwdriver 1400. The active self-retaining mechanism can be released after fully or partially advancing the screw button 1300 into bone media.

Referring to FIGS. 12, 13A, 13B, and 13C, the screw button includes an elongated member having a distal end 1305, a proximal end 1310, and a longitudinal axis 1315. The elongated member is generally cylindrical, though other cross-sectional shaft shapes can be used. At least a portion of the distal end 1305 has external threading 1320 adapted to advance the screw button into bone media. In some embodiments external threading 1320 can extend or cover essentially the entire screw button 1300, while in other embodiments the external threading 1320 covers just a portion of the elongated member or shaft in general. External threading geometry can be based on a particular media of use, or a particular application.

Figure 13C:
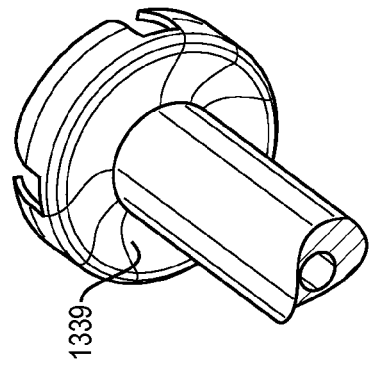
FIGS. 13A-13C are schematic illustrations of a screw button; (A) side view; (B) perspective view of proximal end; (C) perspective view of distal end.
Figure 13B:
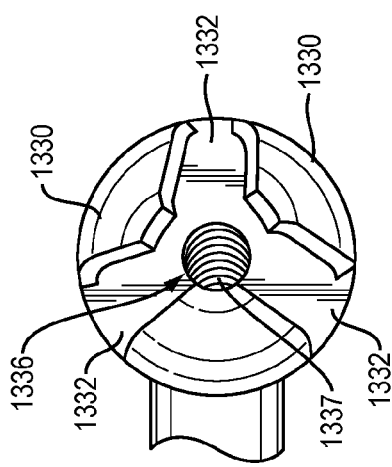
Figure 13A:
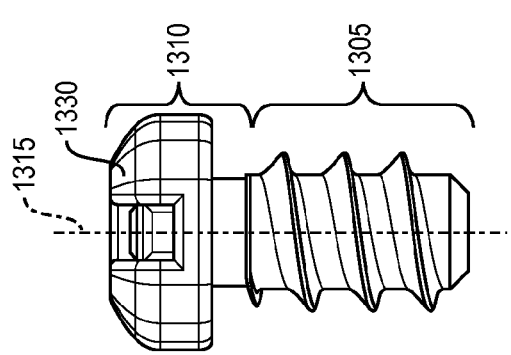

The proximal end 1310 or head of screw button 1300 has a force-receiving structure 1330, configured to receive applied torque. Typically the applied torque will be transferred to the screw button 1300 from screwdriver 1400. The force-receiving structure 1330 can have various shapes, sizes and configurations. FIG. 13B shows force-receiving structure 1330 defining slots 1332. In this example there are thr16 of slots 1332, defined essentially by protrusions/structures in the proximal portion 1310 of the screw button 1300. In other embodiments there may be a single slot or at least two slots.

Note that, in alternative embodiments, instead of defining slots, the force-receiving structure can instead define a number of lobes as recessed features for accepting the screwdriver, such as three or more lobes sized and shaped to connect with corresponding lobe structures of the external shaft of the screwdriver. Moreover, the force-receiving structure can be embodied as any pentagon, lobe, or slot arrangement, including conventional drive geometry. In some embodiments, the force-receiving structure is a recessed design having a shape that corresponds to the force-transfer structure of the screw button driver.

The screw button 1300 is cannulated in that the screw button 1300 defines a passage 1334 or lumen that follows the longitudinal axis 1315. The defined passage 1334 is sized to enable the screw button 1300 to travel along a guide wire as well as have suture pass through the screw button.

The proximal end 1310 of screw button 1300 defines a socket 1336 having internal threading 1337. The defined socket 1336 is aligned with the defined passage. For example, the defined socket 1336 can be concentric with the defined passage, sharing a longitudinal axis. The defined socket can also be centered with the force-receiving structure. The defined socket can have a larger diameter than the passage 1334. In alternative embodiments, this feature is not required. FIG. 13C illustrates concave surface 1339, which is essentially a bottom side of the screw head. With such curvature, an outside edge of the screw button head first contacts bone media before a surface adjacent to the shaft.

Referring now to FIGS. 12, 14A, 14B, 14C, and 14D, the screw button driver 1400 includes a shaft portion 1405 connected to a handle portion 1410. The shaft portion 1405 includes an external shaft 1420 and an internal shaft 1430. The internal shaft 1430 is positioned within the external shaft 1420. The internal shaft 1430 is configured to rotate independent of the external shaft 1420. The external shaft 1420 can be fixedly connected to handle portion 1410. Thus, the external shaft defines a longitudinal space or cavity within which the internal shaft can rotate and slide.

A distal end 1411 (driver tip) of the external shaft 1420 has a force-transfer structure 1425 configured to transfer applied torque to the force receiving structure 1330 of the screw button 1300 when in contact with the force-receiving structure 1330. A distal end 1411 of the internal shaft 1430 has external threading 1426 adapted to advance into the defined socket 1336 of the screw button 1300 such that when advanced into internal threading 1337 of the defined socket 1336, the screw button 1300 is securely attached to the screw button driver 1400 via the internal shaft 1430 such that the force-transfer structure 1425 is in contact with the force-receiving structure 1330.

The handle portion 1410 further includes a rotation mechanism 1412 that controls rotation of the internal shaft 1430 independent of the external shaft 1420. The rotation mechanism 1412 can be a rotatable wheel, a lever, or other manually controlled mechanism that controls the internal shaft 1430.

The rotation mechanism can be framed within an opening defined by or within handle portion 1410. The rotation mechanism 1412 can also slide longitudinally with the handle portion 1410 or defined window. Sliding the rotation mechanism 1412 within the framed opening causes the internal shaft 1430 to travel longitudinally within the external shaft 1420. The amount of travel can be sufficient for the internal shaft 1430 to retract within the external shaft 1420, and to extend to couple with the defined socket 1336.

The screw button driver 1400 is configured as cannulated through its entire longitudinal axis by defining a passage 1444 that follows a longitudinal axis 1415 of the screw button driver 1400 such that the screw button driver 1400 can travel along a guide wire. Moreover, the self-retaining mechanism is configured such that when the screw button 1300 is being securely retained by the screw button driver 1400, the coupled system (screw retained by driver) still provides a passage or lumen for sliding along a guide wire, essentially following a same longitudinal axis through the handle 1410, internal shaft 1430, and screw button 1300.

Figure 15A:
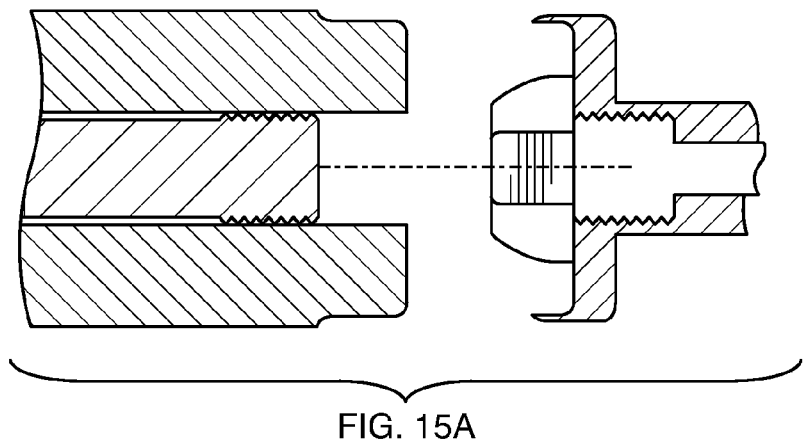
FIGS. 15A-15C are schematic illustrations of a progression of operations for engaging an active self-retaining mechanism.
Figure 15B:
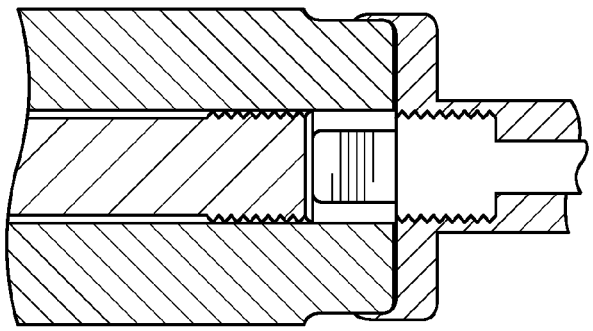
Figure 15C:
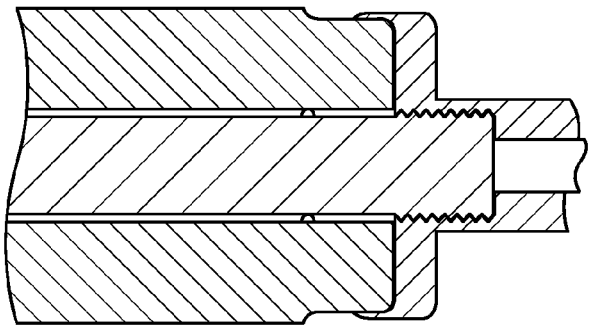

FIGS. 15A-15C shows progression of steps for engaging the active self-retaining mechanism. FIG. 15A shows a side sectional view of a tip of screwdriver 1400 aligned with screw button 1300. In FIG. 15B, the screwdriver 1400 and/or screw button 1300 have been moved so that the force receiving structure is in contact with the force transfer structure, but without the internal shaft extended. In FIG. 15C, the internal shaft has been manipulated or advanced so that external threading of the internal shaft engages with internal threading of the screw button, thereby actively retaining the screw button 1300 against the screwdriver.

Figure 16:
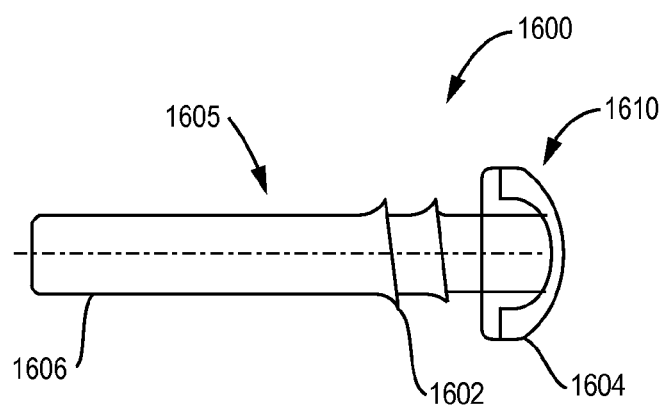
FIG. 16 is a schematic illustration of an alternative embodiment of a screw button.

FIG. 16 shows an embodiment of an alternative screw button 1600 in which the threads only extend over a portion of the screw button. The screw button 1600 includes a proximal portion 1610 with a head configured like the head of the distal portion 1310 of the screw button 1300. The screw button 1600 has a distal portion 1605 that includes a shaft that has a threaded portion 1602 at a proximal portion of the shaft, near the head of the proximal portion 1610. The shaft has a non-threaded portion 1606 at a distal portion of the shaft.

When the screw button 1600 is used in the procedure described above, the non-threaded extension may cross the fracture line (between the resected coracoid process and the glenoid) to provide stability in the shear direction.

FIG. 17 illustrates a surgical saw 1700 used, for example, to resect a piece of bone for use in a bone graft procedure. The surgical saw 1700 includes a tang 1702, a blade portion 1704 having an array of teeth 1706, and a connection portion 1708 for attaching the surgical saw 1700 to a reciprocating saw handpiece (e.g., a powered handpiece).

The tang 1702 is a substantially flat rectangular structure having a thickness, $T_1$, with the blade portion 1704 attached at one end (a distal end), and the connection portion 1708 at the end opposite the blade portion 1704 (a proximal end). The connection portion 1708 is configured to connect the surgical saw 1700 to a powered handpiece. In the example shown, the connection portion 1708 is thinner than the tang 1702 and includes a notch 1716 to permit attachment to a powered handpiece, for example, a powered reciprocating saw handpiece.

The blade portion 1704 includes an array of teeth 1706 and has two surfaces, a first surface 1710 and second surface 1712. The second surface 1712 is slightly recessed from the first surface 1710 and is formed, for example, by etching. In the example shown, the blade 1704 has a first surface 1710 and etched second surface 1712 on both sides. As a result, the blade portion 1704 includes a recessed portion formed from the second surface 1712 on both sides and a non-recessed (or raised) portion formed from the first surface 1710 on both sides. The recessed portion has a thickness, $T_2$, which is thinner than the non-recessed (or raised) portion, which has a thickness, $T_3$. This thinner (recessed) portion of the blade may prevent the blade 1704 from becoming jammed in a cutting notch of a bone while sawing. Some of the teeth 1714 are cut into the second surface while others are cut into the first surface 1710. In other words, some teeth may have a thickness $T_2$ while others have a thickness $T_3$, where $T_2$ is less than $T_3$.

As shown in FIG. A, the teeth 1706 may alternate thickness between $T_2$ and $T_3$, thus creating a divergent set of teeth. A divergent set of teeth may improve the surgical saw device's 1700 cutting performance by transporting bone chips away from the cutting area and creating a flat sawn surface on the bone, for example. In alternative embodiments, other may be used. For example, pattern including one tooth having a thickness of $T_3$ followed by two teeth having a thickness of $T_2$.

In some implementations the first surface 1710 may be in the same plane as the surface 1711 of the tang 1702. For example, the first surface 1710 may be an original, unetched surface of the surgical saw device 1700 and have a thickness, $T_3$, equal to the thickness of the tang, $T_1$. In other implementations, the tang's surface 1711 may reside in a different plane than the blade's first surface 1710. For example, the thickness of the non-etched portion of the blade 1710, $T_3$, may be different than the thickness of the tang 1702, $T_1$. In addition, some implementations may have an etched surface on only one side of the blade, thus leaving the opposing side of the blade substantially flat, for example. Furthermore, in other embodiments, some implementations the teeth are made by laser cutting instead of grinding to reduce costs, for example.

FIG. 18 is a photograph 1800 of an example surgical saw device 1700. In the photograph 1800, the surgical saw 1700 is attached to a powered reciprocating saw handpiece 1802 and is being used to cut the coracoid process. For example, the handpiece connection 1708 portion of the tang 1702 may be inserted into an attachment receiving slot 1806 on the powered handpiece 1804 to attach the surgical saw 1700 to the powered handpiece 1804.

Figure 19A:
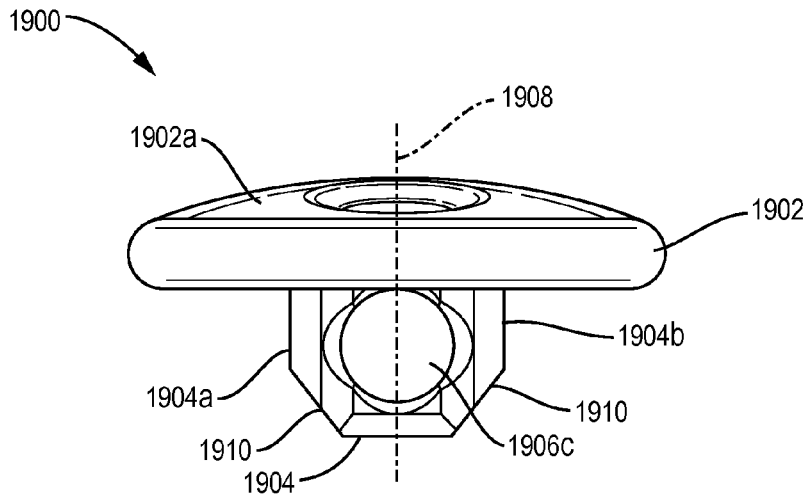
FIGS. 19A-19C are schematic illustrations of a surgical fastener; (A) side view; (B) view of first surface; (C) perspective view of second surface.
Figure 19B:
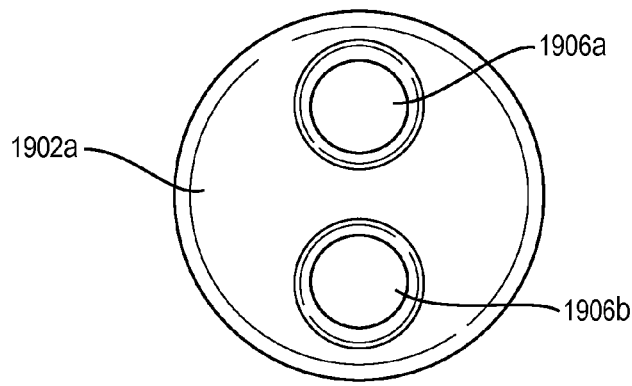
Figure 19C:
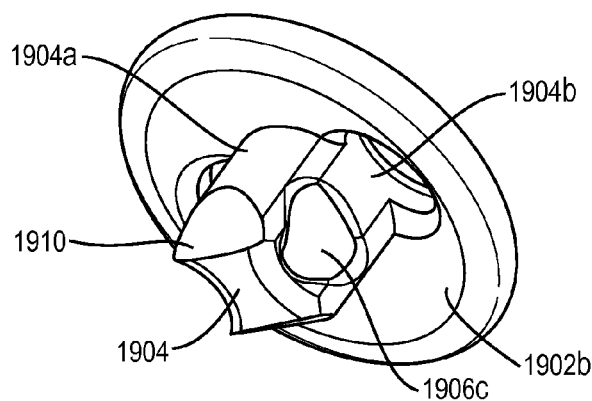

FIGS. 19A-19C illustrate an example of a surgical fastener 1900 used, for example, to secure a piece of bone in place during a bone graft procedure. The surgical fastener 1900 includes a body 1902, a post 1904, and a plurality of holes (e.g., 1906a-1906c). The device 1900 can be made from metal, a suture based, absorbable material, or collagen based material that may hold or carry healing elements (for example, blood, prp, or stem cells).

The body 1902 is generally circular and includes opposing first and second surfaces 1902a, 1902b. The first surface 1902a of the fastener 1900 is convex and the second surface 1902b is concave such that the fastener 1900 has a bowl-shaped profile. A diameter of the first surface 1902a, $D_1$, may be varied according to certain embodiments. For example, the diameter may be varied to accommodate a patient or procedure. In one embodiment, the diameter $D_1$ is 14 mm.

The body 1902 further includes a plurality of first holes formed therein, extending through the body 1902 from the convex first surface 1902a to the concave second surface 1902b. For example, as illustrated in FIGS. 19A-19C, the body 1902 includes two holes 1906a and 1906b.

A post 1904 is coupled to the body 1902 at a first end and extends outwards along a longitudinal axis 1908 from the concave second surface 1902b. The longitudinal axis 1908 of the post is substantially perpendicular to the concave second surface 1902*b*. The post 1904 possesses a diameter, $D_2$, that extends perpendicular to the axis 1908 and is less than the diameter $D_1$ of the body 1902. In an embodiment, the post 1904 further possesses a generally cylindrical shape and defines an outer curved side surface 1904*a*. The post 1904 further includes a second hole 1906*c* formed therein, extending transverse to the longitudinal axis 1908 (e.g., through opposite sides of the outer curved surface 1904*a*).

The diameter $D_2$ of the post 1904 is larger than a separation distance between the first pair of holes 1906*a* and 1906*b*. As a result, the post 1904 is axially coincident with a portion of each of the first pair of holes 1906*a* and 1906*b*. In this instance, the holes 1906*a* and 1906*b* extend partially through opposing sides of the curved surface 1904*a* of the post 1904 parallel to the longitudinal axis 1908 forming an arcuate surface 1904*b* on the post 1904. In other words, the sides of the post 1904 under the holes 1906*a* and 1906*b* include a concave surface that forms semi-circular passages on both sides of the post 1904. The arcuate surfaces of the passages generally follow the circumference of the holes 1906*a* and 1906*b*. The semi-circular passages can accommodate suture passed through the holes 1906*a* and 1906*b*. The post 1904 includes one or more a chamfered surfaces 1910 formed in a second end to aid in inserting the post into a passage that may be made in a bone, for example.

Figure 20A:
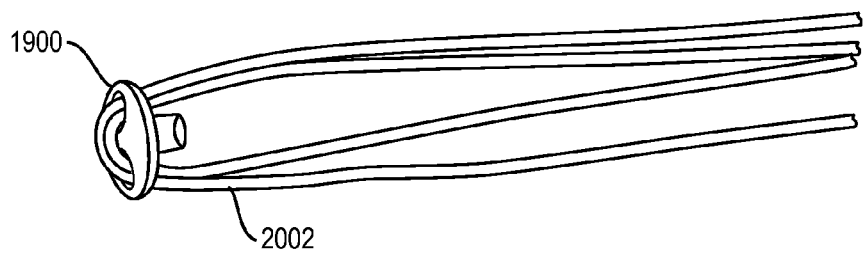
FIG. 20A is a photograph of the surgical fastener of FIGS. 19A-19C engaged with a suture loop according to a first manner of suture routing.
Figure 20B:
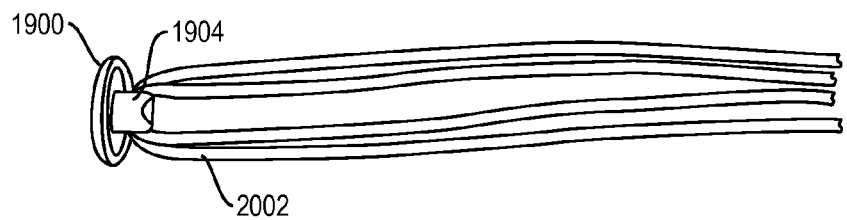
FIGS. 20B-20C illustrate the surgical fastener of FIGS. 19A-19C engaged with a suture loop according to a second manner of suture routing; (B) photograph; (C) schematic illustration.
Figure 20C:
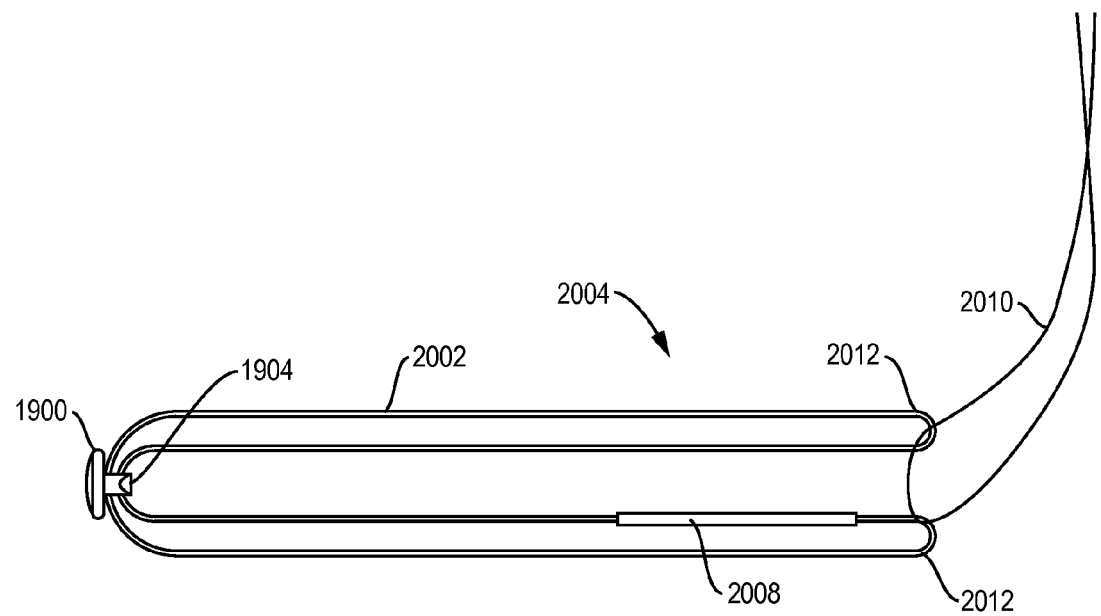

Embodiments illustrated in FIGS. 20A-20C present examples of how a suture 2002 may be passed through a surgical fastener 1900. In certain embodiments, the suture 2002 is a continuous loop of suture, formed from a length of suture material that is spliced 2008 at two free ends (not shown).

The form of the suture may be varied, in certain embodiments. For example, the suture may be formed in a suture loop or bundle. In further embodiments, the suture may be formed from a high-strength polyethylene (for example, Ultrabraid® Sutures, Smith & Nephew, Inc., Andover, Mass., USA) or may be formed from metallic wire.

The fastener 1900 is configured such that the suture loop 2002 can be routed through either the first pair of holes 1906*a* and 1906*b* or the second hole 1906*c*, with two suture loop ends 2012 (FIG. 20C) extending from the fastener 1900. For example, as illustrated in FIG. 20A, the suture loop 2002 is passed in one of holes 1906*a* and 1906*b*, along the first surface 1902*a*, and back through the other of holes 1906*a* and 1906*b* (FIG. 20A). The suture loop 2002 may then be passed through a passage made in a bone during a surgical procedure with the fastener 1900 creating an anchor point on the bone against which the suture loop 2002 may be tensioned. For example, the body 1902 is configured such that the second surface 1902*b* provides sufficient contact area with a bone to prevent the fastener 1900 from being pulled by tension on a suture loop 2002 through the passage in the bone. Passage of the suture 2002 through holes 1906*a* and 1906*b* may be used if the fastener 1900 is placed on a knot side of the suture loop 2002, for example.

In an alternative embodiment, the suture loop 2002 can be routed through the hole 1906*c* in the post 1904 (FIGS. 20B and 20C), for example, when the fastener 1900 is on a non-knot side of the suture and the bone. The suture loop 2002 may then be passed through a passage in a bone. As the suture loop 2002 is tensioned, the suture may align the post 1904 with the passage.

As illustrated, the suture loop 2002 can be part of a suture construct B06 formed from the suture loop 2002 and a length of pull suture 2010 threaded through two loop ends 2012 created when the suture loop 2002 is folded over. The two ends of the pull suture 2010 are tied forming a second loop which may be easily pulled through a cannula implant or other surgical instrument with the aid of a single hook, for example. As the pull suture 2010 is pulled through a cannula the loop ends 2012 are pulled through the cannula with the pull suture 2010 thereby allowing a surgeon to easily thread four strands of suture material through a narrow passage, for example. The suture loop 2002 may be formed from SZ3 or 4 suture and the pull sutures may be formed from SZ0 suture.

Variations of the fastening 1900 may be used during surgical procedures, for example, the shape of the body 1902 may be changed to accommodate the cortical tip of the patient's coracoid process.

FIGS. 21A-21C illustrate an example of a suture tensioner 2100 used, for example, to tension a suture during a surgical procedure. Tensioner 2100 includes a shaft 2102, a body 2104, and a suture tensioning member 2106.

The shaft 2102 is generally shaped like an elongated hollow rod. The shaft 2102 includes a distal end 2102*a* a proximal end 2102*b* and defines a suture lumen 2102*c* that extends from the distal end 2102*a* to the proximal end 2102*b*. The body 2104 is coupled to the proximal end 2102*b* of the shaft 2102 and is configured to receive a suture tensioning member 2106. The suture tensioning member 2106 is, e.g., a screw having a broad wing nut shape at the screw head. In more detail, the tensioning member 2106 includes a retractable screw member 2108 having a distal end 2108*a* and a proximal end 2108*b*. The retractable screw member 2108 is coupled to the body 2102 such that rotating the retractable screw member 2108 counterclockwise moves suture tensioning member 2106 axially away from the distal end 2102*a* of the shaft 2102 and along a central longitudinal axis of the shaft 2110, while rotating the retractable screw member 2108 clockwise moves suture tensioning member 2106 axially towards the distal end 2102*a* of the shaft 2102 and along a central longitudinal axis of the shaft 2110.

The tensioning member 2106 includes a first post 2116*a* and a second post 2116*b* coupled to the proximal end 2108*b* of the retractable screw member 2108 forming, e.g., a wing nut. The first post 2116*a* extends outwards along an axis 2118 that is perpendicular to the central longitudinal axis 2110 and the second post 2116*b* extends outwards along the axis 2118 opposite the first post 2116*a*. The first and second posts 2116*a* and 2116*b* may aid in rotating the tensioning member 2106, for example. The retractable screw member 2108 defines a suture lumen 2120 that extends between the distal and proximal ends 2108*a* and 2108*b* of the retractable screw member 2108 and is configured to be coaxial to the shaft's suture lumen 2102*c*. The suture lumen 2120 includes an opening (not shown) at the distal end 2108*a* of the retractable screw member 2108 and an opening 2122 at the proximal end 2108*b* of the retractable screw member 2108.

The retractable screw member 2108 also includes outer feature 2124 to which the suture can be coupled. In the example shown, the retractable screw member 2108 includes a smooth cylindrical portion 2124 under the wing nut. A free end of the suture can be wrapped around this cylindrical portion 2124.

The suture tensioner 2100 may be used to apply tension to the suture prior to tying the final securing knots (e.g. surgeon's knots) in the free end of the suture, for example. In operation, the free end of a suture is first passed into an opening 2112 at the distal end 2102*a* of the shaft 2102, through the shaft lumen 2102*c* and out of an opening 2114 at the proximal end 2102*b* of the shaft 2102. The free end of a suture is passed from the opening 2114 at the proximal end 2102*b* of the shaft 2102 through the suture lumen 2120 in the retractable screw member 2108 and out the opening 2122 at the proximal end 2108*b* of the retractable screw member 2108. Next, the free end of the suture is coupled to the tensioning member 2106, for example, by looping or tying it to the smooth cylindrical portion 2124 under the wing nut. The suture tensioning member 2106 is then actuated to exert a force on the suture in a direction away from the distal end 2102*a* of the shaft 2102, for example, by rotating the retractable screw member 2108 counterclockwise. For example, the suture may be attached to tissue or a bone at one end thus as the suture tensioning member 2106 applies force away from the distal end 2102*a* of the shaft 2102 the suture is pulled tight. The suture may be passed through the shaft lumen 2102*c* and the suture lumen 2120 using a suture passer.

The shaft 2102 includes an opening 2128 located between openings 2112 and 2114 and near the distal end 2102*a*. Opening 2128 may be used to pass the free end of the suture a shorter distance through the lumen 2102*c*. The distal end of the shaft 2102 includes a construct engaging feature 2126 configured to engage a surgical construct. The construct engaging feature is a set of one or more posts 2126*a*, for example, similar to the head of a screwdriver. The set of posts 2126*a* may be used to engage the head of a surgical screw attached to a piece of bone in a grafting procedure and thus permit a surgeon to manipulate the piece of bone while tensioning a suture that is passed through a lumen in the screw, for example. For example, when the screw button (e.g. as shown in FIGS. 12-16) is inserted into a resected coracoid the set of posts 2126*a* may engage the head of the screw button thus allowing the surgeon properly position the resected coracoid.

In some implementations, the tensioner 2100 includes a tension measuring mechanism coupled to the suture tensioning member 2106, for example, to indicate the tensile force applied to the suture. The implementation illustrated in FIGS. 21A-21C uses a rigid shaft 2102, but in some implementations, the shaft 2102 may be a flexible shaft. For example, the shaft 2102 may be puzzle cut, composed of interlocking sections, or made of a longitudinally stiff and radially flexible material. A flexible shaft 2102 may facilitate tensioning sutures in difficult to reach locations during a surgical procedure, for example.

FIG. 22 illustrates an example of a suture tensioner 2200 having a transverse suture tensioning member 2202. The suture tensioner 2200 is similar to the suture tensioner 2100 described above, however, the suture tensioning member 2106 is replaced with a transverse suture tensioning member 2202. In an embodiment, the transverse suture tensioning member 2202 is, a shaft having a broad wing nut shape on one end. In more detail, the tensioning member 2202 includes a shaft member 2204 having a first end 2204*a* and a second end 2204*b*. The shaft member 2204 is coupled to the body 2102 along a tensioner longitudinal axis 2206 that is perpendicular to the central longitudinal axis 2110 and is configured such that rotating the transverse tensioning member 2202 winds a suture around the first end 2204*a* of the shaft member 2204, thereby exerting a force on the suture in a direction away from the distal end of the shaft 2102 and tensioning the suture. In some implementations the free end of the suture is attached to the tensioning bar 2202 by friction between a surface 2208 of the tensioning bar 2202 and the suture while the suture is wound around the tensioning bar 2202. An outer feature 2210 (e.g. a loop) is coupled to the first end 2202*a* of the tensioning bar 2202 and may be used to help with winding the suture. For example, the free end of the suture may be tied to (or simply passed through) the outer feature 2210 on the transverse tensioning member 2202 and then the tensioning bar 2202 is rotated to wind the suture.

The transverse tensioning member 2202 includes a first post 2212*a* and a second post 2212*b* coupled to the second end 2204*b* of the shaft member 2204 forming, e.g., a wing nut. The first post 2204*a* extends outwards along an axis 2214 that is perpendicular to the tensioner longitudinal axis 2206 and the second post 2212*b* extends outwards along the axis 2214 opposite the first post 2212*a*. The first and second posts 2212*a* and 2212*b* may aid in rotating the transverse tensioning member 2202, for example.

Figure 23C:
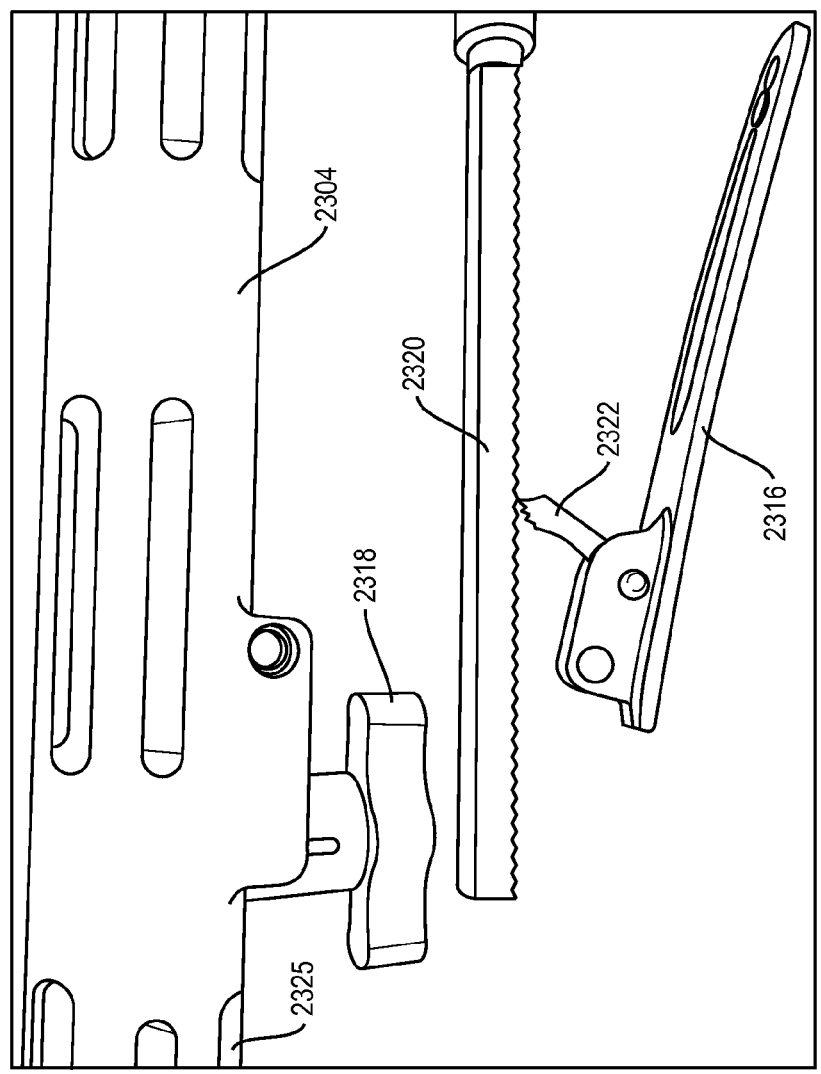

FIGS. 23A-23C illustrate an example of a ratcheting tensioner 2300 used, for example, to tension a suture during a surgical procedure. Tensioner 2300 includes a shaft 2302, a body 2304, and a suture tensioning member 2306. The shaft 2302 is generally shaped like an elongated hollow rod. The shaft 2302 includes a distal end 2302*a* a proximal end 2302*b* and defines a suture lumen 2302*c* that extends from the distal end 2302*a* to the proximal end 2302*b* with an opening 2312 at the distal end 2302*a* and an opening 2314 at the proximal end 2302*b*. The body 2304 is coupled to the proximal end 2302*b* of the shaft 2302 and is configured to receive a suture tensioning member 2306. The suture tensioning member 2306 includes a barrel 2308 coupled to a ratcheting mechanism 2309. The barrel 2308 is configured to be coupled to the free end of a suture 2307 that is passed in the opening 2312, through the lumen 2302*c* and out the opening 2314. When a handle 2316 is actuated the ratchet mechanism 2309 is configured to move the barrel 2308 away from the shaft's distal end 2302*a* and along an axis parallel to a central longitudinal axis 2310 of the tensioner 2300 thereby exerting a force on the suture in a direction away from the shaft's distal end 2302*a*. The ratcheting mechanism 2309 may then be released by turning a wing nut 2318, for example.

The ratcheting mechanism 2309 includes a handle 2316, a toothed or radially grooved ratcheting member 2320 (to which the barrel 2308 is connected), a pawl 2322, a spring 2324, and a wing nut 2318. The handle 2316 is pivotally coupled to the body 2304 and configured to actuate the ratcheting mechanism 2309 when depressed in a direction towards the body 2304. A pawl 2322 coupled to the handle 2316 engages the teeth on the ratcheting member 2320, disposed within the body 2304, through an opening 2325 in the body 2304. The pawl 2322 and ratcheting member 2320 are configured such that the pawl 2322 exerts a force on the ratcheting member 2320 to incrementally move the ratcheting member 2320 (and hence the barrel 2308) in a direction away from the shaft 2302 and 30 along the central longitudinal axis 2310 against spring pressure. The spring pressure is created as the spring 2324 is compressed inside the body 2304 between an internal surface at the distal end of the body 2326 and a substantially flat surface at a distal end of the ratcheting member 2328. The wing nut 2318, coupled to the body 2304 is configured to prevent the ratcheting member 2320 from moving back towards the shaft 2302 when the handle 2316 is released. In addition, the wing nut 2318 is configured to release the ratcheting member 2320 allowing the spring pressure to push the ratcheting member 2320 back towards the shaft 2302 when the wing nut 2318 is rotated.

In some embodiments, the tensioner may include one or more of the following components. In one aspect, the tensioner may include a damper to prevent the ratcheting mechanism from slamming against the body when released, for example. In another aspect, the tensioner may include a tension measuring mechanism coupled to the suture tensioning member, for example, to indicate the tensile force applied to the suture. In a further aspect, the shaft may be a flexible shaft, for example, the shaft may be puzzle cut, composed of interlocking sections, or made of a longitudinally stiff and radially flexible material. A flexible shaft may facilitate tensioning sutures in difficult to reach locations during a surgical procedure, for example.

The terms comprise, include, and/or plural forms of each are open ended and include the listed parts and can include additional parts that are not listed. And/or is open ended and includes one or more of the listed parts and combinations of the listed parts.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:

1. A surgical repair method, comprising:
preparing a first grafting surface on a glenoid bone, the first grafting surface positioned adjacent an area of bone loss within the glenoid bone;
preparing a second grafting surface on an inferior surface of a coracoid process bone;
drilling a first passage through the glenoid;
drilling a second passage through the coracoid process;
passing a guidewire through the first and second passages, wherein the guidewire is passed through the first passage and subsequently through the second passage;
resecting a tip of the coracoid process;
maneuvering the resected coracoid process along the guidewire such that at least a portion of the first and second grafting surfaces are in contact; and
securing the resected coracoid process to the glenoid with two surgical fasteners and a suture extending there-between.

2. The method of claim 1, further comprising spreading tissue interposed between an incision made in a patient's shoulder and at least one of the glenoid and the coracoid process with a tissue spreader, the tissue spreader comprising:
a first member comprising:
a first distal end;
a first proximal end;
a first shaft portion connecting the first distal end and the first proximal end, the first shaft portion defining a lumen; and
a first paddle portion located at the first distal end, the first paddle portion including a first spreading member with a first spreading surface that has a longitudinal axis parallel to, but offset from, a central, longitudinal axis of the first shaft portion by a first distance greater than a radius of the first shaft portion;
a second member comprising:
a second distal end;
a second proximal end;
a second shaft portion connecting the second distal end and the second proximal end and disposed within the lumen of the first shaft portion; and
a second paddle portion located at the second distal end, the second paddle portion including a second spreading member with a second spreading surface that has a longitudinal axis that is parallel to but offset from the central, longitudinal axis of the first shaft portion by a second distance greater than a radius of the first shaft portion;
wherein the first member and the second member are configured to rotate relative to each other about the central longitudinal axis between an open position and a closed position, the first spreading surface and the second spreading surface being separated by the first distance plus the second distance when the first member and the second member are in the open position.

3. The method of claim 2, wherein the first spreading surface and the second spreading surface are substantially diametrically opposed relative to the central, longitudinal axis of the first shaft portion when the first member and the second member are in the open position and wherein the first spreading surface and the second spreading surface are substantially overlapped when the first member and the second member are in the closed position.

4. The method of claim 2, wherein the tissue spreader further comprises a locking mechanism to stabilize the first and second members in the open position or the closed position, wherein the locking mechanism includes first and second saddle shaped notches on opposite sides of the first shaft portion and a post located on the second shaft portion, wherein the post rests in the first notch when the first and second members are in the open position and rests in the second notch when the first and second members are in the closed position.

5. The method of claim 2, wherein the first and second spreading members include lumens that align to form a single passage through the first and second spreading members when the first and second members are in the closed position.

6. The method of claim 2, wherein:
the first member includes a first slot from the first distal end to the first proximal end;
the second member includes a second slot from the second distal end to the second proximal end; and
the first and second members are configured such that the first and second slots are aligned when the first member and the second member are in the open position and the first and second slots are not aligned when the first member and the second member are in the closed position.

7. The method of claim 1, further comprising spreading tissue interposed between an incision made in a patient's shoulder and at least one of the glenoid and the coracoid process with a tissue spreader, the tissue spreader comprising:
a body member defining a first lumen;
an actuating member disposed within the first lumen and defining a second lumen that extends from a proximal end of the actuating member to a distal end of the actuating member, the actuating member configured to move relative to the body member; and
at least one arm coupled to the body member and the actuating member; at least one jaw member coupled to the arm;
wherein the at least one arm is coupled to the body member and the actuating member such that movement of the actuating member relative to the body member causes the at least one arm to move the jaw member away from the body member while maintaining a longitudinal axis of the jaw member parallel to a central, longitudinal axis of the tissue spreader.

8. The method of claim 7, wherein:
the at least one arm includes a first arm and a second arm, the first arm and the second arm coupled to the body member and the actuating member;
the at least one jaw member is coupled to the first arm and the second arm; and the first arm and the second arm are coupled to the body member and the actuating member such that movement of the actuating member relative to the body member causes the first arm and the second arm to move the at least one jaw member away from the body member while maintaining a longitudinal axis of the at least one jaw member parallel to a central, longitudinal axis of the tissue spreader.

9. The method of claim 8, wherein:
a first end of each arm is coupled to the at least one jaw member;
a second end of each arm includes a first geared portion, the second end of each arm and the body member being coupled to one another by one or more arcuate grooves or flanges; and
the actuating member includes a second geared portion that mates with the first gear portion such that movement of the actuating member results in movement of the second end of each arm along the grove or flange, which causes each arm to pivot relative to the central, longitudinal axis of the tissue spreader.

10. The method of claim 7, wherein the actuating member is configured to move along the central, longitudinal axis of the tissue spreader.

11. The method of claim 1, wherein drilling the first passage through the glenoid comprises:
securing a distal end of a glenoid drill guide to the glenoid; and
distally advancing a drill bullet through the drill guide, wherein the drill bullet includes a glenoid sleeve and a drill;
advancing the drill and glenoid sleeve from a posterior glenoid surface to the second grafting surface to form the first passage; and
removing the glenoid drill guide, the bullet, and the drill from a patient after forming the first passage while retaining the glenoid sleeve in place.

12. The method of claim 11, wherein drilling the second passage through the coracoid comprises:
grasping a superior surface of the coracoid process with a distal end of a coracoid drill guide;
advancing a drill and a coracoid sleeve through the coracoid drill guide and the coracoid process, from a superior coracoid surface to the second grafting surface, to form the second passage; and
removing the coracoid drill guide and the drill from the patient after forming the second passage, while retaining the coracoid sleeve in place.

13. The method of claim 12, wherein the coracoid drill guide comprises:
an elongate, cannulated body having a distal end and a proximal end and defining a lumen extending along a longitudinal axis there-between, the body further including:
a plurality of ports formed in the distal end;
an elongate, cannulated shaft positioned within the lumen and configured to slide within the lumen relative to the drill guide body, the shaft including a plurality of geared regions at a distal end, each geared region aligned with a respective one of the plurality of ports; and
a plurality of jaw members, each comprising:
a gripping end; and
a geared end opposite the gripping end;
wherein each of the geared ends are received within a respective port of the drill guide body and mesh with the geared region aligned therewith; and wherein movement of the shaft along the longitudinal axis in a second direction urges movement of each of the plurality of jaw members into a closed position, where the gripping ends of each jaw member are distanced from the drill guide body by a first distance; and
wherein movement of the shaft along the longitudinal axis in a first direction urges movement of each of the plurality of jaw members into an open position, where the gripping ends of each jaw member are distanced from the drill guide body by a second distance, greater than the first distance.

14. The method of claim 13, wherein the coracoid drill guide further comprises:
a pair of arcuate flanges formed upon opposing sidewalls of each of the plurality of ports; and
a pair of arcuate grooves formed on opposing lateral surfaces of the geared end of each of the plurality of jaw members;
wherein the arcuate flanges are configured to slide within the arcuate grooves allowing their respective jaw member to pivot relative to the longitudinal axis of the drill guide body; and
wherein, upon axial movement of the shaft relative to the drill guide body, the arcuate flanges slide within the arcuate grooves and urge their respective jaw member to pivot between the open and closed positions.

15. The method of claim 14, wherein movement of the shaft towards the distal end of the drill guide body results in pivoting of the gripping ends away from the drill guide body to the open position and movement of the shaft towards the proximal end of the drill guide body results in pivoting of the gripping ends towards the drill guide body to the closed position.

16. The method of claim 15, wherein the coracoid drill guide further comprises a handle coupled to the drill guide body and the shaft, the handle including:
a first elongate handle member, wherein a first end of the first handle is coupled to the proximal end of the drill guide body;
a second elongate handle member, wherein a first end of the second handle is coupled to the proximal end of the drill guide body and wherein the first end of the second handle is further coupled to a proximal end of the shaft at a pivot point;
wherein pivoting the second handle member about the pivot point in a first rotational direction urges the shaft in a first axial direction and pivoting the second handle member about the pivot point in a second rotational direction moves the shaft in a second axial direction.

17. The method of claim 16, wherein the coracoid drill guide further comprises a locking mechanism moveable between an engaged position and a disengaged position, wherein, in the engaged position, the locking mechanism permits pivoting of the second handle in the first rotational direction and inhibits pivoting of the second handle in the second rotational direction.

18. The method of claim 12, wherein passing the guidewire through the first and second passages comprises:
advancing a first end of the guidewire through the glenoid sleeve, from the posterior glenoid surface to the first graft surface;
guiding the first end of the guidewire towards the coracoid sleeve;
capturing the first end of the guidewire at a distal end of a capture device extending through the coracoid sleeve;

retracting the first end of the guidewire through the coracoid sleeve to the superior surface of the coracoid with the capture device; and removing the coracoid and glenoid sleeves while retaining the guidewire in place.

19. The method of claim 18, wherein securing the resected coracoid process to the glenoid further comprises:
providing a suture construct, comprising:
a first surgical fastener, comprising:
a generally circular body having opposed first and second surfaces, wherein the first surface is convex and the second surface is concave;
a pair of first holes formed within the body, extending from the convex first surface to the concave second surface;
a post having a first end and a second end, wherein the first end of the post is coupled to the concave second surface and extending along a longitudinal axis;
a second hole formed in the post, the second hole extending transverse to the longitudinal axis; and
the suture, wherein the suture is formed in a continuous suture loop;
wherein the continuous suture loop is routed through either the pair of first holes or the second hole of the first fastener such that two suture loop ends extend from the concave second surface;
attaching the suture loop ends to the guidewire; and
advancing the suture loop through the first and second passages, from the superior coracoid surface to an anterior glenoid surface, using the guidewire;
wherein the first fastener is secured to the superior coracoid surface by insertion of a portion of the first fastener into the second passage during said suture loop advancement through the first and second passageways; and
wherein the suture loop ends are passed through anterior glenoid surface.

20. The method of claim 19, wherein securing the resected coracoid process to the glenoid additionally comprises:
providing a second fastener, the second fastener comprising:
a generally circular body having opposed first and second surfaces, wherein the first surface is convex and the second surface is concave;
a pair of holes formed within the body, extending from the convex first surface to the concave second surface;
a post having a first end and a second end, wherein the first end of the post is coupled to the concave second surface and extending along a longitudinal axis;
passing a first end loop of the suture through one of the pair of holes of the second fastener;
passing a second end loop of the suture through the other hole of the pair of holes of the second fastener;
forming a half-hitch knot using the suture loop ends extending through the second fastener;
advancing the half-hitch knot into contact with the second fastener; and
further advancing the half-hitch knot so as to urge the second fastener post into the first passage.

21. The method of claim 20, wherein securing the resected coracoid process to the glenoid additionally comprises:
coupling the suture ends to a suture tensioning device; and
applying tension to the suture with the suture tensioning device.

22. The method of claim 21, wherein the tensioning device comprises:
a shaft including a distal end and a proximal end, the shaft defining a suture lumen that extends from the distal end to the proximal end, the suture lumen configured to have the suture passed from the distal end to the proximal end and out of an opening at the proximal end;
a body coupled to the proximal end of the shaft; and
a suture tensioning member coupled to the body, the suture tensioning member configured to be coupled to the suture passed out the opening at the proximal end of the shaft and, when actuated, to exert a force on the suture in a direction away from the distal end of the shaft.

23. The method of claim 22, wherein the suture tensioning member further comprises a retractable screw member coupled to the body such that rotating the retractable screw member moves the screw member along a central axis of the tensioning device to exert the force on the suture in the direction away from the distal end of the shaft.

24. The method of claim 23, wherein the retractable screw member includes:
a distal end and a proximal end; and
a suture lumen that is arranged coaxial to the suture lumen of the shaft and extends from the distal end to the proximal end;
wherein the suture lumen is further configured to have the suture passed from the distal end of the retractable screw member to the proximal end of the retractable screw member and out of an opening at the proximal end of the retractable screw member, wherein the retractable screw member includes an outer feature configured to be coupled to the suture passed out the opening at the proximal end of the retractable screw member.

25. The method of claim 22, wherein the suture tensioning member further comprises:
a tensioner barrel configured to be coupled to the suture passed out the opening at the proximal end of the shaft; and
a ratchet mechanism configured to move the tensioner barrel away from the distal end of the shaft along an axis parallel to a central axis of the tensioning device to exert the force on the suture in the direction away from the distal end of the shaft.

26. The method of claim 22, wherein the suture tensioning member further comprises a tensioning bar coupled to the body such that a longitudinal axis of the tensioning bar is oriented perpendicular to a central axis of the tensioning device, the tensioning bar configured to be coupled to the suture such that rotation of the tensioning bar exerts the force on the suture in the direction away from the distal end of the shaft.

27. The method of claim 22, wherein the distal end of the shaft is configured to engage thesecond fastener.

* * * * *